United States Patent
Chaurasia et al.

(10) Patent No.: US 11,261,429 B2
(45) Date of Patent: Mar. 1, 2022

(54) ENRICHED AND EXPANDED HUMAN CORD BLOOD STEM CELLS FOR TREATMENT OF HEMATOLOGICAL DISORDERS

(71) Applicant: ICAHN SCHOOL OF MEDICINE AT MOUNT SINAI, New York, NY (US)

(72) Inventors: Pratima Chaurasia, New York, NY (US); Ronald Hoffman, Brooklyn, NY (US)

(73) Assignee: ICAHN SCHOOL OF MEDICINE AT MOUNT SINAI, New York, NY (US)

( * ) Notice: Subject to any disclaimer, the term of this patent is extended or adjusted under 35 U.S.C. 154(b) by 0 days.

(21) Appl. No.: 14/892,772

(22) PCT Filed: May 16, 2014

(86) PCT No.: PCT/US2014/038361
§ 371 (c)(1),
(2) Date: Nov. 20, 2015

(87) PCT Pub. No.: WO2014/189781
PCT Pub. Date: Nov. 27, 2014

(65) Prior Publication Data
US 2016/0097036 A1  Apr. 7, 2016

Related U.S. Application Data

(60) Provisional application No. 61/983,805, filed on Apr. 24, 2014, provisional application No. 61/825,354, filed on May 20, 2013.

(51) Int. Cl.
C12N 5/0789 (2010.01)
G01N 33/50 (2006.01)
C12N 5/0775 (2010.01)

(52) U.S. Cl.
CPC ......... C12N 5/0647 (2013.01); C12N 5/0665 (2013.01); G01N 33/5073 (2013.01); *C12N 2500/90* (2013.01); *C12N 2501/065* (2013.01); *C12N 2501/999* (2013.01)

(58) Field of Classification Search
CPC ............ C12N 5/0647; C12N 2501/065; C12N 2501/125; C12N 2501/26; C12N 2501/145; C12N 2501/2303
See application file for complete search history.

(56) References Cited

U.S. PATENT DOCUMENTS

2005/0276793 A1* 12/2005 Milhem ............... C12N 5/0647
424/93.7
2006/0040392 A1  2/2006 Collins et al.
2006/0182724 A1* 8/2006 Riordan ................ A61K 8/982
424/93.7
2009/0175832 A1  7/2009 Zhao et al.
2009/0252711 A1  10/2009 Boquest et al.
2011/0251593 A1  10/2011 Klein et al.
2012/0301438 A1  11/2012 Cheng
2013/0171110 A1* 7/2013 Woods ................ C12N 5/0635
424/93.7

FOREIGN PATENT DOCUMENTS

| CN | 101080486 A | 11/2007 |
| CN | 102803476 A | 11/2012 |
| CN | 105705021 A | 6/2016 |
| JP | 2010/534653 A | 11/2010 |
| WO | 2009/017655 A2 | 2/2009 |
| WO | WO 2011/032166 | * 3/2011 |

OTHER PUBLICATIONS

Pesce et al., "Myoendothelial Differentiation of Human Umbilical Cord Blood-derived Stem Cells in Ischemic Limb Tissues", Circulation Research, 2003, pp. 1-12.*
Hofmeister et al., "Ex vivo expansion of umbilical cord blood stem cells for transplantation: growing knowledge from the heamtopoietic niche", Bone marrow Transplantation, 2007, vol. 39, pp. 11-23.*
Seet et al., "Valproic Acid Enhances the Engraftability of Human Umbilical Cord Blood Hematopoietic Stem Cells Expanded Under Serum-Free Conditions," European Journal of Haematology 82:124-132 (2008).
Chaurasia et al., "Chromatin-Modifying Agents Promote the Ex Vivo Production of Functional Human Erythroid Progenitor Cells," Blood 117:4632-4641 (2011).
Chaurasia et al., "Histone Deacetylase Inhibitors Promote the Ex Vivo Expansion of Cord Blood CD34+ Cells in Serum Free Cultures Accompanied by the Upregulation of Pluripotency Genes," Blood (ASH Annual Meeting Abstracts) 120:345 (2012).

(Continued)

Primary Examiner — Valarie E Bertoglio
(74) Attorney, Agent, or Firm — Fox Rothschild LLP

(57) ABSTRACT

This invention relates to an enriched population of isolated and expanded human cord blood stem cells and a method of producing an enriched population of isolated and expanded human cord blood stem cells. The expanded human cord blood stem cells are CD34+, CD90+, CD184+, CD117+, CD49f+, ALDH+, CD45RA− and express pluripotency genes SOX2, OCT4, NANOG, and ZIC3. In one embodiment, the stem cells in the enriched population of the present invention are positive for aldehyde dehydrogenase activity (ALDH+). In addition, in one embodiment the expanded stem cells are nearly depleted of T cells and B cells and contain a limited number of monocytes (CD14). Also disclosed is a method of treating a subject for a hematological disorder using the stem cells of the present invention and a method of determining the effects of a compound on hematopoietic stem cells.

8 Claims, 24 Drawing Sheets
Specification includes a Sequence Listing.

(56) References Cited

OTHER PUBLICATIONS

Burba et al., "Histone Deacetylase Inhibition Enhances Self Renewal and Cardioprotection by Human Cord Blood-Derived CD34+ Cells," PLoS One 6(7):e22158 (2011).
De Felice et al., "Histone Deacetylase Inhibitor Valproic Acid Enhances the Cytokine-Induced Expansion of Human Hematopoietic Stem Cells," Cancer Res. 65(4):1505-13 (2005).
Young et al., "Inhibitors of Histone Deacetylases Promote Hematopoietic Stem Cell Self-Renewal," Cytotherapy 6(4):328-336 (2004).
Stemcell Technologies, "StemSpanTM, The Solution to Your Hematopoietic Cell Expansion Needs," https://www.stemcell.com/media/files/brochure/BR28016 (2012).
Extended European Search Report for corresponding European Patent Application No. 14801860.9 (dated Nov. 29, 2016).
Extended European Search Report for European Patent Application No. 14801860.9 (dated Nov. 29, 2016).
Supplementary Materials and Methods for Burba et al., "Histone Deacetylase Inhibition Enhances Self Renewal and Cardioprotection by Human Cord Blood-Derived CD34+ Cells," PLoS One 6(7):e22158 (2011).
Asahara et al., "Endothelial Progenitor Cells for Postnatal Vasculogenesis," Am. J. Physiol. Cell Physiol. 287:C572-C579 (2004).
Yoder, "Human Endothelial Progenitor Cells," Cold Spring Harbor Prospectives in Medicine 2:a006692 (2012).
Cui et al., "Chromatin Signatures in Multipotent Human Hematopoietic Stem Cells Indicate the Fate of Bivalent Genes During Differentiation," Cell Stem Cell 4(1):80-93 (2009).
Seet et al., "Valproic Acid Enhances the Engraftability of Human Umbilical Cord Blood Hematopoietic Stem Cells Expanded Under Serum-Free Conditions," Eur. J. Haematol. 82(2):124-132 (2009).
Araki et al., "Chromatin-Modifying Agents Permit Human Hematopoietic Stem Cells to Undergo Multiple Cell Divisions While Retaining their Repopulating Potential," Blood 109(8):3570-3578 (2007).
Chaurasia et al., "Histone Deacetylase Inhibitors Promote the Ex Vivo Expansion of Cord Blood CD34+ Cells in Serum Free Cultures Accompanied by the Upregulation of Pluripotency Genes," Blood (ASH Annual Meeting Abstracts) 120(21):345 (2012).
Chaurasia et al., "Chromatin-Modifying Agents Promote the Ex Vivo Production of Functional Human Erythroid Progenitor Cells," Blood 117(17):4632-4641 (2011).
Graff et al., "Thrombopoietin and Hematopoietic Stem Cells," Cell Cycle 10(10): 1582-1589 (2011).
First Office Action and Search Report in Chinese Application No. 201480034563.0 (dated Dec. 15, 2017).
Kawano et al., "Ex Vivo Expansion of Human Umbilical Cord Hematopoietic Progenitor Cells Using A Coculture System With Human Telomerase Catalytic Subunit (hTERT)-Transfected Human Stromal Cells," Blood 101:532-54 (2003).
Notice of Reasons for Rejection in JP 2016-514978 dated Apr. 2, 2018 (Translation in English).
Matsunaga et al., "Ex Vivo Large-Scale Generation of Human Platelets from Cord Blood CD34+ Cells," Stem Cells 24:2877-2887 (2006).
Second Office Action and Search Report in Chinese Application No. 201480034563.0 (dated Aug. 15, 2018).
Examination Report in European Patent Application No. 14801860.9 (dated Oct. 30, 2018).
Third Office Action in Chinese Patent Application No. 201480034563.0 (dated Feb. 26, 2019).
Notice of Reasons for Rejection in Japanese Patent Application No. 2016-514978 (dated Apr. 2, 2018).
Seita et al., "Hematopoietic Stem Cell: Self-Renewal Versus Differentiation," Wiley Interdiscip. Rev. Syst. Biol. Med. 2(6): 640-653 (2010).
Office Action in Canada Application No. 2,912,688 (dated Mar. 6, 2020).
Notta et al., "Isolation of Single Human Hematopoietic Stem Cells Capable of Long-Term Multilineage Engraftment," Science 333:218-221 (2011).
PCT International Search Report and Written Opinion corresponding to PCT/US2014/038361, filed May 16, 2014 (dated Oct. 14, 2014).

\* cited by examiner (C)

FIGs. 17A-G

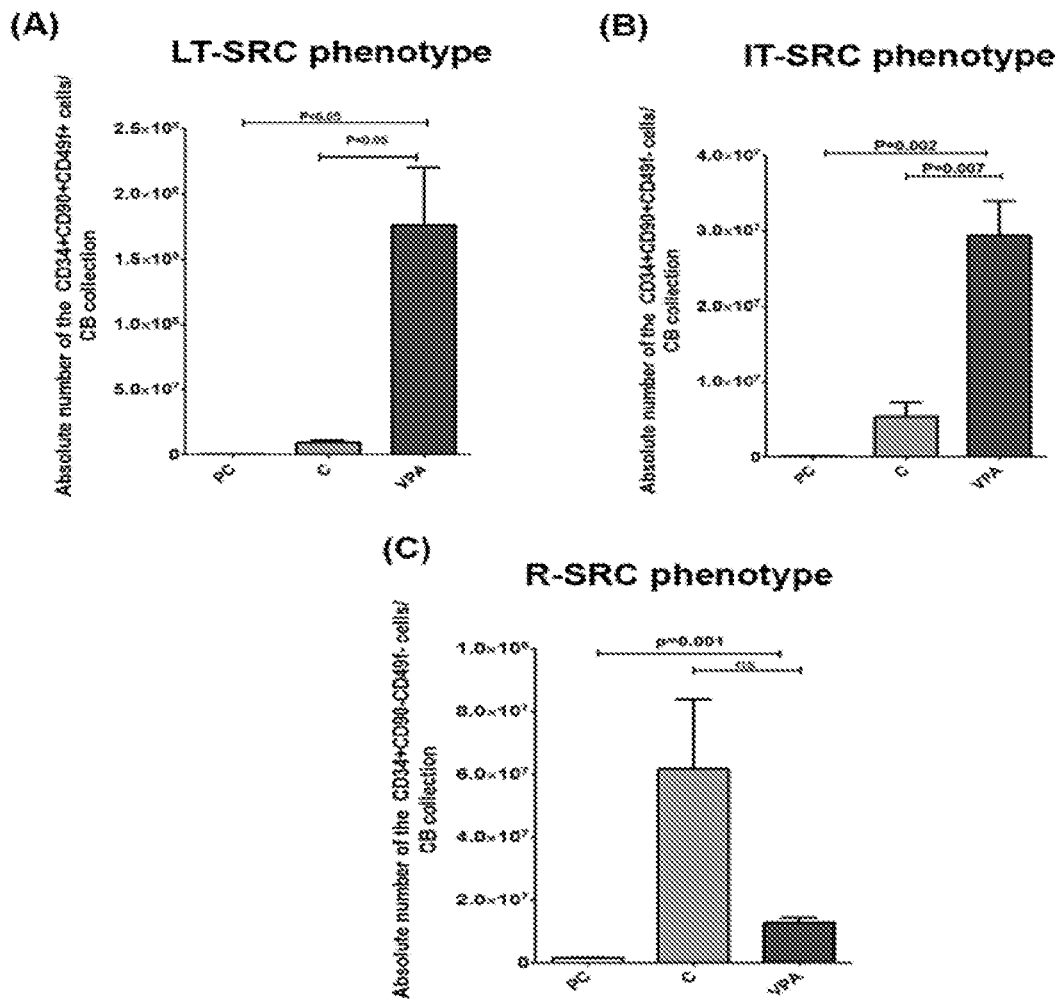
FIGs. 19A-C

ENRICHED AND EXPANDED HUMAN CORD BLOOD STEM CELLS FOR TREATMENT OF HEMATOLOGICAL DISORDERS

This application is a national stage application under 35 U.S.C. § 371 of PCT Application No. PCT/US2014/038361, filed May 16, 2014, which claims the benefit of U.S. Provisional Patent Application Ser. No. 61/825,354, filed May 20, 2013, and U.S. Provisional Patent Application Ser. No. 61/983,805, filed Apr. 24, 2014, which are hereby incorporated by reference in their entirety.

FIELD OF THE INVENTION

The present invention relates to enriched and expanded human cord blood stem cells, method of their production, and a treatment method.

BACKGROUND OF THE INVENTION

Cord blood ("CB") hematopoietic stem cells ("HSC") have numerous phenotypic and functional characteristics that distinguish them from their adult counterparts (Cairo et al., "Placental and/or Umbilical Cord Blood: An Alternative Source of Hematopoietic Stem Cells for Transplantation," *Blood* 90:4665-4678 (1997); Dahlberg et al., "Ex vivo Expansion of Human Hematopoietic Stem and Progenitor Cells," *Blood* 117:6083-6090 (2011); Delaney et al., "Cord Blood Graft Engineering," *Biol. Blood Marrow Transplant* 19(1): S74-S78 (2013); Navarrete et al., "Cord Blood Banking: A Historical Perspective," *Br. J. Haematol.* 147:236-245 (2009); Stanevsky et al., "Umbilical Cord Blood Transplantation: Pros, Cons and Beyond," *Blood Rev.* 23:199-204 (2009)). CB CD34+ cells are thought to be more primitive due to their extensive proliferative capacity, their increased ability to generate hematopoietic colonies in vitro, their capacity to produce erythroid cells, which contain fetal hemoglobins, and the ability of smaller numbers of such cells to reconstitute a myeloablated allogeneic recipient (Cairo et al., "Placental and/or Umbilical Cord Blood: An Alternative Source of Hematopoietic Stem Cells for Transplantation," *Blood* 90:4665-4678 (1997)). The use of CB cells as HSC grafts for allogeneic stem cell recipients suffering from hematological malignancies and genetic disorders has been limited to children or smaller adult recipients due to the limited number of stem cells present in a single CB collection (Cairo et al., "Placental and/or Umbilical Cord Blood: An Alternative Source of Hematopoietic Stem Cells for Transplantation," *Blood* 90:4665-4678 (1997); Navarrete et al., "Cord Blood Banking: A Historical Perspective," *Br. J. Haematol.* 147:236-245 (2009); Stanevsky et al., "Umbilical Cord Blood Transplantation: Pros, Cons and Beyond," *Blood Rev.* 23:199-204 (2009)). These limitations have resulted in an unacceptably high rate of graft failure and delayed engraftment kinetics in adult recipients (Cairo et al., "Placental and/or Umbilical Cord Blood: An Alternative Source of Hematopoietic Stem Cells for Transplantation," *Blood* 90:4665-4678 (1997); Dahlberg et al., "Ex vivo Expansion of Human Hematopoietic Stem and Progenitor Cells," *Blood* 117:6083-6090 (2011); Delaney et al., "Cord Blood Graft Engineering," *Biol. Blood Marrow Transplant* 19(1): S74-S78 (2013); Navarrete et al., "Cord Blood Banking: A Historical Perspective," *Br. J. Haematol.* 147:236-245 (2009); Stanevsky et al., "Umbilical Cord Blood Transplantation: Pros, Cons and Beyond," *Blood Rev.* 23:199-204 (2009); Barker et al., "Combined Effect of Total Nucleated Cell Dose and HLA Match on Transplantation Outcome in 1061 Cord Blood Recipients with Hematologic Malignancies," *Blood* 115:1843-1849 (2010); Delaney et al., "Strategies to Enhance Umbilical Cord Blood Stem Cell Engraftment in Adult Patients," *Expert Rev. Hematol.* 3:273-283 (2010)). Attempts to overcome these barriers have included several different strategies such as the infusion of two different CB grafts or the ex vivo expansion of CB $CD34^+$ cells using a variety of cytokine combinations that are able to promote HSC cycling and the subsequent division of these $CD34^+$ cells (2, 6-9). These initial attempts at ex vivo stem cell expansion have resulted in the generation of larger numbers of hematopoietic progenitor and precursor cells, but reduced numbers of marrow-repopulating cells. HSCs are largely quiescent cells that slowly cycle in vivo. (Giebel et al., "Primitive Human Hematopoietic Cells Give Rise to Differentially Specified Daughter Cells Upon their Initial Cell Division," *Blood* 107(5):2146-2152 (2006); Ho et al, "The Beauty of Asymmetry: Asymmetric Divisions and Self-Renewal in the Haematopoietic System," *Curr. Opin. Hematol.* 14(4):330-336 (2007); Huang et al., "Symmetry of Initial Cell Divisions Among Primitive Hematopoietic Progenitors Is Independent of Ontogenic Age and Regulatory Molecules," *Blood* 94(8):2595-2604 (1999); Srour et al., "Modulation of in vitro Proliferation Kinetics and Primitive Hematopoietic Potential of Individual Human CD34+ CD38−/lo Cells in G0," *Blood* 105(8):3109-3116 (2005)). The rapid ex vivo cycling and division of CB $CD34^+$ cells that occurs in the presence of such cytokine combinations results in HSC commitment, with the residual marrow-repopulating potential being attributed to a small fraction of stem cells that had remained quiescent or had undergone a limited number of cell divisions (10-13). More recently, mesenchymal cell-feeder layers, or a number of molecules such as immobilized notch ligand, a copper chelator, historic deacetylase inhibitors (HDACIs), all-trans retinoic acid, an aryl hydrocarbon receptor antagonist, prostaglandin E2 (PGE2), or a c-MPL agonist have been added to these cytokine combinations with the hope of expanding the number of transplantable CB HSCs (Dahlberg et al., "Ex vivo Expansion of Human Hematopoietic Stem and Progenitor Celts," *Blood* 117:6083-6090 (2011); Delaney et al., "Strategies to Enhance Umbilical Cord Blood Stem Cell Engraftment in Adult Patients," *Expert Rev. Hematol.* 3:273-283 (2010); Boitano et al., "Aryl Hydrocarbon Receptor Antagonists Promote the Expansion of Human Hematopoietic Stem Cells," *Science* 329:1345-1348 (2010); De Felice et al., "Histone Deacetylase Inhibitor Valproic Acid Enhances the Cytokine-Induced Expansion of Human Hematopoietic Stem Cells," *Cancer Res.* 65:1505-1513 (2005); Himburg et al., "Pleiotrophin Regulates the Expansion and Regeneration of Hematopoietic Stem Cells," *Nat. Med.* 16:475-482 (2010); Milhem et al., "Modification of Hematopoietic Stem Cell Fate by 5aza 2'deoxycytidine and Trichostatin A," *Blood* 103:4102-4110 (2004); Nishino et al., "Ex vivo Expansion of Human Hematopoietic Stem Cells by a Small-Molecule Agonist of c-MPL," *Exp. Hematol.* 37:1364-1377 e1364. (2009); North et al., "Prostaglandin E2 Regulates Vertebrate Haematopoietic Stem Cell Homeostasis," *Nature* 447:1007-1011 (2007)). Several of these approaches have been evaluated in clinical trials but have resulted in the generation of larger numbers of short-term, but not long-term, marrow-repopulating cells (Dahlberg et al., "Ex vivo Expansion of Human Hematopoietic Stem and Progenitor Cells," *Blood* 117:6083-6090 (2011); de Lima et al., "Transplantation of Ex vivo Expanded Cord Blood Cells Using the Copper Chelator Tetraethylenepentamine: A Phase I/II Clinical Trial," *Bone Marrow Trans-* plant 41:771-778 (2008); de Lima et al., "Cord-Blood Engraftment with Ex Vivo Mesenchymal-Cell Coculture," *N. Engl. J. Med.* 367(24):2305-2315 (2012); Delaney et al., "Notch-Mediated Expansion of Human Cord Blood Progenitor Cells Capable of Rapid Myeloid Reconstitution," *Nat. Med.* 16(2):232-236 (2010)). Alternatively, strategies to facilitate the efficiency of homing and engraftment of CB CD34+ cells are also being pursued to increase the efficacy of allogeneic CB transplantation (Goessling et al., "Prostaglandin E2 Enhances Human Cord Blood Stem Cell Xenotransplants and Shows Long-Term Safety in Preclinical Nonhuman Primate Transplant Models," *Cell Stem Cell* 8(4):445-458 (2011); Hoggatt et al., "Differential Stem and Progenitor-Cell Trafficking by Prostaglandin E2," *Nature* 495(7441):365-369 (2013); O'Leary et al., "The Role of Dipeptidyl Peptidase 4 in Hematopoiesis and Transplantation," *Curr. Opin. Hematol.* 20(4):314-319 (2013)).

An alternative approach to expand the numbers of functional CB HSCs has been proposed. This approach is based on the hypothesis that prior attempts to expand HSCs ex vivo using serum-containing (SC) media and cytokine combinations actually result in the silencing of HSC genetic programs (Dahlberg et al., "Ex vivo Expansion of Human Hematopoietic Stem and Progenitor Cells," *Blood* 117: 6083-6090 (2011); Delaney et al., "Strategies to Enhance Umbilical Cord Blood Stem Cell Engraftment in Adult Patients," *Expert Rev. Hematol.* 3:273-283 (2010); Rao et al., "Concise Review: Cord Blood Banking, Transplantation and Induced Pluripotent Stem Cell: Success and Opportunities," *Stem Cells* 30:55-60 (2012); Milhem et al., "Modification of Hematopoietic Stem Cell Fate by 5aza 2'deoxycytidine and Trichostatin A," *Blood* 103:4102-4110 (2004); Araki et al., "Expansion of Human Umbilical Cord Blood SCID-Repopulating Cells Using Chromatin-Modifying Agents," *Exp. Hematol.* 34:140-149 (2006); Araki et al., "Chromatin-Modifying Agents Permit Human Hematopoietic Stem Cells to Undergo Multiple Cell Divisions While Retaining Their Repopulating Potential," *Blood* 109:3570-3578 (2007); Azuara et al., "Chromatin Signatures of Pluripotent Cell Lines," *Nat. Cell Biol.* 8:532-538 (2006); Chaurasia et al., "Chromatin-Modifying Agents Promote the Ex vivo Production of Functional Human Erythroid Progenitor Cells," *Blood* 117:4632-4641 (2011); Delcuve et al., "Roles of Histone Deacetylases in Epigenetic Regulation: Emerging Paradigms from Studies with Inhibitors," *Clin. Epigenetics* 4(1):5 (2012); Gul et al., "Valproic Acid Increases CXCR4 Expression in Hematopoietic Stem Progenitor Cells by Chromatin Remodeling," *Stem Cells Dev.* 18:831-838 (2009)). This alternative strategy is consistent with the growing evidence that epigenetic mechanisms play important roles in determining whether an HSC undergoes symmetrical divisions and generates additional stem cells, asymmetrical divisions that at best maintain HSC numbers while generating hematopoietic progenitor cells (HPCs), or symmetrical commitment divisions that deplete HSC numbers and generate greater numbers of HPCs (Araki et al., "Expansion of Human Umbilical Cord Blood SCID-Repopulating Cells Using Chromatin-Modifying Agents," *Exp. Hematol.* 34:140-149 (2006); Araki et al., "Chromatin-Modifying Agents Permit Human Hematopoietic Stem Cells to Undergo Multiple Cell Divisions While Retaining Their Repopulating Potential," *Blood* 109:3570-3578 (2007); Asai et al., "Necdin, a p53 Target Gene, Regulates the Quiescence and Response to Genotoxic Stress of Hematopoietic Stem/Progenitor Cells," *Blood* 120(8):1601-1612 (2012); Li, "Quiescence Regulators for Hematopoietic Stem Cell," *Exp. Hematol.* 39(5):511-520 (2011); Will et al., "Satb1 Regulates the Self-Renewal of Hematopoietic Stem Cells by Promoting Quiescence and Repressing Differentiation Commitment," *Nat. Immunol.* 14(5):437-445 (2013); Wilson et al., "Hematopoietic Stem Cells Reversibly Switch from Dormancy to Self-Renewal During Homeostasis and Repair," *Cell* 135(6):1118-1129 (2008)).

The present invention is directed to overcoming these and other deficiencies in the art.

SUMMARY OF THE INVENTION

One aspect of the present invention relates to an enriched population of isolated and expanded human cord blood stem cells. The expanded stem cells express CD34+, CD90+, CD184+, CD117+, CD49f+, ALDH+, CD45RA−, and pluripotency genes SOX2, OCT4, NANOG, and ZIC3.

Another aspect of the present invention relates to a method of producing an enriched population of isolated and expanded human cord blood stem cells. This method involves providing an isolated population of human cord blood stem cells and treating the isolated population of human cord blood stem cells in a serum-free ("SF") culture system in the presence of a histone deacetylase inhibitor ("HDACI") under conditions effective to produce an enriched population of isolated and expanded human cord blood stem cells. The expanded stem cells express CD34+, CD90+, CD184+, CD117+, CD49f+, ALDH+, CD45RA−, and pluripotency genes SOX2, OCT4, NANOG, and ZIC3.

A further aspect of the present invention relates to a method of treating a subject for a hematological disorder. This method involves administering to the subject the enriched population of isolated and expanded human cord blood stem cells of the present invention to treat the hematological disorder in the subject.

In the present invention, HDACI-treated CD34+ cells under serum free culture conditions were shown to be able to generate additional CD34+ cells that possessed many features associated with primitive stem cells including increased aldehyde dehydrogenase (ALDH) activity, increased expression of CD90, c-Kit (CD117), integrin α6 (CD49f), and CXCR4 (CD184) but that lacked CD45RA expression (Notta et al., "Isolation of Single Human Hematopoietic Stem Cells Capable of Long-Term Multilineage Engraftment," *Science* 333(6039):218-221 (2011)). In addition, upregulation of a number of pluripotency genes, including SOX2, OCT4 (also known as POU5F1), NANOG, and zinc finger protein of the cerebellum family member 3 (ZIC3, also known as HIT), but not hTERT (telomerase reverse transcriptase), was associated with valproic acid (VPA) treatment (Azuara et al., "Chromatin Signatures of Pluripotent Cell Lines," *Nat. Cell Biol.* 8:532-538 (2006)). The knockdown of SOX2, OCT4, and NANOG in HDACI-treated CD34+ cells led to a dramatic reduction of CD34+ and CD34+CD90+ cell numbers. It was found that treatment with HDACIs under SF culture conditions was capable of programming dividing CB CD34+ cells so as to generate greater numbers of primitive cells, which were capable of repopulating both irradiated and secondary immune-deficient recipient mice without the development of hematological malignancies or teratomas. Limiting dilution analysis demonstrated that the number of SCUD-repopulating cells (SRCs) was 36-fold greater in VPA-treated cells as compared with that in primary CB CD34+ cells (PCs). These data indicate that epigenetic strategies that upregulate stem cell-specific transcription factors result in the preservation of the self-renewal and multilineage differentiative capacity of dividing CB HSCs.

BRIEF DESCRIPTION OF THE DRAWINGS

FIG. 1A is a schematic representation of the ex vivo expansion strategy of primary cord blood (CB) CD34+cells (PC). Freshly isolated PC were primed for 16 hr with cytokines either in serum-free (SF) or serum-containing (SC) media. Cells were then further treated under the mentioned culture conditions with or without additional cytokines in the presence/absence of histone deacetylase inhibitors (HDACI) for 7 days. The expanded cells/re-isolated CD34+ cells were used for further analyses. Individual CB PC were treated in the absence (control) or presence of valproic acid (VPA), Scriptaid (SCR) or CAY10433 (C433) for 7 days in SF media with cytokines. VPA led to the generation of a significantly greater absolute number of CD34+ cells (*p<0.05 and **p<0.005) (FIG. 1B), CD34+CD90+ cells (*p<0.05 and p<0.005) (FIG. 1C) and CD34+CD90+CD184+ cells (*p=0.0005) (FIG. 1D) per CB collection (mean±SE; FIG. 1B, FIG. 1C (ANOVA p≤0.0007) and FIG. 1D (ANOVA, p<0.0001) than other HDACIs, (n=6-7).

In FIG. 2A, the generation of CB CD34+ and CD34+CD90+ cells in the presence of cytokines occurred to a greater degree in serum-free (SF) than serum-containing (SC) cultures. A significant difference in the fold increase of CD34+ and CD34+CD90+ cells was observed in VPA containing SF cultures as compared to SC cultures. *p<0.05, p<0.005, *p<0.0005 (mean±SE; ANOVA, p<0.0001), (n=5-7). FIG. 2B shows phenotypic analysis of PC and CD34+ cells treated in SF media under control conditions or in the presence of VPA. Each cell population was analyzed for the expression of CD34, CD90, CXCR4 (CD184), CD49f and CD45RA. The co-expression of CD184, CD49f and CD45RA by CD34+CD90+ cells (box) is depicted (n=4).

FIG. 3A shows the results of SDF1 (100 ng/mL) induced migration of re-isolated CD34+ cells generated in the absence (control) or presence of VPA (7 days). A significantly greater number of VPA treated CD34+ cells migrated towards SDF1 after 16 hr and 48 hr (mean±SE, *p<0.05, 1-tailed t-test), (n=4). FIG. 3B shows homing in NSG mice of re-isolated CD34+ cells generated in the absence (control) or presence of VPA (7 days) 16 and 48 hrs after infusion (mean±SE, ****p<0.0001, *p<0.05). NSG mice recipients (n=35).

FIG. 4A shows flow cytometric cell cycle analysis of CD34+CD90+ cells following SF culture under control (upper panel—26.4%) conditions or cultures containing VPA (lower panel—82.9%) for 7 days with corresponding dot-plots showing cells in different phases of the cell cycle by BrdU pulse labeling (2.5 hr) and staining with 7AAD (G0/G1, S and G2/M). One of 3 representative experiments is shown. FIG. 4B shows the percent of CD34+CD90+ cells that were in different phases of the cell cycle. A significant increase in the number of CD34+CD90+ cells were observed in G0/G1 (*p<0.05), S (*P<0.05) and G2/M (****p<0.0001) phases in the VPA containing cultures (mean±SD; ANOVA p<0.002), (n=3).

In FIG. 5A, primary CB CD34+ cells (PC) were primed with cytokines as indicated in FIG. 1A and treated under SF culture conditions in Media alone (No Cytokines) or VPA alone (No Cytokines) without additional cytokines for 7 days. Both cultures containing Media alone (No Cytokines) and VPA alone (No Cytokines) led to a significantly greater number of CD34+ and CD34+CD90+ cells as compared with PC (****p<0.0001 and *p<0.05) (mean±SE; ANOVA, p<0.0001), (n=6). In FIG. 5B, a significant difference was observed in the fold increase of CD34+ and CD34+CD90+ cells in the SF cultures containing Media alone (No Cytokines) versus VPA alone (No Cytokines) *p<0.05, **p<0.005 (mean±SE; ANOVA, (p<0.0001), (n=6).

FIG. 7A shows the results of primary cord blood (CB) CD34+ cells (PC) treated under control conditions or with VPA for 7 days with cytokines assessed for ALDH activity. Contour plot analyses of various populations of cells, including ALDH+ CD34+ cells (left column), ALDH+ cells (middle column). The ALDH+ cells (box) were gated for co-expression of CD34 and c-kit (CD117) (right column). A greater degree of ALDH activity was observed in serum-free (SF) as compared to serum-containing (SC) control cultures (p=0.005) as well as cultures containing VPA (p=0.001). Similarly, the percent of ALDH+CD34+ and ALDH+CD34+CD117+ cells was significantly greater in SF as compared to SC cultures (p=0.001 and p=0.007, respectively). Left panel—SC cultures and right panel—SF cultures. One of 7 representative experiments is shown. As shown in FIG. 7B, a far greater number of ALDH+CD34+CD117+ cells were generated in the presence of VPA in SF cultures as compared with SC cultures (mean±SD; *p<0.05, ANOVA, p=0.009), (n=3-5).

FIG. 8A shows the results of expression of pluripotency genes in VPA treated CD34+ cells. CD34+ cells were re-isolated after treatment in the presence or absence of VPA in serum-free (SF) and serum-containing (SC) cultures. cDNA was prepared from total RNA and RT-PCR was performed. Embryonic stem (ES) cells represent a positive control for SOX2/OCT4/NANOG transcripts and a negative control for CD34 expression. Expression of pseudo-OCT4 was not detected by RT-PCR in VPA treated CD34+ cells under SF culture conditions. Lanes for Control/VPA (SF) and VPA (SC)/ES cells were run on two different gels and lanes for OCT4-Pseudogene/genuine, were run on a single gel. GAPDH-housekeeping gene, M-A 50-bp DNA ladder. One of 4 representative experiments is shown. FIG. 8B shows the quantitation of the effects of VPA on genes associated with pluripotency. CD34+ cells cultured under different conditions were isolated and processed as described above (FIG. 8A). Relative transcript levels of genes (SOX2/OCT4/NANOG) were calculated by Sybr Green Q-PCR. The fold change of mRNA expression by CD34+ cells re-isolated from control cultures (left panel) and VPA containing cultures (right panel) was calculated by normalizing to the level of corresponding transcripts present in PC (mean±SD; ANOVA, p=0.0001), (n=4). FIG. 8C shows the quantitation of expression of genes associated with chromatin remodeling and pluripotency after VPA treatment under SF or SC culture conditions. Fold change of mRNA expression levels of SET, MYST3, SMARCAD1 and ZIC3 genes were calculated as described above (mean±SE, ANOVA, p=0.04), (n=3).

FIG. 9A shows the results of a representative flow cytometric analysis of SOX2, OCT4 and NANOG expression in re-isolated CD34+ cells after 7 days of culture under control conditions or after exposure to VPA. Cells were fixed, permeabilized, and stained with matched isotype IgG (left-most curve in each panel) or SOX2/OCT4/NANOG mAbs to assess the intracellular levels of protein in re-isolated CD34+ cells from control (right-most curve in control panels) and VPA (right-most curve in VPA panels) cultures. One of 4 representative experiments is shown. FIG. 9B shows the results of confocal microscopic analysis of pluripotency gene expression: CD34+ cells were re-isolated after treatment with VPA in SF cultures and immunostained with isotype-matched IgG, or OCT4/SOX2/NANOG and ZIC3 antibodies (FITC) as described in the Examples. The nuclei were stained with DAPI. A single optical section of confocal z-series (scale bar=10 μm, OCT4, SOX2, and NANOG (63×) and IgG, ZIC3 and higher magnification of OCT4 (126×) is shown. One of 3 representative experiments is shown. FIG. 9C shows the results of co-immunoprecipitation of pluripotency genes. ES (H9) cells and the progeny of the VPA treated cells (V) were lysed on day 7, ES or V cell lysates were immunoprecipitated (IP) with a NANOG pAb (or anti-IgG control) and fractionated by SDS-PAGE. Total protein lysates (input) from ES and VPA treated cells were also included in the same gel but were noncontiguous and Western blot analysis (WB) was performed using an OCT4 pAb. WB using NANOG mAb were also performed with ES and V lysates. b-ACTIN is a loading control. One of 3 representative experiments is shown.

In FIG. 10A, primary CB CD34+ cells (PC) were treated with VPA in serum-free (SF) cultures. After 3 days, cells were transfected with a pool of SOX2, OCT4, and NANOG (SON), scrambled (negative control) and GAPDH siRNA (positive control) as described in the Examples. SOX2, OCT4, NANOG, GAPDH, and ZIC3 transcripts were quantitated by Sybr Green Q-PCR and normalized to the level of CD34 transcripts $*p<0.05$, $p\leq0.006$, $*p=0.0001$ (mean±SE; ANOVA, p<0.0001), (n=3). In FIG. 10B, expression of SOX2/OCT4/NANOG, CD34 and GAPDH following siRNA-mediated knockdown were analyzed by RT-PCR. M-DNA markers, Embryonic stem (ES) cells represent a positive control for SOX2, OCT4, NANOG, and ZIC3. Lanes were run on the same gel. In FIG. 10C, pluripotency gene expression was analyzed by confocal microscopy. Upper panel: scrambled siRNA and Lower panel: SON siRNA showing SOX2, OCT4, NANOG, and ZIC3 expression in cells treated with VPA. Images represent an optical section of confocal z-series; scale bar=10 μm (40×). Similar data were obtained in two additional experiments. In FIG. 10D, after 7 days of transfection, the percent of cells that were CD34+ and CD34+CD90+ was analyzed using flow cytometry. The graph represents a comparative analysis of the percent of CD34+ and CD34+CD90+ cells generated in VPA cultures after transfection with siRNA including Scrambled and SON. $*p<0.05$ (mean±SE; ANOVA, p=0.0005), (n=3). FIG. 10E shows absolute numbers of CD34+ and CD34+CD90+ cells/CB collection generated in VPA containing cultures following transfection with Scrambled or SON siRNA were calculated. $*p<0.05$, $***p=0.0001$ (mean±SE; ANOVA, p=0.0008), (n=3).

In FIG. 11F, a comparative analysis of the degree of mean human cell chimerism achieved with transplantation of PC, CD34+ cells treated in the absence or presence of cytokines under SF culture conditions with or without VPA. (FIG. 11A) $p=0.006$, $*p=0.0008$ (ANOVA p<0.0001), (FIG. 11B) $**p=0.004$ (ANOVA, p=0.03), (FIG. 11C) $*p=0.01$, $p=0.0008$ (ANOVA, p=0.01), (FIG. 11D) $p=0.003$, $****p<0.0001$ (ANOVA, p<0.0001) and (FIG. 11E) median±SD $*p<0.05$, $**p<0.005$, (ANOVA, p<0.0001) and (FIG. 11F) $*p<0.05$ (1-tailed t-test), $**p\leq0.002$ (ANONA<0.0001). NSG recipients (n=27).

In FIG. 13A, increasing numbers of PC (50, 250, 500, 2500, and 5000) and the progeny of cultures initiated with an equivalent number of cells cultured under control conditions or in the presence of VPA were individually transplanted into NSG mice. The percent of human CD45+ cell engraftment in the BM of recipient mice after 12-13 weeks are shown. In FIG. 13B, a Poisson statistical analysis was performed using the number of mice with or without evidence of human cell engraftment (Table 3). The graph represents the percent of mice without human cell chimerism (negative) following the transplantation of PC or the progeny of equivalent numbers of CD34+ cells from control cultures or cultures containing VPA. The dotted lines represent the 95% confidence intervals. In FIG. 13C, SRC numbers were calculated using Poisson statistical analysis and represented as the number of SRC/1×10$^6$ CD34+ cells **P≤0.002 (ANOVA, p=0.003), NSG mice recipients (n=111).

(FIG. 17A and FIG. 17B). Only ES (H9) cells formed teratomas in each of the three mice (left panel), (FIG. 17C) neither control nor VPA treated CD34+ cells formed teratomas (right panel), (FIG. 17D). A photomicrograph of the stained section showing three different germ layers (small arrow head—Ectoderm, solid arrow—Mesoderm and broken arrow—Endoderm) (4×), (FIG. 17E) mesoderm (cartilage) (4×), (FIG. 17F) pigmented ectoderm (20×), and (FIG. 17G) endoderm (20×). 3 mice were utilized per group including ES (H9), Control and VPA (n=9 mice).

FIGS. 19A-C show the VPA expanded HSC product contains all classes of HSCs as defined by phenotype. VPA expanded CD34+ cells were analyzed for CD34+CD90−CD49f− rapid (R-SRC), CD34+CD90+CD49f− intermediate (IT-SRC), and CD34+CD90+CD49+ long (LT-SRC) (n=3).

DETAILED DESCRIPTION OF THE INVENTION

Figure 1A:
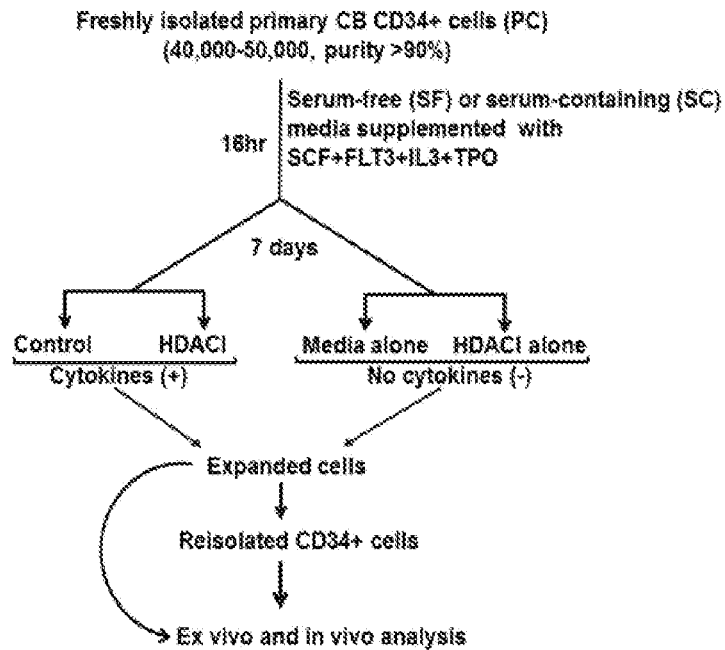
FIGS. 1A-D show the effect of HDACIs on the ex vivo expansion of CB CD34+, CD34+CD90+ and CD34+CD90+ CD184+ cells.

The present invention relates to an enriched population of isolated and expanded stem cells derived from human cord blood, their ex vivo expansion, and treatment methods that involve administering the enriched population of isolated and expanded stem cells to a subject. According to the present invention, it is possible to expand hematopoietic stem cells by culturing hematopoietic stem cells ex vivo in a serum-free medium and in the presence of a histone deacetylase inhibitor to achieve a unique population of stem cells that express a particular phenotype.

According to one aspect, the present invention relates to an enriched population of isolated and expanded human cord blood stem cells. The expanded stem cells are CD34+, CD90+, CD184+, CD49f+, CD117+, ALDH+, but meagerly express CD45RA (i.e., are CD45RA−), and express pluripotency genes SOX2, OCT4, NANOG, and ZIC3.

Hematopoietic stem cells are multi- or pluripotent cells, which allows them to differentiate into blood cells of all lineages and the ability to regenerate themselves while maintaining their multi- or pluripotency.

The enriched and expanded stem cells of the present invention are isolated from a human and are derived from human cord blood.

The stem cells of the enriched population of the present invention are CD34+, CD90+, CD184+, CD49f+, CD117+, and CD45RA−. CD34+, CD90+, CD184+, CD49f+, CD117+, means expressing (+) CD (cluster of differentiation) 34, 90, 184, 49f, and 117 antigen on the cell surface. These antigens are markers for hematopoietic stem cells. CD45RA− means not (or meagerly) expressing antigen CD45RA on the cell surface. The stem cell populations of the present invention are enriched for stem cell markers CD34+, CD90+, CD184+, CD49f+, CD117+, and CD45RA− and express pluripotency genes SOX2, OCT4, NANOG, and ZIC3.

Experimental procedures for testing for the presence of human hematopoietic stem cells which have bone marrow repopulating ability can be carried out, e.g., by using NOD/SCID mice obtained by crossing diabetic mice and immunodeficient mice. The cells detected by this assay are called SCID-repopulating cells (SRC) and are considered the closest to human hematopoietic stem cells.

The stem cells in the population of stem cells of the present invention are referred to as expanded stem cells, which means that the number of hematopoietic stem cells after culturing is greater than that before culturing, or put another way, the number of stem cells after culturing is greater than the number of cells taken from a cord blood sample.

In one embodiment, the enriched population of stem cells of the present invention is a stem cell population containing only or mostly hematopoietic stem cells resulting from self-renewal of hematopoietic stem cells from a cord blood isolate. Hematopoietic progenitor cells differentiated from the isolated hematopoietic stem cells or a cell population containing both hematopoietic stem cells and hematopoietic progenitor cells may also be present in the enriched population. However, in one embodiment, the number of hematopoietic progenitor cells in the enriched population is less than the number of hematopoietic stem cells. For example, in experimental results, VPA-treated cells after 7 days contained predominately CD34+CD90+ (74.2±9.8%) cells with remaining cells Glycophorin+ (17.0±5.4%), CD41+ (8.9±2.0%), CD14+ (3.9±1.5%) with virtually no T Cells (CD3—0.2±0.3%) and B Cells (CD19—0.5±0.1%). Expanded grafts were composed of a homogenous population of primitive small immature mononuclear cells with an agranular cytoplasm and prominent nucleoli.

In one embodiment, the enriched population comprises a homogenous population of primitive small immature mononuclear cells with an agranular cytoplasm and prominent nucleoli.

Expansion of hematopoietic stem cells further means the differentiation of hematopoietic stem cells to increase the absolute number of hematopoietic stem cells having the above-mentioned phenotypes. In one embodiment, at least about 16%, 17%, 18%, 19%, 20%, 21%, 22%, 23%, 24%, 25%, or 26% of the stem cells in the enriched population are in the G2/M phase. Alternatively, about 18.0%±1.2% or about 17-19% of the stem cells in the enriched population are in the G2/M phase. In another embodiment, at least about 4%, 5%, 6%, 7%, 8%, 9%, 10%, 11%, 12%, 13%, 14%, 15%, 16%, 17%, 18%, 19%, 20%, 21%, 22%, 23%, 24%, 25%, 26%, 27%, 28%, 29%, 30%, 31%, 32%, 33%, 34%, 35%, 36%, or 37% of the stem cells in the enriched population are in G0/G1 phase. Alternatively, about 23.2%±13.8% or about 20-26% of the stem cells in the enriched population are in the G0/G1 phase.

The stem cells of the enriched population of the present invention have the additional characteristic of expressing the pluripotency genes SOX2, OCT4, NANOG, and ZIC3. In one embodiment, at least about 75%, 80%, 85%, 90%, 95%, 96%, 97%, 98%, or 99% of the stem cells in the enriched population express the pluripotency genes SOX2, OCT4, NANOG, and ZIC3.

According to one embodiment, the stem cells of the enriched population of stem cells do not shown any upregulation in the expression level of embryonic stem cell pluripotency gene hTERT.

In one embodiment, the stem cells in the enriched population of the present invention are positive for aldehyde dehydrogenase activity. Specifically, at least about 50%, 55%, 60%, 65%, 70%, 75%, 80%, or more of the stem cells in the enriched population of the present invention are positive for aldehyde dehydrogenase activity.

The enriched population of stem cells of the present invention may be in contact with a cytokine selected from the group consisting of SCF, Flt3, TPO, IL3, and combinations of these cytokines.

In addition, the stem cells of the enriched population may be in contact with a histone deacetylase inhibitor. Suitable histone deacetylase inhibitors include, without limitation, VPA, SCR, LBH589, TSA, SAHA, Cay 10433 (C433) also known as BML-210, and Cay10298.

Stem cells in the enriched and expanded population of the present invention have reduced expression of HDAC1, HDAC3, and HDAC5 compared to isolated and expanded human cord blood stem cells that are not in contact with a histone deacetylase inhibitor.

The enriched population of stem cells of the present invention is T cell and B cell depleted. For example, in one embodiment of the present invention, the enriched population contains predominantly CD34+CD90+, CD41+, and CD14+ cells with virtually no T cells and B cells. For example, the enriched population may contain about 64-84% CD34+CD90+ cells, about 12-23% glycophorin (GPA)+ cells, about 7-11% CD41+ cells, about 2.5-5.5% CD14+ cells, about 0-0.5% T-cells (CD19+), and 0.4-0.6% B-cells (CD3+). In one embodiment, the expanded stem cells are nearly depleted of T cells and B cells and contain a limited number of monocytes (CD14).

According to one embodiment, the enriched population of stem cells of the present invention contain the following phenotypic markers: about 64-84%, 65-83%, 66-82%, 67-81%, 68-80%, 69-79%, 70-78%, 71-77%, 72-76%, 73-75%, or 74% CD34+CD90+ cells; about 12-23%, 13-22%, 14-21%, 15-20%, 16-19%, or 17-18% glycophorin (GPA)+ cells; about 7-11%, 8-10%, or 9% CD41+ cells; about 2.5-5.5%, 3-5%, or 4% CD14+ cells; about 0-0.5% CD19+ cells; and about 0.4-0.6% CD3+ cells after about 7 days of culture in the presence of an HDACI.

Stem cells in the enriched and expanded population of the present invention may be cryopreserved for future use. Cryopreservation methods are discussed in Berz et al., "Cryopreservation of Hematopoietic Stem Cells," *Am. J. Hematol.* 82(6):463-472 (2007), which is hereby incorporated by reference in its entirety.

Another aspect of the present invention relates to a method of producing an enriched population of isolated and expanded human cord blood stem cells. This method involves providing an isolated population of human cord blood stem cells and treating the isolated population of human cord blood stem cells in a serum-free culture system in the presence of a histone deacetylase inhibitor under conditions effective to produce an enriched population of isolated and expanded human cord blood stem cells. The expanded human cord blood stem cells are CD34+, CD90+, CD184+, CD117+, CD49f+, ALDH+, CD45RA− and express pluripotency genes SOX2, OCT4, NANOG, and ZIC3.

In one embodiment of this aspect of the present invention, treating the isolated population of human cord blood stem cells in the serum-free culture system and in the presence of a histone deacetylase inhibitor is carried out to increase the absolute number of stem cells. For example, the method may be carried out to expand the absolute number of stem cells (CD34+CD90+) by about $2.0 \times 10^4$ fold.

The stem cells in the enriched population of isolated and expanded stem cells obtained by the method of the present invention possess the characteristics of the enriched population of expanded stem cells described supra.

In carrying out the method of the present invention, the culture system may include a culture vessel generally used for animal cell culture such as a Petri dish, a flask, a plastic bag, a Teflon™ bag, which may or may not have a preliminary coating with an extracellular matrix or a cell adhesion molecule. When used, the materials for such a coating may be collagens I to XIX, fibronectin, vitronectin, laminins 1 to 12, nitogen, tenascin, thrombospondin, von Willebrand factor, osteoponin, fibrinogen, various types of elastin, various types of proteoglycan, various types of cadherin, desmocolin, desmoglein, various types of integrin, E-selectin, P-selectin, L-selectin, immunoglobulin superfamily, Matrigel, poly-D-lysine, poly-L-lysine, chitin, chitosan, Sepharose, alginic acid gel, and/or hydrogel or a fragment thereof. Such a coating material may be a recombinant material having an artificially modified amino acid sequence. The hematopoietic stem cells may be cultured by using a bioreactor which can mechanically control the medium composition, pH, and the like and obtain high density culture (see Schwartz, "Rapid Medium Perfusion Rate Significantly Increases the Productivity and Longevity of Human Bone Marrow Cultures," *Proc. Natl. Acad. Sci. U.S.A.,* 88:6760 (1991); Koller, "Clinical-scale Human Umbilical Cord Blood Cell Expansion In a Novel Automated Perfusion Culture System," *Bone Marrow Transplant* 21:653 (1998); Koller, "Large-scale Expansion of Human Stem and Progenitor Cells from Bone Marrow Mononuclear Cells in Continuous Perfusion Cultures," *Blood* 82:378 (1993), which are hereby incorporated by reference in its entirety).

While the culture system is serum-free, various nutrients may be used to provide adequate growth and expansion conditions for the stem cells. Suitable nutrient mediums include, but are not limited to, Dulbecco's Modified Eagles' Medium (DMEM), Ham's Nutrient Mixture F12, McCoy's 5A medium, Eagles' Minimum Essential Medium (EMEM), αMEM medium (alpha Modified Eagles' Minimum Essential Medium), RPMI1640 medium, Iscove's Modified Dulbecco's Medium (IMDM), StemPro34 (Invitrogen), X-VIVO 10 (Cambrex), X-VIVO 15 (Cambrex), HPGM (Cambrex), StemSpan H3000 (Stemcell Technologies), StemSpan SFEM (Stemcell Technologies), Stemline II (Sigma-Aldrich), or QBSF-60 (Quality Biological).

Suitable mediums for culture may contain sodium, potassium, calcium, magnesium, phosphorus, chlorine, amino acids, vitamins, cytokines, hormones, antibiotics, serum, fatty acids, saccharides, or the like. In the culture, other chemical components or biological components may be incorporated singly or in combination, as the case requires. Such components to be added in the medium may include insulin, transfferin, lactoferrin, cholesterol, ethanolamine, sodium selenite, monothioglycerol, 2-mercaptoethanol, sodium pyruvate, polyethylene glycol, various vitamins, various amino acids, agar, agarose, collagen, methylcellulose, various cytokines, various growth factors, or the like. Suitable cytokines may include, without limitation, interleukin-1 (IL-1), interleukin-2 (IL-2), interleukin-3 (IL-3), interleukin-4 (IL-4), interleukin-5 (IL-5), interleukin-6 (IL-6), interleukin-7 (IL-7), interleukin-8 (IL-8), interleukin-9 (IL-9), interleukin-10 (IL-10), interleukin-11 (IL-11), interleukin-12 (IL-12), interleukin-13 (IL-13), interleukin-14 (IL-14), interleukin-15 (IL-15), interleukin-18 (IL-18), interleukin-21 (IL-21), interferon-α (IFN-α), interferon-β (IFN-β), interferon-γ (IFN-γ), granulocyte colony stimulating factor (G-CSF), monocyte colony stimulating factor (M-CSF), granulocyte-macrophage colony stimulating factor (GM-CSF), stem cell factor (SCF), flk2/flt3 ligand (FL), leukemia inhibitory factor (LIF), oncostatin M (OM), erythropoietin (EPO), and thrombopoietin (TPO).

Specifically suitable cytokines include SCF, Flt3, TPO, IL-3, and combinations thereof.

Suitable growth factors to be added to the culture system may include, without limitation, transforming growth factor-β (TGF-β), macrophage inflammatory protein-1α (MIP-1α), epidermal growth factor (EGF), fibroblast growth factor (FGF), nerve growth factor (NGF), hepatocyte growth factor (HGF), protease nexin I, protease nexin II, platelet-derived growth factor (PDGF), cholinergic differentiation factor (CDF), chemokines, Notch ligand (such as Delta 1), Wnt protein, angiopoietin-like protein 2, 3, 5 or 7 (Angpt 2, 3, 5 or 7), insulin-like growth factor (IGF), insulin-like growth factor binding protein (IGFBP), and Pleiotrophin.

In addition, recombinant cytokines or growth factors having an artificially modified amino acid sequence may be included in the culture system and may include, for example and without limitation, IL-6/soluble IL-6 receptor complex and Hyper IL-6 (IL-6/soluble IL-6 receptor fusion protein).

In one embodiment, cytokines and growth factors may be added to the culture system at a concentration of about 0.1 ng/mL to 1000 ng/mL, preferably from 1 ng/mL to 100 ng/mL.

In culturing the stem cells according to the method of this aspect of the present invention, supplements or treating agents may be added to the culture system directly or, e.g., immobilized onto the surface of the substrate or support used for the culture. This may occur by dissolving a component to be used in an appropriate solvent, coating the substrate or support with the resulting solution, and then washing away an excess of the component.

When a specific component is added to the culture system, it may first be dissolved in an appropriate solvent and added to the medium so that the concentration of the compound will be from about 100 nM to 10 mM, or from about 300 nM to 300 μM, or from about 1 μM to 100 μM, or from about 3 μM to 30 μM. Examples of suitable solvents include, without limitation, dimethyl sulfoxide (DMSO) and various alcohols.

In one embodiment, the hematopoietic stem cells are treated in the culture system at a temperature of from about 25 to 39° C., or from about 33 to 39° C., in an atmosphere having a $CO_2$ concentration of from about 4 to 10 vol %, or from about 4 to 6 vol %, usually for a period of about 7 days.

Stem cells treated according to the method of this aspect of the present invention are treated in the presence of a histone deacetylase inhibitor, examples of which are described supra.

Hematopoietic stem cells expanded by the method of the present invention can be used as a cell transplant. Thus, a further aspect of the present invention relates to a method of treating a subject for a hematological disorder. This method involves administering to the subject the enriched population of isolated and expanded human cord blood stem cells of the present invention to treat the hematological disorder in the subject.

Because hematopoietic stem cells can differentiate into blood cells of all lineages, they may be transplanted after differentiation into a certain type of blood cell ex vivo. Hematopoietic stem cells expanded by the method of the present invention may be transplanted as they are, or after enrichment using a cell surface antigen as an index, for example, by a magnetic bead method or by a cell sorting method. The expanded hematopoietic stem cells may be transplanted to its donor (autologous) or another individual (allogeneic).

The enriched and expanded hematopoietic stem cells of the present invention can be used as a graft for hematopoietic stem cell therapy as a substitute for conventional bone marrow or cord blood transplantation. The transplantation of hematopoietic stem cells of the present invention is carried out in the same manner as conventional bone marrow or cord blood transplantation. The graft to may be a composition containing a buffer solution, an antibiotic, a pharmaceutical compound, and the enriched and expanded hematopoietic stem cells.

The method of this aspect of the present invention is carried out to treat a subject for a hematological disorder. Thus, the method is suitable to treat not only various types of leukemia but also various diseases. For example, in a case of treatment of a solid cancer patient by chemotherapy or radiotherapy which may cause myelosuppression as a side effect, the patient can recover from hematopoietic damage quickly if administered to the patient after the treatment. Thus, a more intense chemotherapy becomes available with an improved therapeutic effect.

The treatment method of the present invention may also be carried out to alleviate a deficiency in a certain type of blood cell in a patient by differentiating hematopoietic stem cells into a particular type of blood cell and returning them into the patient.

The treatment method of the present invention may be carried out to treat diseases associated with a decrease in hematopoietic cells and/or hematopoietic insufficiency, diseases accompanying increase in hematopoietic cells, diseases accompanying hematopoietic dysfunction, decrease in immunocytes, increase in immunocytes, diseases accompanying autoimmunity or immune dysfunction, diseases associated with nerve damage, diseases accompanying muscle damage, and/or ischemic diseases.

Specific examples of diseases or disorders amenable to treatment pursuant to this method of the present invention include, without limitation, chronic granulomatosis, severe combined immunodeficiency syndrome, adenosine deaminase (ADA) deficiency, agammaglobulinemia, Wiskott-Aldrich syndrome, Chediak-Higashi syndrome, immunodeficiency syndrome such as acquired immunodeficiency syndrome (AIDS), C3 deficiency, congenital anemia such as thalassemia, hemolytic anemia due to enzyme deficiency and sicklemia, lysosomal storage disease such as Gaucher's disease and mucopolysaccharidosis, adrenoleukodystrophy, various kinds of cancers and tumors, especially blood cancers such as acute or chronic leukemia, Fanconi syndrome, aplastic anemia, gramulocytopenia, lymphopenia, thrombocytopenia, idiopathic thrombocytopenic purpura, thrombotic thrombocytopenic purpura, Kasabach-Merritt syndrome, malignant lymphoma, Hodgkin's disease, multiple myeloma, chronic hepatopathy, renal failure, massive blood transfusion of bank blood or during operation, hepatitis B, hepatitis C, severe infections, systemic lupus erythematodes, articular rheumatism, xerodermosteosis, systemic sclerosis, polymyositis, dermatomyositis, mixed connective tissue disease, polyarteritis nodosa, Hashimoto's disease, Basedow's disease, myasthenia gravis, insulin dependent diabetes mellitus, autoimmune hemolytic anemia, snake bite, hemolytic uremic syndrome, hypersplenism, bleeding, Bernard-Soulier syndrome, Glanzmann's thrombasthenia, uremia, myelodysplastic syndrome, polycythemia rubra vera, erythremia, essential thrombocythemia, myeloproliferative disease, traumatic spinal cord injury, nerve injury, neurotmesis, skeletal muscle injury, scarring, diabetes mellitus, cerebral infarction, myocardial infarction, and obstructive arteriosclerosis.

The treatment method of the present invention may be carried out to mitigate against the ill effects of exposure, or over-exposure to radiation, including Acute Radiation Syndrome (ARS).

In another embodiment of the treatment method of the present invention, the enriched and expanded hematopoietic stem cells of the present invention are used for gene therapy. In the gene therapy, a therapeutic gene is transfected into hematopoietic stem cells, and the resulting transfected cells (i.e., transformed hematopoietic stem cells) are transplanted into a patient. The therapeutic gene to be transfected may include, without limitation, genes for hormones, cytokines, receptors, enzymes, polypeptides, and the like according to the disease being treated. Specific examples of a suitable therapeutic gene include, without limitation, genes for insulin, amylase, proteases, lipases, trypsinogen, chymotrypsinogen, carboxypeptidases, ribonucleases, deoxyribonucleases, phospholipase A2, esterases, α1-antitrypsin, blood coagulation factors (VII, VIII, IX and the like), protein C, protein S, antithrombin, UDP glucuronyl transferase, ornithine transcarbanoylase, hemoglobin, NADPH oxidase, glucocerebrosidase, α-galactosidase, α-glucosidase, α-iduronidase, cytochrome P450 enzymes, adenosine deaminase, Bruton kinase, complements C1 to C4, JAK3, common cytokine receptor γ chain, ataxia telangiectasia mutated (ATM), cystic fibrosis (CF), myocilin, thymic humoral factor, thymopoietin, gastrin, selectins, cholecystokinin, serotinin, substance P, major histocompatibility complex (MHC), and multiple drug resistance factor (MDR-1).

In addition, RNA genes suppressing expression of disease genes can be effective as therapeutic genes and can be used in the method of the present invention. For example, anti-sense RNA, siRNA, shRNA, decoy RNA, and ribozymes.

For transfer of a therapeutic gene into hematopoietic stem cells, ordinary gene transfer methods for animal cells, including vectors for animal cells such as retrovirus vectors like murine stem cell vector (MSCV) and Moloney murine leukemia virus (MmoLV), adenovirus vectors, adeno-associated virus (AAV) vectors, herpes simplex virus vectors, and lentivirus vectors may be used (see Verma, "Gene Therapy: Promises, Problems and Prospects," *Nature* 389: 239 (1997), which is hereby incorporated by reference in its entirety). Alternatively, calcium phosphate coprecipitation, DEAE-dextran transfection, electroporation, a liposome method, lipofection, microinjection, or the like may be used. Among these procedures, retrovirus vectors, adeno-associated virus vectors, or lentivirus vectors are often preferred because their integration into the chromosomal DNA is expected to allow eternal expression of the gene.

In one embodiment, an adeno-associated virus (AAV) vector is prepared as follows. Cells are first transfected with a vector plasmid obtained by inserting a therapeutic gene between the ITRs (inverted terminal repeats) at both ends of wild-type adeno-associated virus DNA and a helper plasmid for supplementing virus proteins and subsequently infected with an adenovirus as a helper virus to induce production of virus particles containing AAV vectors. Instead of the adenovirus, a plasmid for expression of an adenovirus gene which functions as a helper may be transfected. Next, hematopoietic stem cells are infected with the virus particles. It is preferred to insert an appropriate promoter, enhancer, insulator or the like upstream of the target gene in the vector DNA to regulate expression of the gene. Introduction of a marker gene such as a drug resistance gene in addition to the therapeutic gene makes it easy to select cells carrying the therapeutic gene. The therapeutic gene may be a sense gene or an antisense gene.

When hematopoietic stem cells of the present invention are transfected with a therapeutic gene for use in the therapeutic method of the present invention, the cells are cultured by an appropriate method, as discussed supra, for expansion of hematopoietic stem cells. The gene transfer efficiency can be evaluated by standard methods in the art. It is possible to transfect a gene into hematopoietic stem cells, expand the resulting cells (transformed hematopoietic stem cells) by the above-mentioned method of expanding hematopoietic stem cells, and use the resulting transformed hematopoietic stem cells for administering to a subject in a method of gene therapy.

The transplant for gene therapy may be a composition containing a buffer solution, an antibiotic, a pharmaceutical, and the transformed hematopoietic stem cells.

Suitable diseases that can be treated by gene therapy according to the method of the present invention include, without limitation, chronic granulomatosis, severe combined immunodeficiency syndrome, adenosine deaminase (ADA) deficiency, agammaglobulinemia, Wiskott-Aldrich syndrome, Chediak-Higashi syndrome, immunodeficiency syndrome such as acquired immunodeficiency syndrome (AIDS), hepatitis B, hepatitis C, congenital anemia such as thalassemia, hemolytic anemia due to enzyme deficiency, Fanconi's anemia and sicklemia, lysosomal storage disease such as Gaucher's disease and mucopolysaccharidosis, adrenoleukodystrophy, and various kinds of cancers and tumors.

Another aspect of the present invention relates to a method of determining the effects of a compound on hematopoietic stem cells. This method involves providing an enriched population of isolated and expanded human cord blood stem cells, where the stem cells are CD34+, CD90+, CD184+, CD49f+, CD117+, ALDH+, CD45RA− and express pluripotency genes SOX2, OCT4, NANOG, and ZIC3, and contacting the stem cells with a compound to be tested. The stem cells are then analyzed after contact with the compound to determine the effect of the compound on the stem cells.

In one embodiment, the stem cells are analyzed for cell surface markers, their expression of pluripotency genes, whether the cells are living and/or dividing, and/or whether or not the compound is lethal to the cells.

EXAMPLES

The following examples are provided to illustrate embodiments of the present invention but are by no means intended to limit its scope.

Example 1

Epigenetic Reprogramming Induces the Expansion of Cord Blood Stem Cells

Methods

Isolation of CB CD34+ Cells and their Ex Vivo Culture

CB collections were purchased from the Placental Blood Program at the New York Blood Center. CB-MNCs were isolated by Ficoll-Hypaque density centrifugation, and CD34+ cells were purified by immunotnagnetic selection as previously described (Chaurasia et al., "Chromatin-Modifying Agents Promote the Ex vivo Production of Functional Human Erythroid Progenitor Cells," *Blood* 117:4632-4641 (2011), which is hereby incorporated by reference in its entirety). Highly purified (90%-98%) PCs ($4.0$-$5.0 \times 10^4$) were cultured in SF Stemline II (Sigma-Aldrich) culture medium or IMDM (Lonza) containing 30% FBS (HyClone Laboratories) supplemented with 150 ng/ml SCF, 100 ng/ml fms-like tyrosine kinase receptor 3 (FLT3 ligand), 100 ng/ml thrombopoietin (TPO), and 50 ng/ml interleukin 3 (IL-3) (R&D Systems) and incubated in a humidified incubator maintained at 37° C. with 5% $CO_2$. After 16 hours of incubation, the cells were exposed to varying concentrations of individual HDACIs including trichostatin A (TSA), suberoylanifide hydroxamic acid (SAHA), VPA (Sigma-Aldrich), SCR, and CAY1.0433 (C433, also termed BML-210), CAY10398 (also known as MD85), and CAY10603 (molecular formula: $C_{22}H_{30}N_4O_6$) (Cayman Chemicals), either in the absence or continued presence of cytokines for an additional 7 days (FIG. 1A). The cell populations studied and the various conditions under which they were cultured are referred to by specific terms listed in Table 1.

TABLE 1

Terminology Used to Refer to the Cell Populations Studied

| Condition | Terminology |
|---|---|
| PC | Primary uncultured CB CD34+ Cells |
| Control | Cultures supplemented with cytokines for 7 days |
| VPA | Cultures supplemented with cytokines and VPA for 7 days |
| Media alone (no cytokines) | Cultures supplemented with SF media for 7 days in the absence of cytokines of VPA |
| VPA alone (no cytokines) | Cultures supplemented with SF media for 7 days in the absence of added cytokines but in the presence of VPA |

Viable PC and cultured cells were enumerated using the trypan blue exclusion method. The fold expansion of CD34+ cells or subpopulations was calculated based on the number of CD34+ cells determined to be present in an individual CB collection and the number of CD34+ cells that would have been generated if all of the CD34+ cells within that primary CB collection were cultured using the various culture conditions described.

Phenotypic Analysis

PC or cultured cells expanded in the presence or absence of HDACIs were stained with an anti-human CD34 mAb or an isotype-matched control mAb and analyzed using a FACSCanto II (BD). CD34+ cells were re-isolated using a CD34+ cell isolation kit, as previously described, for further phenotypic and functional analyses. All mAbs were purchased from BD Biosciences and Cell Signaling Technology. Phenotypic analyses (CD34APC, CD90-FITC, CD184-PE, CD117-PE, CD49f–PE, and CD45RA PECy7) of the ex vivo—expanded cells after 7 days in control cultures or cytokines plus an HDACI were performed as previously described (Chaurasia et al., "Chromatin-Modifying Agents Promote the Ex vivo Production of Functional Human Erythroid Progenitor Cells," *Blood* 117:4632-4641 (2011), which is hereby incorporated by reference in its entirety).

Migration Assay

The migratory behavior of CB CD34+ cells was evaluated as previously described using 6.5 mm diameter, 5 µm pore Transwell plates (Costar) (Shivtiel et al., "CD45 Regulates Homing and Engraftment of Immature Normal and Leukemic Human Cells in Transplanted immunodeficient Mice," *Exp. Hematol.* 39(12):1161-1170 (2011), which is hereby incorporated by reference in its entirety). The lower compartments of the Transwells were filled with StemLine II SF medium supplemented with 100 ng/ml of stromal-derived factor 1 (SDF1) (R&D Systems). The Transwell filters were coated with Matrigel for 30 minutes at 37° C. Re-isolated CD34+ cells ($1 \times 10^5$) from the control and VPA-containing cultures were plated on the Matrigel-coated filters in 100 µl of Stemline II media. After 16 and 48 hours, cells that migrated to the lower compartment were enumerated, and the percentage of migration was calculated as follows: (number of cells migrated/total number of cells plated)×100.

Homing Assay

The homing of re-isolated CD34+ cells ($5 \times 10^5$/mouse) after treatment under control conditions or with VPA was performed as previously described (Shivtiel et at, "CD45 Regulates Homing and Engraftment of Immature Normal and Leukemic Human Cells in Transplanted Immunodeficient Mice," *Exp. Hematol.* 39(12):1161-1170 (2011), which is hereby incorporated by reference in its entirety). The recipient NSG mice were purchased from the Jackson Laboratory and sublethally irradiated (300 cGy) 4 hours prior to infusion of the re-isolated CD34+ cells via the tail vein. Sixteen and 48 hours after their infusion, BM cells were harvested from 2 femurs and 2 tibias from each recipient mouse and analyzed by flow cytometry for the presence of human CD34+ cells using a human CD34-APC mAb. The homing of these cell populations was determined by quantitating the number of CD34+ cells per $10^6$ acquired events in the BM of the recipient mice. Four mice did not receive cells and were similarly analyzed in order to subtract the background from experimental samples (Colvin et al., "Allogeneic In vivo Stem Cell Homing,". *J. Cell, Physiol.* 211(2):386-391 (2007), which is hereby incorporated by reference in its entirety). Eight NSG mice received CD34+ cells cultured under control conditions, and 10 mice received CD34+ cells from VPA-containing cultures.

Cell Cycle Analysis by BrdU Labeling

The cell cycle status of the cultured CD34+CD90+ cells was assessed using the FITC-BrdU Kit (BD Pharmingen) according to the manufacturer's instructions. CB CD34+ cells cultured for 7 days under control conditions in the presence of VPA were subsequently pulsed with BrdU for 2.5 hours. The cells were then washed with staining buffer (PBS plus 3% FBS) and stained with CD34-APC and CD90-PE mAbs, fixed and permeabilized with Cytofix/Cytoperm buffer, and washed with Perm/Wash buffer (both from BD Pharmingen). After permeabilization, cells were treated with 30 µg of DNAse for 30 minutes at 37° C. and then stained with an FITC-conjugated anti-BrdU antibody and 7AAD. The cell cycle status of CD34+CD90+ gated cells was then documented using a FAC-SCanto II Flow Cytometer with FACSDiva software (BD Biosciences).

Effects of HDACIs on HDACs

Whole-cell extracts were prepared from freshly isolated CB-MNCs and human embryonic kidney 293 (HEK293) cells cultured in the presence of SCR (8 µM), C433 (80 µM), and VPA (1.25 mM). Cellular proteins were separated by SDS-PAGE using Novex (Invitrogen) and transferred by iBlot (Invitrogen). The membranes were probed with mAbs against individual histone deacetylases (HDAC1, HDAC2, HDAC3, HDAC4, HDAC5, HDAC6, and β-actin; Cell Signaling Technology) and developed using a chemiluminescence system with HRP-conjugated secondary antibodies (Amersham Biosciences) according to the manufacturer's instructions. Densitometric analysis of Western blotting was performed with ImageJ software (NIH).

Isolation of Primitive Cells Based on ALDH Activity

Increased ALDH activity is a characteristic of primitive hematopoietic cells and cancer stem cells (Hess et al., Functional Characterization of Highly Purified Human Hematopoietic Repopulating Cells Isolated According to Aldehyde Dehydrogenase Activity," *Blood* 104:1648-1655 (2004); Lioznov et al., "Aldehyde Dehydrogenase Activity as a Marker for the Quality of Hematopoietic Stem Cell Transplants," *Bone Marrow Transplant* 35:909-914 (2005); Storms et al., "Distinct Hematopoietic Progenitor Compartments are Delineated by the Expression of Aldehyde Dehydrogenase and CD34," *Blood* 106:95-102 (2005); Aguila et al., "SALL4 is a Robust Stimulator for the Expansion of Hematopoietic Stem Cells," *Blood* 118:576-585 (2011), which are hereby incorporated by reference in their entirety). To identify cell populations with high ALDH activity, an Aldefluor kit (StemCell Technologies Inc.) was used according to the manufacturer's instructions, Cells ($1\times10^6$/ml) were suspended in assay buffer, then half of the cells were added to the Aldefluor substrate (test sample) and the remaining half was added to DEAB inhibitor (control sample). The test and control samples were incubated for 40 minutes at 37° C. Cells were subsequently stained with CD34-APC and/or CD117-PE mAbs or an isotype-matched IgG for an additional 20 minutes. Cells were washed and analyzed by a BD FACSCanto II Flow Cytometer.

qPCR of Pluripotency Genes

Total RNA was extracted from the human ES cell line 89 (WA09; WiCell Research Institute Inc., Madison, Wis., USA), PCs, reisolated CD34+ cells from control cultures or cultures containing VPA in SF and SC media using TRIzol and an RNeasy kit from QIAGEN, CA. Total RNA (0.5-1.0 µg) was reverse transcribed into cDNA using an RNA to cDNA EcoDry Premix kit (Clontech). The primer sequences are listed in Table 6. qPCR was performed using SYBR Green (Thermo Fisher Scientific) and the Realplex thermocycler (Eppendorf). All experiments were performed in triplicate, and non-template controls (lacking cDNA template were included in each assay. GAPDH served as an internal standard. The amplicons were run on a 2% agarose gel with a 50-bp-size (DNA ladder) marker.

TABLE 6

Primer Sequences for RT-PCR and Q-PCR

| Gene | Primer Sequences | |
|---|---|---|
| Pseudo OCT4* | GAAGGTATTCAGCCAAAC (SEQ ID NO: 1) | CTTAATCCAAAAACCCTGG (SEQ ID NO: 2) |
| Pseudo OCT4* | CGACCATCTGCCGCTTTGAG (SEQ ID NO: 3) | CCCCCTGTCCCCCATTCCTA (SEQ ID NO: 4) |
| OCT4 | AACCTGGAGTTTGTGCCAGGGTTT (SEQ ID NO: 5) | TGAACTTCACCTTCCCTCCAACCA (SEQ ID NO: 6) |
| SOX2 | AGAAGAGGAGAGAGAAAGAAAGGGAGAGA (SEQ ID NO: 7) | GAGAGAGGCAAACTGGAATCAGGATCAAA (SEQ ID NO: 8) |
| NANOG | CCTGAAGACGTGTGAAGATGAG (SEQ ID NO: 9) | GCTGATTAGGCTCCAACCATAC (SEQ ID NO: 10) |
| TERT | TGAAAGCCAAGAACGCAGGGATG (SEQ ID NO: 11) | TGTCGAGTCAGCTTGAGCAGGAATG (SEQ ID NO: 12) |
| CD34 | ACAAACATCACAGAAACGACAGT (SEQ ID NO: 13) | TGACAGGCTAGGCTTCAAGGT (SEQ ID NO: 14) |

TABLE 6-continued

Primer Sequences for RT-PCR and Q-PCR

| Gene | Primer Sequences | |
|---|---|---|
| SET | GCAAGAAGCGATTGAACACA (SEQ ID NO: 15) | GCAGTGCCTCTTCATCTTCC (SEQ ID NO: 16) |
| MYST3 | ACTCCACCACCTACGAATGC (SEQ ID NO: 17) | CTCCTTCCTCAGCCTCCTCT (SEQ ID NO: 18) |
| SMARCAD1 | TGGAAGACCTTTCGGAATTG (SEQ ID NO: 19) | CACCTGCATCACCAAACATC (SEQ ID NO: 20) |
| ZIC3 | GCAAGTCTTTCAAGGCGAAG (SEQ ID NO: 21) | CATGCATGTGCTTCTTACGG (SEQ ID NO: 22) |
| GAPDH | from Qiagen | |

*Redshaw & Strain, "Human haematopoietic stem cells express Oct4 pseudogenes and lack the ability to initiate Oct4 promoter-driven gene expression," J. Negat. Results Biomed. 9:2-8 (2010), which is hereby incorporated by reference in its entirety.

Immunofluorescence Staining

PCs and re-isolated, cultured CD34+ cells from control cultures and cultures containing VPA were fixed with methanol-free formaldehyde (2.8%) for 10 minutes at 37° C., briefly chilled on ice, and permeabilized with 100% ice-cold methanol. Cells were further incubated on ice for 20 minutes and blocked with incubation buffer (PBS containing 0.5% BSA) for 10 minutes and stained for SOX2 and OCT4 with an FITC-conjugated mAb or isotype controls for an hour at room temperature. Cells were also stained with a rabbit mAb for NANOG, followed by an FITC-conjugated anti-rabbit secondary antibody, and cells were washed and analyzed by flow cytometry.

PCs and re-isolated cells from control cultures and VPA-containing cultures were deposited onto glass slides, fixed with formaldehyde, and stained with antibodies according to the manufacturer's instructions (Cell Signaling Technology) for SOX2, OCT4, NANOG, and ZIC3. ES cells, which express SOX2, OCT4, NANOG, and ZIC3, served as positive controls. Confocal microscopic analysis was performed using a Leica TCS SP5 (Wetzlar) and z-series. Images were acquired with LAS AF imaging software.

Co-IP of NANOG and OCT4

ES cells and CD34+ cells treated with VPA for 7 days were lysed in RIPA buffer (50 mM Tris-HCl, pH 7.4, 150 mM NaCl, 1% Triton, 0.1% NP40, and 1.5 mM EDTA). Cell lysates from ES or VPA treated cells (1.0 mg) were incubated with 6 µg of IgG (control), 20 µl (6 µg) of NANOG pAb (catalog AF1997; R&D Systems) and run overnight on a rolling platform at 0.4° C. Protein G beads (50 µl) (Cell Signaling Technology) were added the next day, and the samples continued rolling for an additional 4 hours. The beads were washed three times with lysis buffer, and the bound proteins were eluted by boiling the beads. Total cell lysates from ES (25 µg) and VPA-treated (125 µg) cells were fractionated by SDS-PAGE and analyzed by Western blotting using NANOG mAB (Cell Signaling Technology). Proteins from IP experiments were separated by SDS-PAGE, transferred using iBlot (Invitrogen), immunoblotted with goat pAb anti-OCT4, washed, and developed using an ECL detection kit.

siRNA-Mediated Silencing of Pluripotency Genes

CB CD34+ cells were treated with VPA under SF culture conditions. VPA-treated cells were transfected with individual SOX2, OCT4, NANOG, GAPDH, and scrambled siRNA or with a combination of SOX2, OCT4, and NANOG Silencer Select siRNAs (Invitrogen, CA). A GFP plasmid was included to determine the transfection efficiency according to the manufacturer's instructions for the Neon transfection system (Invitrogen).

After 72 hours of VPA treatment, cells ($0.5 \times 10^6$ to $1 \times 10^6$) were washed in PBS and suspended in 8 µl of Neon resuspension buffer R. Individual siRNAs (2 µl, 10-30 nM) or a combination of SOX2, OCT4, NANOG (SON), or pcDNA6.2/EmGFP plasmid (200 ng; Invitrogen) were mixed with the 8 µl of cells according to the manufacturer's instructions. Cells were pulsed three times with a voltage of 1,400 and a width of 20 ms and immediately transferred to pre-warmed media supplemented with cytokines plus VPA. Cell viability was assessed following 48 hours of transfection using the trypan blue exclusion method.

In addition, cells treated with scrambled or combined SON siRNA were stained using human CD34 and CD90 mAbs, and the percentages of CD34+ and CD34+CD90+ cells were determined by flow cytometric analysis. RNA was prepared after 7 days of transfection, and qPCR was performed using the SYBR Green method for SOX2, OCT4, NANOG, ZIC3, CD34, and GAPDH mRNA as described above. Relative expression levels were normalized to CD34 expression. SOX2, OCT4, NANOG, and ZIC3 protein expression levels following SON siRNA-mediated pluripotency gene knockdown were assessed by confocal microscopy as described above.

Assay of In Vivo Marrow-Repopulating Potential of Ex Vivo-Expanded CB CD34+ Cells As described previously, NSG mice were sublethally irradiated with 300 cGy 4 hours prior to the infusion of PCs ($2 \times 10^5$), and CD34+ cells re-isolated after a week of culture under control conditions or cultures containing VPA in the presence or absence of cytokines were injected into NSG mice via the tail vein (Milhem et al., "Modification of Hematopoietic Stem Cell Fate by 5aza 2'deoxycytidine and Trichostatin A," Blood 103:4102-4110 (2004); Araki et al., "Expansion of Human Umbilical Cord Blood SCID-Repopulating Cells Using Chromatin-Modifying Agents," Exp. Hematol. 34:140-149 (2006); Araki et al., "Chromatin-Modifying Agents Permit Human Hematopoietic Stem Cells to Undergo Multiple Celt Divisions While Retaining Their Repopulating Potential," Blood 109:3570-3578 (2007), which are hereby incorporated by reference in their entirety). Mice were sacrificed 13-14 weeks after transplantation. BM cells from each mouse were analyzed for the presence of cells expressing human CD45-PECy7 or APC, CD34-APC or FITC, CD36-APC, CD33-PECy7, CD14-FITC, CD19-

PE, CD41-FITC, CD71-FITC, and glycophorin A-PE (GPA-PE). The presence of at least 0.1% human CD45+ cells in the marrow of each recipient mouse was considered indicative of donor human hematopoietic engraftment (Milhem et al., "Modification of Hematopoietic Stem Cell Fate by 5aza 2'deoxycytidine and Trichostatin A," *Blood* 103:4102-4110 (2004); Araki et al., "Expansion of Human Umbilical Cord Blood SCID-Repopulating Cells Using Chromatin-Modifying Agents," *Exp. Hematol.* 34:140-149 (2006); Araki et al., "Chromatin-Modifying Agents Permit Human Hematopoietic Stem Cells to Undergo Multiple Cell Divisions While Retaining Their Repopulating Potential," *Blood* 109:3570-3578 (2007); Chaurasia et al., "Chromatin-Modifying Agents Promote the Ex vivo Production of Functional Human Erythroid Progenitor Cells," *Blood* 117:4632-4641 (2011), which are hereby incorporated by reference in their entirety). BM cells ($2\times10^6$) from the primary recipient NSG mice were reinfused into sublethally irradiated secondary NSG recipient mice. Mice were sacrificed 15-16 weeks after transplantation, and BM cells were stained with mAbs and analyzed by flow cytometry for evidence of human chimerism as described above.

Limiting Dilution Analysis

The frequency of human SRCs in PCs and the progeny of an equivalent number of CD34+ cells that were expanded under control conditions or in the presence of VPA were analyzed by limiting dilution analysis as described previously (Boitano et al., "Aryl Hydrocarbon Receptor Antagonists Promote the Expansion of Human Hematopoietic Stem Cells," *Science* 329:1345-1348 (2010), which is hereby incorporated by reference in its entirety). Increasing numbers of PCs (50, 250, 500, 2,500, 5,000) or the progeny of an equivalent number of PCs cultured with VPA for 7 days or under control conditions were infused into NSG mice (n=111). The data from the limiting dilution experiments were pooled and analyzed by applying Poisson statistics to the single-hit model (n=111). The frequency was calculated using L-Calc software (StemCell Technologies Inc.) and plotted using ELDA software (bioinf.wehi.edu.au/software/elda/), available at the Walter and Eliza Hall Bioinformatics Institute of Medical Research. The tog fraction of non-responding values was converted to the percentage of negative mice using the following formula: percentage of negative mice=e log fraction.

Assay for Teratoma Formation

CD34+ cells ($1\times10^6$) re-isolated from control cultures or cultures containing VPA or a similar number of ES cells were suspended in 100 μl of PBS. These cells were mixed with an equal volume of ice-cold Matrigel and injected subcutaneously into the right hind limb of three NSG mice per group (re-isolated CD34+ cells from control cultures, VPA-treated cultures, and ES cells). The mice were observed weekly for teratoma formation and sacrificed after 8 weeks. Teratomas were dissected, fixed, sectioned, and stained with H&E and examined morphologically (O'Connor et al., "Functional Assays for Human Embryonic Stem Cell Pluripotency," *Methods Mol Biol.* 690:67-80 (2011), which is incorporated by reference in its entirety).

Statistics

Results are expressed as the mean±SD or the mean±SEM of varying numbers of individual experiments. Statistical differences were evaluated using the Student's two-tailed t test unless otherwise specified. One-way ANOVA with pairwise comparison by Tukey's test and/or Bartlett's test for equal variance and the F test for variance comparison were also used, A P value less than or equal to 0.05 was considered significant.

Study Approval

All animal studies were approved by the animal care and use committee of the Icahn School of Medicine. Informed consent or subject approval was not required for this study, as low-volume unidentifiable CB units were purchased from the New York Blood Center.

Results

Figure 1B:
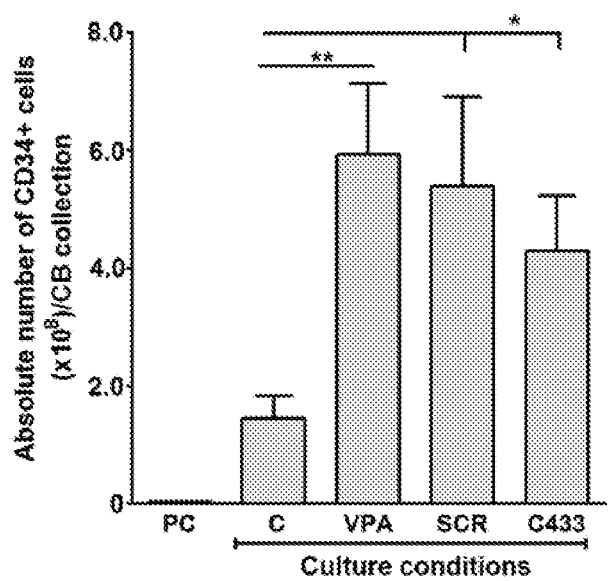
Figure 1C:
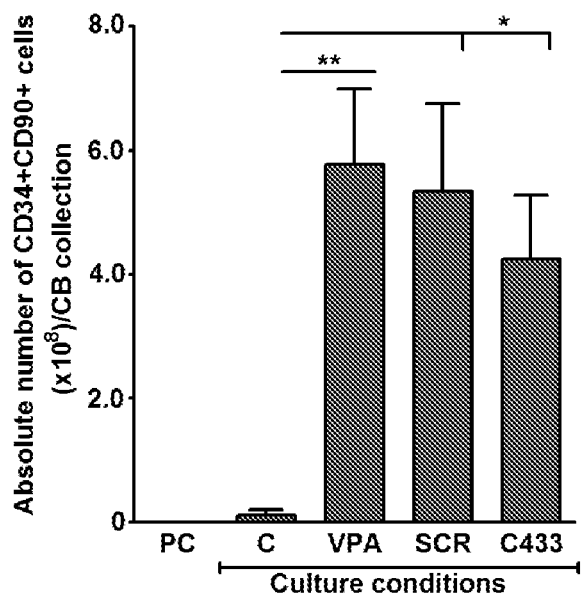
Figure 1D:
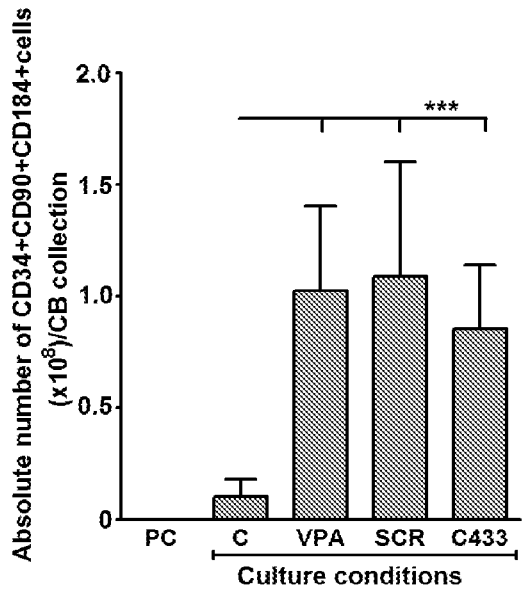

The Effects of HDACIs and SF Media on the Ex Vivo Expansion of CB CD34+ and CD34$^{+CD}$90+ Cells Defining the culture conditions that permit the ex vivo expansion of HSCs has been the subject of numerous investigations (Dahlberg et al., "Ex vivo Expansion of Human Hematopoietic Stem and Progenitor Cells," *Blood* 117:6083-6090 (2011); Delaney et al., "Strategies to Enhance Umbilical Cord Blood Stem Cell Engraftment in Adult Patients," *Expert Rev. Hematol.* 3:273-283 (2010); Boitano et al., "Aryl Hydrocarbon Receptor Antagonists Promote the Expansion of Human Hematopoietic Stem Cells," *Science* 329:1345-1348 (2010); De Felice et al., "Histone Deacetylase Inhibitor Valproic Acid Enhances the Cytokine-Induced Expansion of Human Hematopoietic Stem Cells," *Cancer Res.* 65:1505-1513 (2005); Himburg Et al., "Pleiotrophin Regulates the Expansion and Regeneration of Hematopoietic Stem Cells," *Nat. Med.* 16:475-482 (2010); Milhem et al., "Modification of Hematopoietic Stem Cell Fate by 5aza 2'deoxycytidine and Trichostatin A," *Blood* 103:4102-4110 (2004); Nishino et al., "Ex vivo Expansion of Human Hematopoietic Stem Cells by a Small-Molecule Agonist of c-MPL," *Exp. Hematol.* 37:1364-1377 e1364. (2009); North et al., "Prostaglandin E2 Regulates Vertebrate Haematopoietic Stem Cell Homeostasis," *Nature* 447:1007-1011 (2007), which are hereby incorporated by reference in their entirety), It was previously demonstrated that limited expansion of CB HSC numbers can occur using SC culture conditions and sequential treatment with a DNA methyl transferase inhibitor (DNMTI) and an HDACI (Milhem et al., "Modification of Hematopoietic Stem Cell Fate by 5aza 2'deoxycytidine and Trichostatin A," *Blood* 103:4102-4110 (2004); Araki et al., "Expansion of Human Umbilical Cord Blood. SCID-Repopulating Cells Using Chromatin-Modifying Agents," *Exp. Hematol.* 34:140-149 (2006); Araki et al., "Chromatin-Modifying Agents Permit Human Hematopoietic Stem Cells to Undergo Multiple Cell Divisions While Retaining Their Repopulating Potential," *Blood* 109:3570-3578 (2007); Chaurasia et al., "Chromatin-Modifying Agents Promote the Ex vivo Production of Functional Human Erythroid Progenitor Cells," *Blood* 117:4632-4641 (2011), which are hereby incorporated by reference in their entirety). To further optimize culture conditions that would additionally favor CB HSC expansion, the generation of CD34+ was first evaluated and CD34+CD90+ cells in SF and SC cultures supplemented with cytokines, referred to here as the control conditions. A schematic representation of the ex vivo expansion strategies used to expand CB CD34+ cells and the terminology used to refer to the cell populations studied are provided in FIG. 1A and Table 1. A variety of HDACIs (VPA, scriptaid [SCR], trichostatin A [TSA], suberoylanilide hydroxamic acid [SAHA], CAY10433 also known as BML-210 [C433], CAY10398, also known as MD85, and CAY10603 [molecular formula: $C_{22}H_{30}N_4O_6$]) were added at varying doses and periods of incubation (5-9 days). Their ability to increase the numbers of CD34+ cells generated in vitro under SC or SF culture conditions was evaluated. Of the eight HDACIs studied, treatment with VPA, SCR, and C433 for 7 days was shown to be most effective for this purpose. Treatment with each of these agents led to the generation of a similar percentage of CD34$^+$CD90$^+$ cells (SCR: 73.4%±13.9%, C433: 70.1%±18.4%, and VPA: 75.2%±10.7%) as compared with control conditions (16.2%±9.2%) (ANOVA, P<0.0001). However, the percentages progressively declined if the cells were maintained beyond 7 days. Similarly, it was found that each of these HDACIs was effective in generating a greater absolute number of CD34+ and CD34+CD90+ cells per CB collection (ANOVA, P≤0.0007) (FIGS. 1B and 1C) as well as promoting CXCR4 expression (CD184) by CD34+ CD90+ cells and generating a greater absolute number of CD34+CD90+CD184+ cells as compared with control conditions (ANOVA, P<0.0001) (FIG. 1D). The effects of VPA, SCR, and C433 were not additive when combined at optimal and half-optimal concentrations.

Figure 2A:
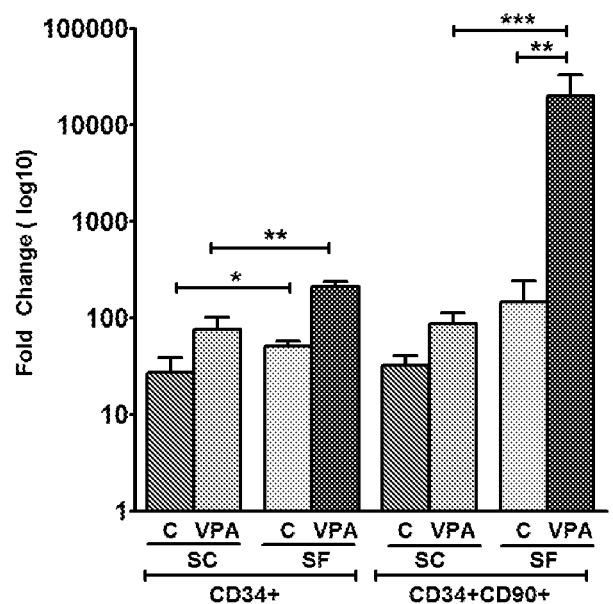
FIGS. 2A-B show the effect of VPA on the ex vivo expansion of CB CD34+ and CD34+CD90+ cells.

The effect of serum on the ability of HDACIs to promote CD34+ cell expansion was more carefully examined. The use of SF control culture conditions led to a greater expansion of CD34+ and CD34+CD90+ cell numbers than that achieved with SC control culture conditions (ANOVA, P<0.0001, respectively) (FIG. 2A). Under SF conditions, the addition of VPA led to a dramatic increase in the number of CD34+ (213-fold) and CD34+90+ (20,202-fold) cells as compared with SC conditions with VPA (a 78-fold expansion of the CD34+ cells and an 89-fold expansion of CD34+90+ cells; ANOVA, P≤0.005) (FIG. 2A).

Figure 2B:
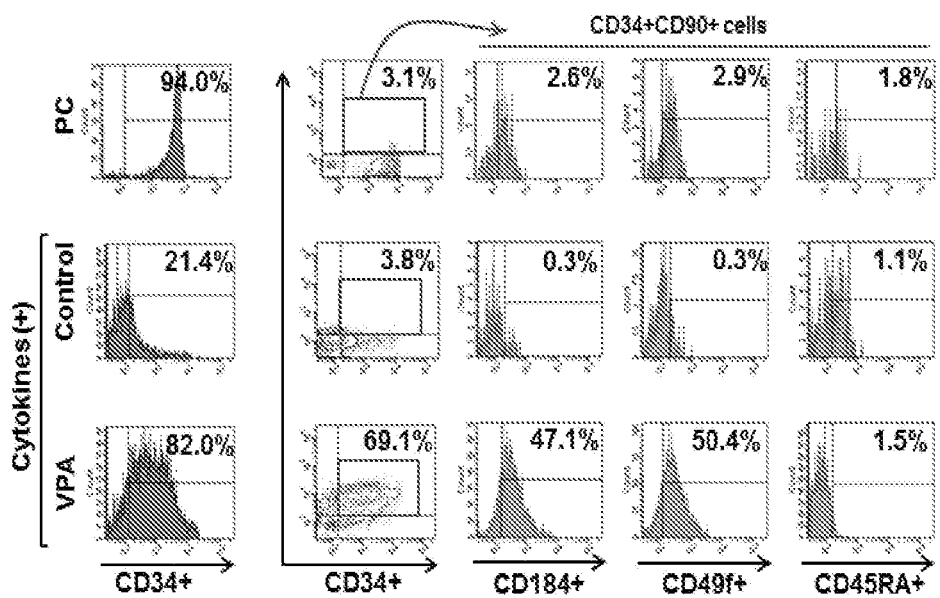

A more careful phenotypic analysis of the VPA-expanded CD34+ cells was examined by analyzing the expression of an isoform of the leukocyte common antigen CD45RA and integrin α6 (CD49f) by CD34+CD90+ VPA-treated cells. Human HSCs have been shown to express CD49f but not CD45RA (Notta et al., "Isolation of Single Human Hematopoietic Stem Cells Capable of Long-Term Multilineage Engraftment," Science 333(6039):218-221 (2011), which is hereby incorporated by reference in their entirety). In FIG. 2B, it is demonstrated that 47.0%±4.4% of the CD34+ CD90+ cells from the cultures containing VPA expressed CD49f, while a minority of these cells expressed CD45RA (1.9%±2.1%).

Figure 3A:
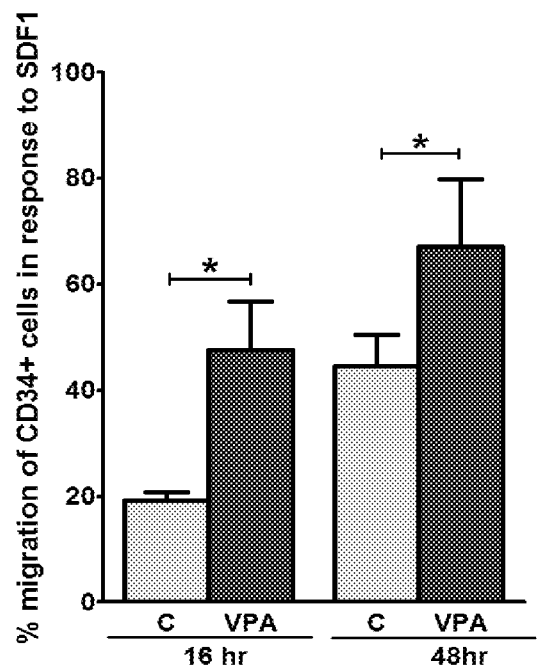
FIGS. 3A-B show the effect of VPA on CD34+ cell migration and homing.
Figure 3B:
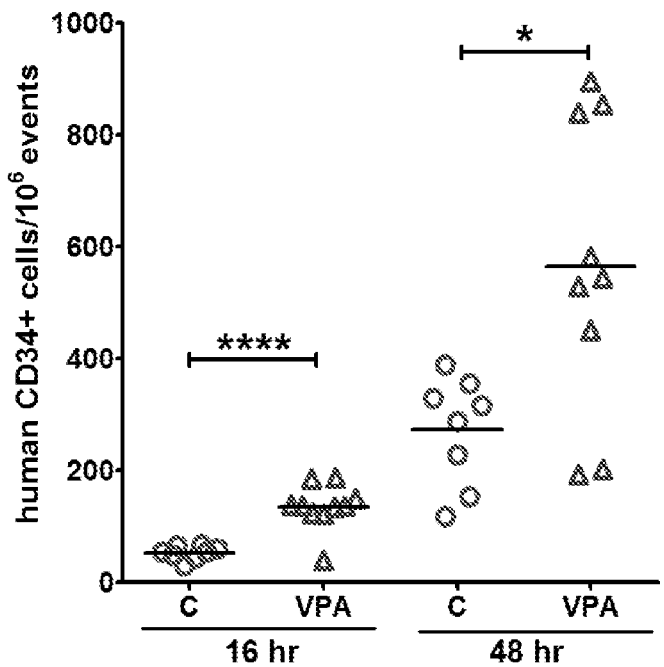
Figure 4A:
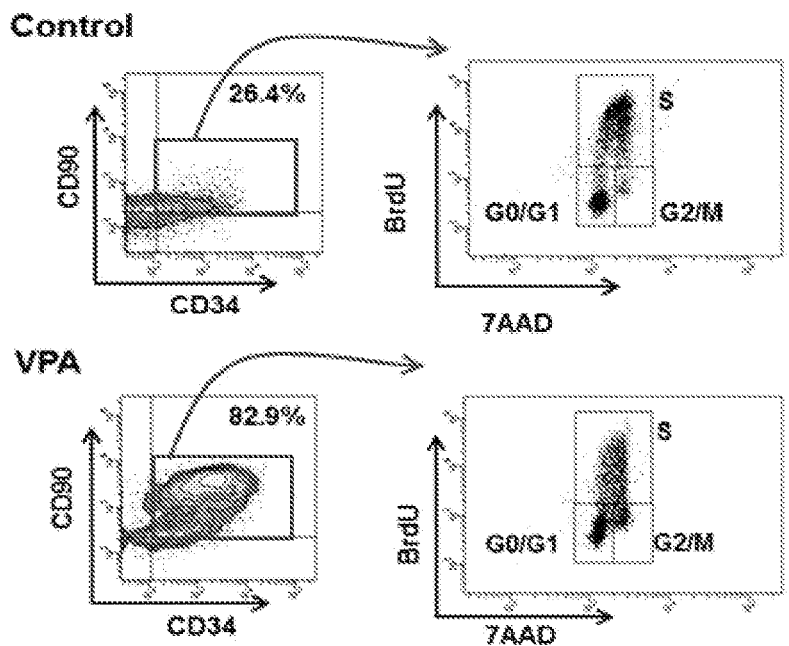
FIGS. 4A-B show the effect of VPA on the different phases of the cell cycle of CD34+CD90+ cells.
Figure 4B:
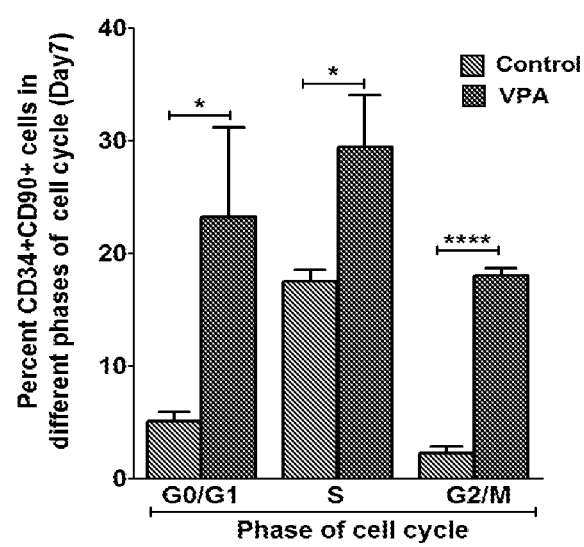
Figure 5A:
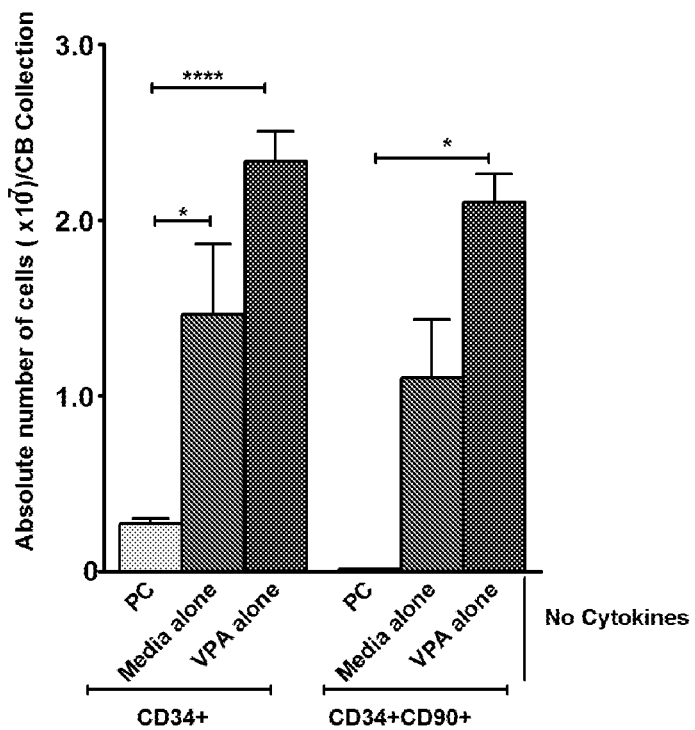
FIGS. 5A-B show the effect of VPA on the ex vivo expansion of CB CD34+ and CD34+CD90+ cells in the absence of cytokines.
Figure 5B:
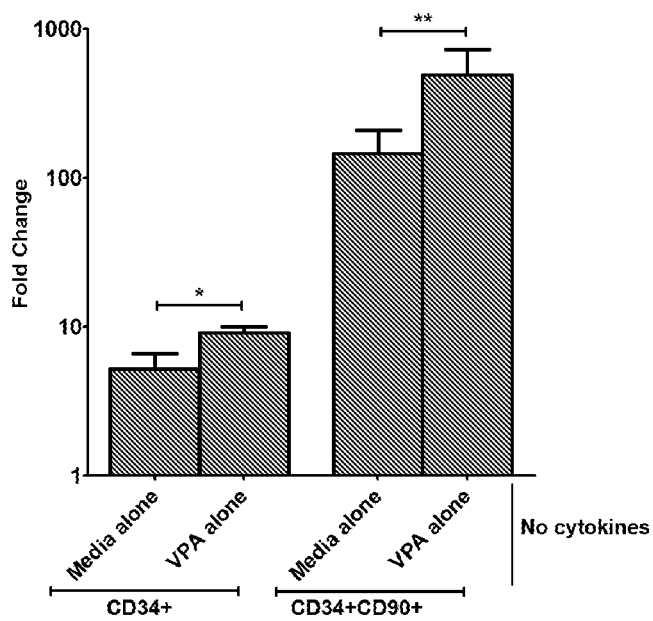
Figure 14:
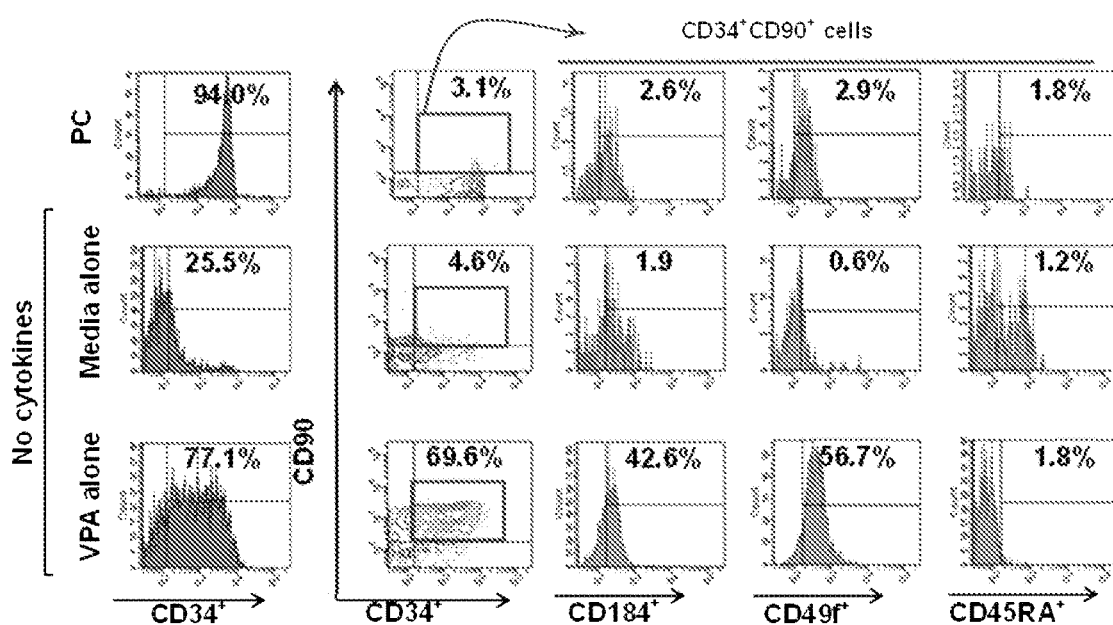
FIG. 14 shows the results of phenotypic analysis of primary cord blood (CB) CD34+ cells (PC) and CD34+ cells cultured in the serum-free (SF) media without cytokines (Media alone) or in the presence of VPA alone without cytokines for 7 days. CD34, CD90, CXCR4 (CD184), CD49f and CD45RA expression by cultured cells is shown. The co-expression of CD184, CD49f, and CD45RA by CD34+CD90+ cells is depicted. (n=4)

Since the CXCR4/SDF1 axis is critical for HSC horning (Gut et al., "Valproic Acid Increases CXCR4 Expression in Hematopoietic Stem/Progenitor Cells by Chromatin Remodeling," Stem Cells Dev. 18:831-838 (2009), which is hereby incorporated by reference in its entirety), the migration of VPA-treated CD34+ cells was examined in response to SDF1. As can be seen in FIG. 3A, a significantly greater number of CD34+ cells treated with VPA migrated in response to SDF1 after 16 and 48 hours (P=0.01 and P=0.03). It was next examined whether the upregulation of CXCR4 expression by CD34+ cells following VPA treatment was associated with increased horning of these cells to the marrow of NOD/SCID/γcnull (NSG) mice. As demonstrated in FIG. 3B, VPA treatment led to increased horning of CD34+ cells as compared with CD34+ cells cultured under control conditions at both 16 hours (P<0.0001) and 48 hours (P=0.01) after infusion. The cell cycle status of the cultured CD34+ cells was next examined by labeling the cellular progeny within control cultures and cultures containing VPA with BrdU (2.5 hours) on day 7 of culture and the proportion of CD34+CD90+ cells that resided in different phases of the cell cycle were compared (FIG. 4A). It was found that the cells treated with VPA contained a far greater proportion of CD34+CD90+ cells than did control cultures (75.2%±10.7% versus 16.2%±9.2%). In addition, a greater number of VPA-treated CD34+CD90+ cells resided within G2/M (18.0%±1.2%) than did the cells in control cultures (2.2%±1.0%, P<0.0001), indicating that VPA-treated CD34+CD90+ cells continue to divide and retain their primitive phenotype, thereby accounting for the greater numbers of CD34+CD90+ cells observed on day 7. The CD34+CD90+ G0/G1 cell compartment was also increased in VPA-containing cultures (23.2%±13.8%) as compared with that seen in control cultures (5.0%±1.4%), suggesting that CD34+CD90+ cells exposed to VPA were capable of returning to G0/G1. Also, a smaller proportion of CD34+ CD90+ cells from control cultures were in the S phase than those in the VPA-containing cultures (17.5%±1.8% versus 29.4%±7.9%) after 7 days of culture (FIG. 4B). These data suggest that the control cells divided earlier during the culture period than did VPA-treated cells, which continued to divide and generate CD34+CD90+ cells on day 7. In order to determine whether the effects of VPA were dependent on the continued exposure to cytokines, CB CD34+ cells underwent initial priming for 16 hours and were then cultured for 7 days in SF media alone or in SF media supplemented with VPA, but in the absence of additional cytokines (FIG. 1A). These studies demonstrated that after an initial priming with cytokines, expansion of CD34+ and CD34+90+ cells occurred following incubation in SF media alone (no cytokines (FIG. 5A)). An even greater absolute number of CD34+ (P<0.0001) and CD34+CD90+ cells (P<0.05), however, was generated when the cells were cultured in the presence of VPA alone (no cytokines), as compared with PCs (FIG. 5A). This same degree of expansion of CD34+ cells, however, did not occur in cultures that were not initially primed and then incubated without additional cytokines, indicating the dependence of the expansion of CD34+ and CD34+CD90+ cell numbers on at least prior exposure to cytokines. On day 7, 21.2%±5.1% of cells cultured in media alone (no cytokines) were CD34+, and their phenotype was similar to that of PCs, while the cells that were exposed to VPA alone were characterized by a dramatic upregulation of CD90, CD184, and CD49f, but not CD45RA (FIG. 14), findings consistent with VPA leading to epigenetic reprogramming. The CD34+ and CD34+CD90+ cell numbers per CB collection underwent a 5.2-fold and 144-fold expansion when cultured in media alone (no cytokines) as compared with a 9.0-fold and 486-fold expansion, respectively, in cultures containing VPA alone (no cytokines) (ANOVA, P<0.0001) (FIG. 5B), The degree of expansion of CD34+ (213fold) and CD34+CD90+ (20,202-fold) cells was even more dramatically enhanced by the addition of cytokines to VPA-containing SF cultures during the 7-day incubation period (FIG. 2A).

Effect of HDACIs on HDAC Levels

Figure 6:
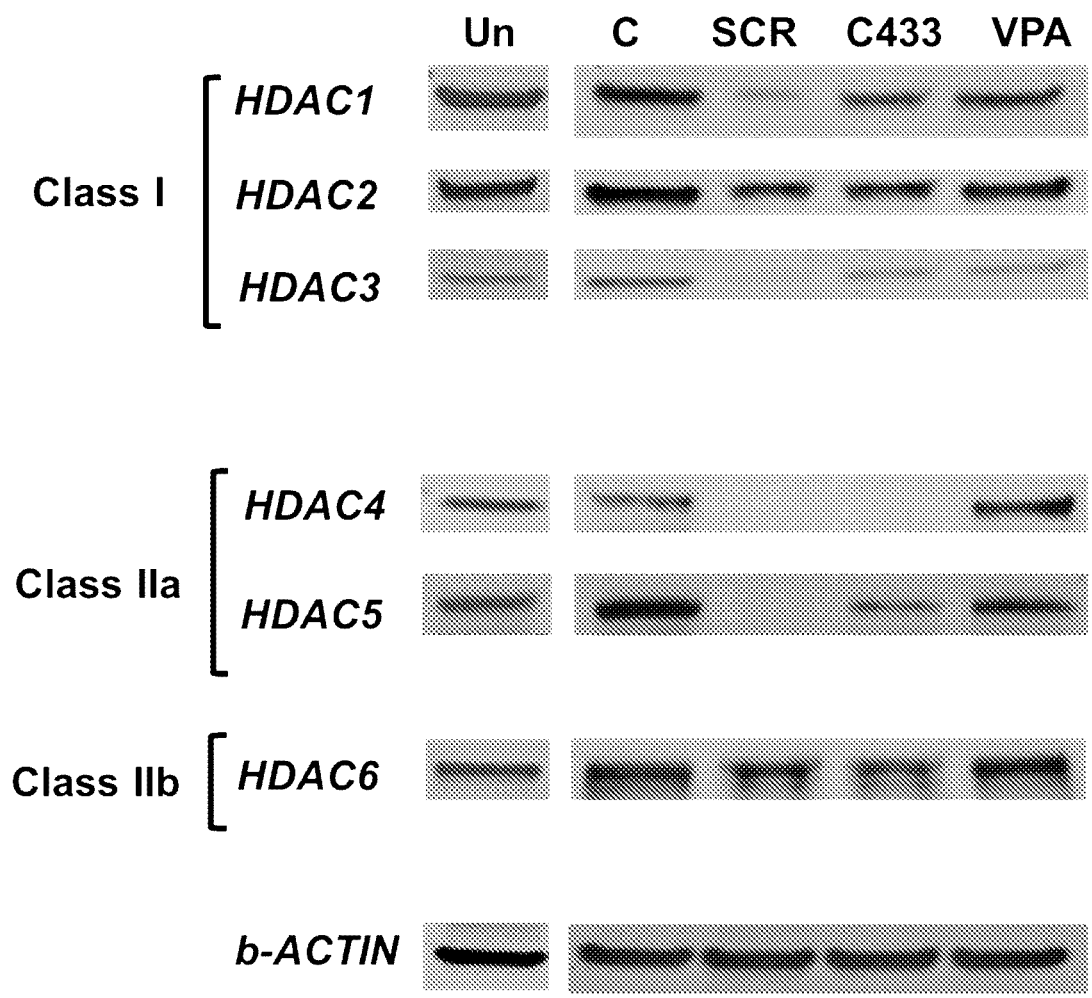
FIG. 6 shows the effect of HDACIs on HDAC protein expression levels. Cord blood-mononuclear cells (CB-MNCs) were freshly isolated and treated in the absence and presence of Scriptaid (SCR), CAY10433 (C433) or valproic acid (VPA) for 24 hr. Total cell lysates were prepared and Western blots were performed using HDAC mAbs specific to class I (1, 2, and 3), class IIa (4 and 5) and class IIb (6) HDACs as described in the Examples. b-ACTIN was used as a loading control. Un-untreated freshly isolated CB-MNCs, C-control. One of 4 representative experiments is shown.

HDACs exist in cells as subunits of multi-protein complexes and govern gene expression. The class I HDACs (HDAC1, -2, -3, and -8) possess sequence homology to the yeast transcriptional regulator RPD3. However, class II HDACs (HDAC4, -5, -6, -7, -9, and -10) share domains similar to those of deacetylase HDA1, which is found in yeast (Delcuve et al., "Roles of Histone Deacetylases in Epigenetic Regulation: Emerging Paradigms from Studies with inhibitors," Clin. Epigenetics 4(1):5 (2012), which is hereby incorporated by reference in its entirety). Class I and II HDACs interact with the transcriptional corepressors mSIN3, NCoR, and SMRT, which recruit HDACs to transcription factors (Delcuve et al., "Roles of Histone Deacetylases in Epigenetic Regulation: Emerging Paradigms from Studies with Inhibitors," Clin. Epigenetics 4(1):5 (2012); Kramer et al., "The Histone Deacetylase Inhibitor Valproic Acid Selectively Induces Proteasomal Degradation of HDAC2," *EMBO J.* 22:3411-3420 (2003), which are hereby incorporated by reference in their entirety). HDACIs have been previously shown to lead to increased H3 acetylation in CB CD34+ cells (Chaurasia et al., "Chromatin-Modifying Agents Promote the Ex viva Production of Functional Human Erythroid Progenitor Cells," *Blood* 117:4632-4641 (2011), which is hereby incorporated by reference in its entirety). HDAC activities, however, can be modulated not only by the binding of these inhibitors at the catalytic domain, but also by fine-tuned degradation of HDACs through the ubiquitin/proteasome pathway. Limiting amounts of the E2 ubiquitin conjugase Ubc8 and the E3 ubiquitin ligase RLIM have been reported to maintain a balanced steady-state protein level of HDACs that is susceptible to modulation by VPA (Kramer et al., "The Histone Deacetylase Inhibitor Valproic Acid Selectively Induces Proteasomal Degradation of HDAC2," *EMBO J.* 22:3411-3420 (2003); Cedar et al., "Epigenetics of Haematopoietic Cell Development," *Nat. Rev. Immunol.* 11:478-488 (2011); Cunliffe, "Eloquent Silence: Developmental Functions of Class I Histone Deacetylases," *Curr. Opin. Genet. Dev.* 18(5):404-410 (2008), which are hereby incorporated by reference in their entirety). In order to determine which HDACs were affected by the HDACIs, the effects of SCR, C433, and VPA on both class I and II HDAC protein levels were evaluated in CB mononuclear cells (CB-MNCs) and human embryonic kidney 293 (HEK293) cells after 2 and 24 hours of treatment. SCR, C433, and VPA did not inhibit HDAC expression after 2 hours of treatment of CB-MNCs, but led to the inhibition of class I (HDAC1, -2, and -3), class IIa (HDAC4 and -5), and class IIb (HDAC6) HDACs to differing degrees after 24 hours of treatment. SCR and C433 were the most effective inhibitors of each of the HDACs (FIG. 6 and Table 7).

TABLE 7

Densitometric Analysis of Western Blots

HDAC expression relative to b-ACTIN (%)

|  | Control | SCR | YPA | C433 |
|---|---|---|---|---|
| HDAC1 | 46.1 ± 4.6 | 21.0 ± 20.0 | 25.48 ± 7.78 | 24.3 ± 0.4 |
| HDAC2 | 67.0 ± 25.2 | 33.0 ± 7.0 | 45.8 ± 25.2 | 40.0 ± 8.0 |
| HDAC3 | 40.5 ± 7.4 | 4.7 ± 3.1 | 11.4 ± 12.4 | 28.0 ± 20.0 |
| HDAC4 | 43.4 ± 11.8 | 16.6 ± 7.8 | 30.5 ± 9.3 | 23.5 ± 16.5 |
| HDAC5 | 54.8 ± 9.4 | 22.8 ± 30.6 | 21.4 ± 10.7 | 12.6 ± 1.9 |
| HDAC6 | 59.5 ± 5.6 | 41.3 ± 7.9 | 54.2 ± 7.9 | 35.8 ± 7.2 |

HDAC down-regulation relative to control (%)

| HDAC1 | SCR | VPA | C433 |
|---|---|---|---|
| HDAC2 | 54.3 ± 49.2 | 45.3 ± 11.5 | 40.6 ± 15.0 |
| HDAC3 | 49.2 ± 8.6 | 16.5 ± 12.0 | 41.7 ± 5.3 |
| HDAC4 | 89.0 ± 5.7 | 40.6 ± 19.9 | 51.4 ± 13.6 |
| HDAC5 | 62.78 ± 7.9 | 30.0 ± 2.4 | 47.2 ± 22.5 |
| HDAC6 | 62.6 ± 49.4 | 58.6 ± 26.7 | 70.3 ± 1.0 |
| HDAC1 | 30.9 ± 6.8 | 9.1 ± 4.8 | 49.1 ± 19.1 |

Upper panel: HDAC protein levels were evaluated by densitometry and were normalized to b-ACTIN expression. Lower panel: Percent downregulation of class I and class II HDACs with respect to control. A reduction in HDAC1, -3 and -5 occurred in the presence of each HDACI. (mean ± SE, n = 4).

Figure 15:
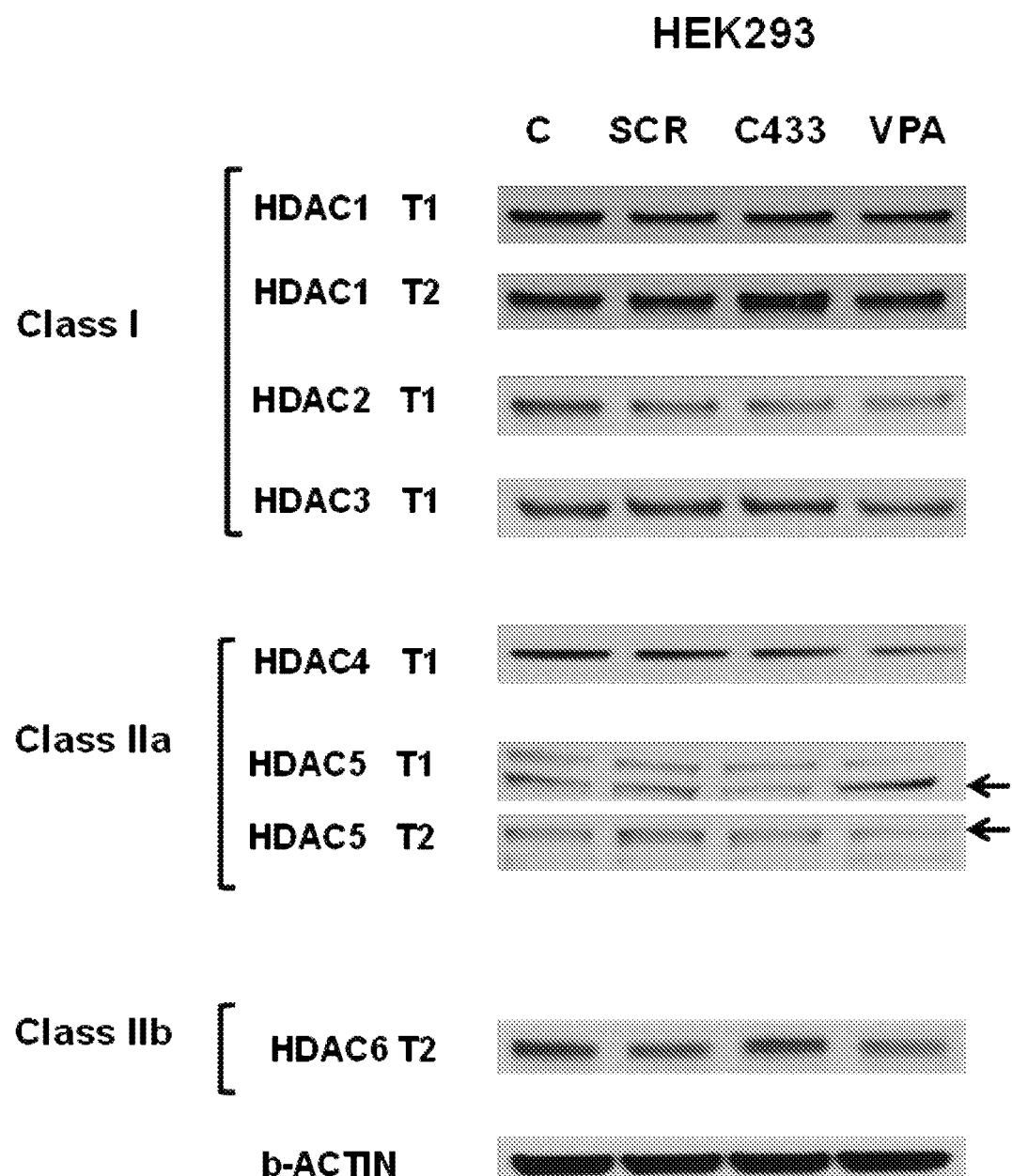
FIG. 15 shows the effect of HDACIs on HDAC protein levels in HEK293 cells. HEK293 cells were treated with SCR, C433, and VPA for 2 hr (T1) and 24 hr (T2). Western blots were probed with primary monoclonal antibodies (mAb) to several Class I (1, 2, and 3), Class IIa (4 and 5) and Class IIb (6) HDACs as described in the Examples. Each HDACI uniformly affected the expression of HDAC2 and HDAC4. β-actin was used as a loading control. (n=4)

Since individual HDACs play crucial roles in regulating intracellular processes and responding to the extracellular environment in cell-specific functions, the ability to predict the manner in which a particular cell type will respond to a given HDACI is limited (Delcuve et al., "Roles of Histone Deacetylases in Epigenetic Regulation: Emerging Paradigms from Studies with inhibitors," *Clin. Epigenetics* 4(1):5 (2012); Cedar et al., "Epigenetics of Haematopoietic Cell Development," *Nat. Rev. Immunol.* 11:478-488 (2011); Kouzarides, "Chromatin Modifications and Their Function," *Cell* 128:693-705 (2007); Oh et al., "Concise Review: Multidimensional Regulation of the Hematopoietic Stem Cell State," *Stem Cells* 30:82-88 (2012), which are hereby incorporated by reference in their entirety). It was found that the pattern of HDAC inhibition following the treatment of HEK293 cells with these HDACIs was remarkably different than that of CB-MNCs, and was more pronounced after 2 hours of treatment as compared with 24 hours (FIG. 15). Downregulation of HDAC2 and HDAC4 was common to the effects of each of the three HDACIs on HEK293 cells, while a reduction of HDAC1, -3, and -5 was common to CB-MNCs treated with the same agents. These findings indicate that SCR, C433, and VPA are each class I and II HDACIs, but that their effects on specific HDACs vary depending on the cell type being treated. It has been previously shown that downregulation of HDAC3 is essential for in vitro HSC expansion (Elizalde et al., "Histone Deacetylase 3 Modulates the Expansion of Human Hematopoietic Stem Cells," *Stem Cells Dev.* 21:2581-2591 (2012), which is hereby incorporated by reference in its entirety). Each of the HDACIs examined was capable of expanding CB CD34+ cell numbers, but VPA was the most effective compound in promoting CD34+ cell expansion, yet was not the most potent inhibitor of HDACs. The remaining experiments were carried out with VPA.

VPA Alters ALDH Activity in Cultured CB CD34$^+$ Cells

Figure 7A:
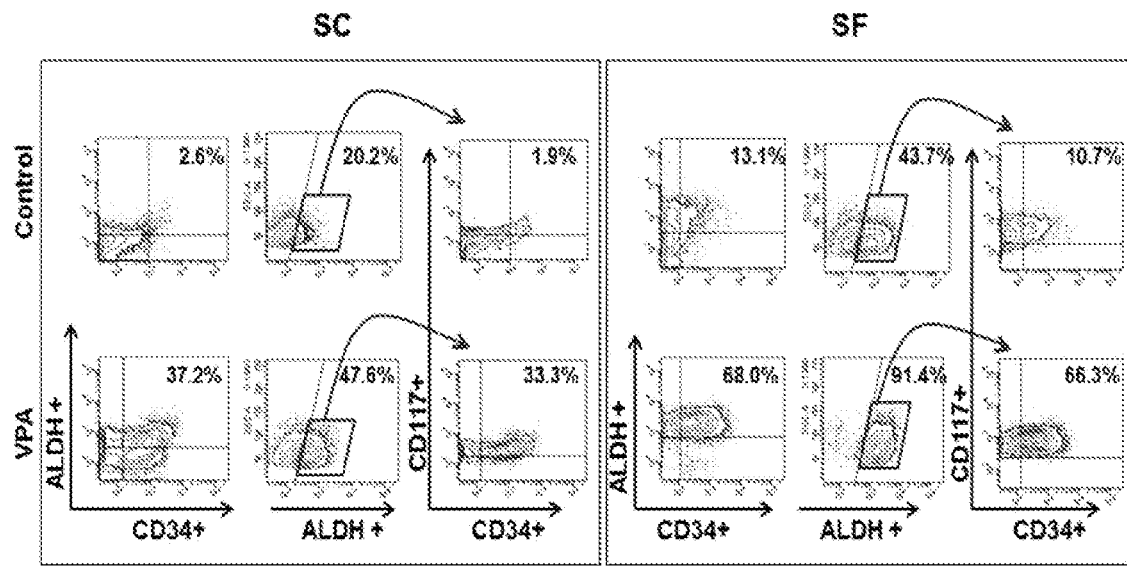
FIGS. 7A-B illustrate aldehyde dehydrogenase (ALDH) functional activity in expanded CB-CD34+ cells.

Since the phenotype of CB and marrow cells expanded in vitro with cytokines does not always correlate with function, ALDH activity was used as a functional marker of HSC (Hess et al., Functional Characterization of Highly Purified Human Hematopoietic Repopulating Cells Isolated According to Aldehyde Dehydrogenase Activity," *Blood* 104:1648-1655 (2004); Lioznov et al., "Aldehyde Dehydrogenase Activity as a Marker for the Quality of Hematopoietic Stem Cell Transplants," *Bone Marrow Transplant* 35:909-914 (2005); Spangrude et al., "Long-Term Repopulation of Irradiated Mice with Limiting Numbers of Purified Hematopoietic Stem Cells: In vivo Expansion of Stem Cell Phenotype but not Function," *Blood* 85(4):1006-1016 (1995); Storms et al., "Distinct Hematopoietic Progenitor Compartments are Delineated by the Expression of Aldehyde Dehydrogenase and CD34," *Blood* 106:95-102 (2005); Veeraputhiran et al., "Aldehyde Dehydrogenase as an Alternative to Enumeration of Total and Viable CD34(+) Cells in Autologous Hematopoietic Progenitor Cell Transplantation," *Cytotherapy* 13:1256-1258 (2011), which are hereby incorporated by reference in their entirety). A higher fraction of cells with ALDH activity was observed in cells cultured in SF cultures than in those cultured in SC cultures in the presence of cytokines. Furthermore, the addition of VPA to cultures containing cytokines under SF culture conditions led to an even greater proportion of ALDH+ cells compared with that observed in SC cultures (FIG. 7A and Table 2).

TABLE 2

Frequency of ALDH+, ALDH+CD34+, and ALDH+CD34+CD117+ Cells

| Cell population | SC Cultures | | SF Cultures | |
| --- | --- | --- | --- | --- |
| | Control | VPA | Control | VPA |
| ALDH+ | 14.4 ± 8.1 | 41.7 ± 3.3$^A$ | 27.2 ± 5.7 | 86.6 ± 7.4$^A$ |
| ALDH+CD34+ | 4.0 ± 1.4 | 26.1 ± 5.5$^A$ | 8.8 ± 2.9 | 71.1 ± 3.1$^A$ |
| ALDH+CD34+CD117+ | 4.3 ± 1.7 | 29.4 ± 1.4$^A$ | 13.1 ± 2.9 | 51.3 ± 4.0$^A$ |

PCs were cultured under control conditions or in cultures containing VPA in SF or SC media. The addition of VPA to SF cultures led to a greater degree of ALDH activity in CD34+ and CD34+CD117+ cells as compared with that observed in SC cultures. Each value represents the percentage of cells with a particular phenotype. Mean ± SEM.
$^A$P ≤ 0.007. ANOVA, P < 0.0001. n = 3-5.

Figure 7B:
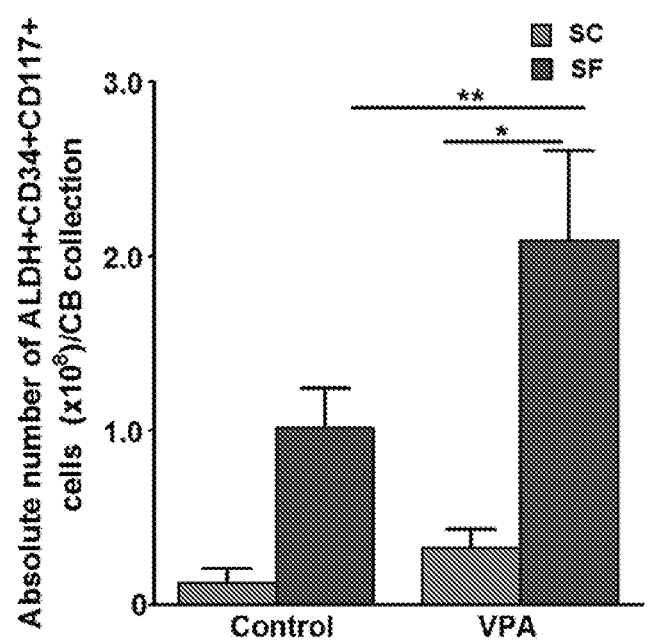

The absolute number of ALDH$^+$CD34$^+$CD117$^+$ cells generated in SF cultures plus VPA was greater than that achieved in SC cultures (P=0.009) (FIG. 7B).

VPA Influences the Expression of Genes Associated with Pluripotency

Figure 8A:
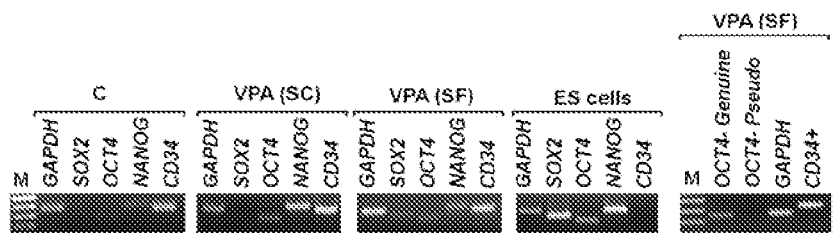
FIGS. 8A-C show the results of transcripts of the pluripotency genes in VPA expanded CD34+ cells.
Figure 8B:
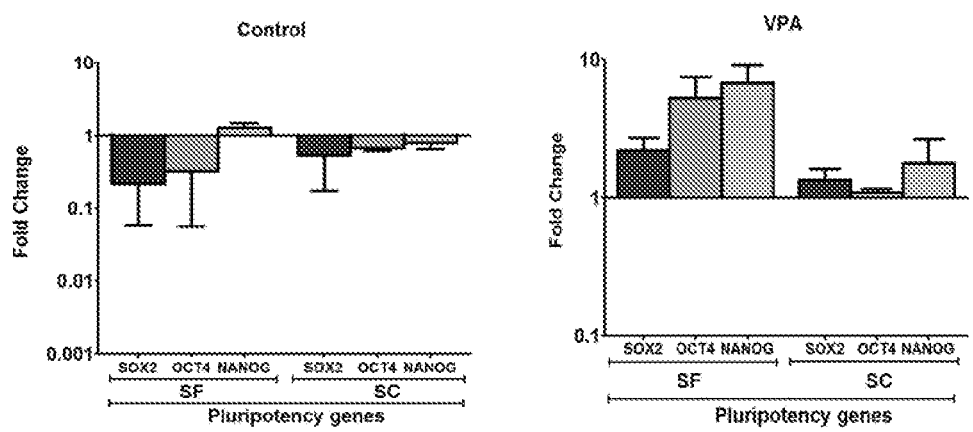
Figure 8C:
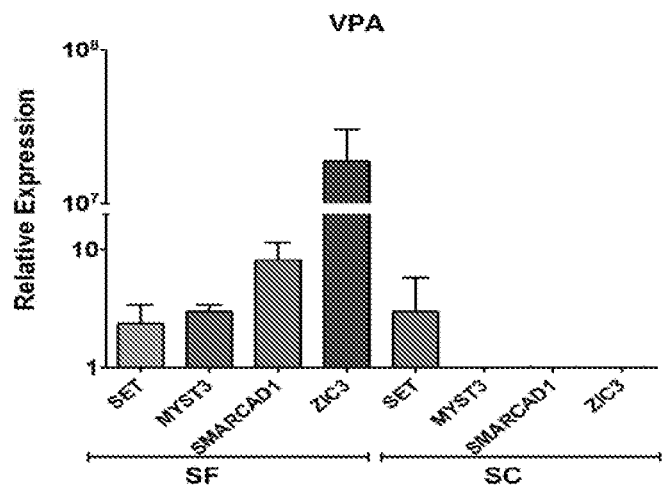

The transcription factors SOX2, OCT4, and NANOG are the core regulatory players in determining both embryonic and induced pluripotent stem cell (iPS) fate decisions by co-occupying target genes including their promoters, thereby cooperating in both regulatory and autoregulatory feedback loops required to maintain self-renewal and pluripotency (Boyer et al., "Core Transcriptional Regulatory Circuitry in Human Embryonic Stem Cells," *Cell* 122:947-956 (2005); Loh et al., "The Oct4 and Nanog Transcription Network Regulates Pluripotency in Mouse Embryonic Stem Cells," *Nat. Genet.* 38(4):431-440 (2006), which are hereby incorporated by reference in their entirety). The role of such master transcription factors in VPA-mediated HSC expansion was explored by examining SOX2, OCT4, and NANOG expression in the CD34+ cells re-isolated after 7 days of culture under control conditions or in those treated with VPA in SF and SC media. RT-PCR revealed the expression of SOX2, OCT4, and NANOG transcripts in CD34+ cells from SE cultures containing VPA, while OCT4 and SOX2 transcripts were barely detectable in the control cultures or SC cultures to which VPA was added (FIG. 8A). Quantitative PCR (qPCR) demonstrated that expression of these pluripotency genes was upregulated in the presence of VPA in SF cultures (ANOVA, P=0.0001) (FIG. 8B) as compared with that observed in SC cultures. The possibility that OCT4 expression in adult stem cells is actually due to the expression of inactive pseudogenes rather than to a functional form of OCT4 has been reported by others (Redshaw et al., "Human Haematopoietic Stem Cells Express Oct4 Pseudogenes and Lack the Ability to Initiate Oct4 Promoter-Driven Gene Expression,"*J. Negat. Results Biomed.* 9(1):2-8 (2010); Zangrossi et al., "Oct-4 Expression in Adult Human Differentiated Cells Challenges its Role as a Pure Stem Cell Marker," *Stem Cells* 25:1675-1680 (2007), which are hereby incorporated by reference in their entirety). Using RT-PCR, it was found that one OCT4 pseudogene was not present in VPA-treated CD34+ cells (FIG. 8A). qPCR analysis indicated that neither of the two pseudogene transcripts were present, Unlike OCT4, SOX2, and NANOG, telomerase reverse transcriptase (hTERT), another known marker of pluripotency in ES cells (Takahashi et al., "Induction of Pluripotent Stem Cells from Adult Human Fibroblasts by Defined Factors," *Cell* 131:861-872 (2007), which is hereby incorporated by reference in its entirety), was not upregulated in VPA-treated CD34+ cells. Downstream target genes of SOX2, OCT4, and NANOG, including SET, SMARCAD1, and MYST3, which play critical roles in chromatin remodeling were examined, as well as an additional pluripotent gene, ZIC3 (Boyer et al., "Core Transcriptional Regulatory Circuitry in Human Embryonic Stem Cells," *Cell* 122:947-956 (2005); Takahashi et al., "Induction of Pluripotent Stem Cells from Adult Human Fibroblasts by Defined Factors," *Cell* 131:861-872 (2007); Lim et al., "Zic3 is Required for Maintenance of Pluripotency in Embryonic Stem Cells," *Mol. Biol. Cell* 18:1348-1358 (2007), which are hereby incorporated by reference in their entirety). SMARCAD1, MYST3, and ZIC3, but not SET, were also dramatically upregulated in VPA-treated CD34+ cells in SF cultures (ANOVA, P=0.04). ZIC3 mRNA was not detected in control cultures supplemented with VPA in the presence of serum, but was exclusively upregulated in SF cultures supplemented with VPA (FIG. 8C). The ZIC3 gene has been identified as a target of OCT4, SOX2, and NANOG in ES cells. ZIC3 overlaps with the OCT4, NANOG, and SOX2 transcriptional networks, is important in maintaining pluripotency, and can directly modulate the expression of NANOG (Boyer et al., "Core Transcriptional Regulatory Circuitry in Human Embryonic Stem Cells," *Cell* 122:947-956 (2005); Lim et al., "Zic3 is Required for Maintenance of Pluripotency in Embryonic Stem Cells," *Mol. Biol. Cell* 18:1348-1358 (2007); Declereq et al., "Zic3 Enhances the Generation of Mouse Induced Pluripotent Stem Cells," *Stem Cells Dev.* (2013), which are hereby incorporated by reference in their entirety).

Figure 9A:
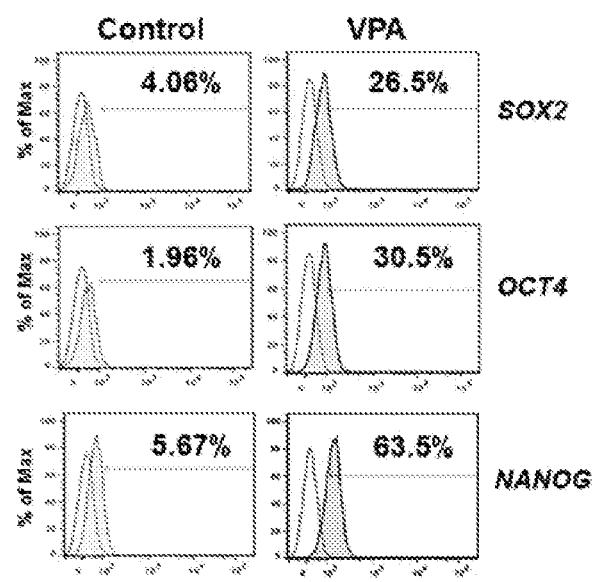
FIGS. 9A-C shows results of expression of pluripotency genes in VPA expanded CD34+ cells.
Figure 9B:
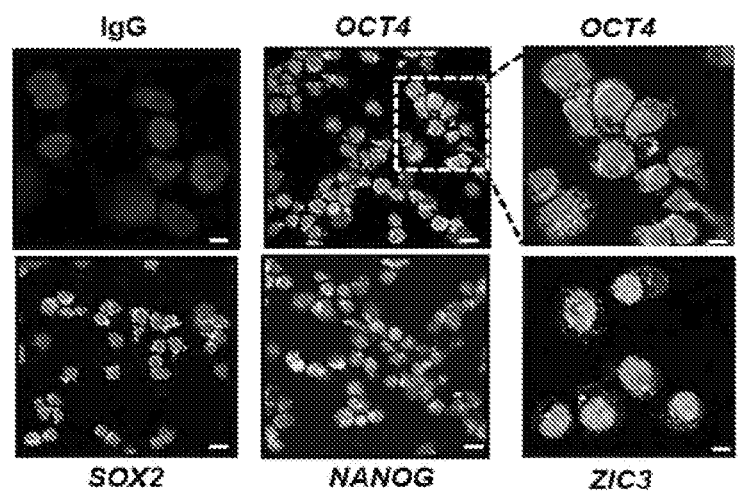
Figure 16:
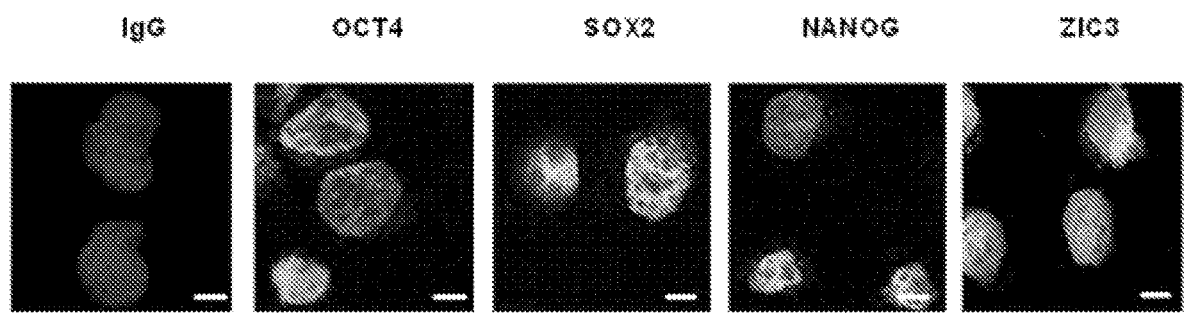
FIG. 16 shows the results of confocal microscopic analysis of pluripotency genes in ES cells. ES(H9) cells were fixed, permeabilized, and stained with OCT4/SOX2/NANOG/ZIC3 antibodies (FITC) as described in the Examples. The nuclei were stained with DAPI. Pluripotency gene proteins including SOX2, OCT4, NANOG, and ZIC3 were more prominent in the nuclei than cytoplasm of ES cells. A single optical section of the confocal z-series (scale bar=25 μm (63× magnification, with optical zoom)) is shown.

The expression of SOX2, OCT4, and NANOG proteins in CD34+ cells was then examined by flow cytometric analysis. SOX2, OCT4, and NANOG expression was greatest in the presence of VPA in SF cultures rather than in SC cultures (FIG. 9A and Table 3). The expression of SOX2, OCT4, and NANOG proteins in CD34+ cells was then examined using mAb staining and confocal microscopy (FIG. 9B and FIG. 16). The pluripotency genes were upregulated and localized to both the nucleus and cytoplasm in the VPA-treated CD34+ cells, while in ES cells, these proteins were predominantly localized to a subnuclear area, Although these proteins were not observed in CD34+ cells generated under control conditions or in PCs, a low level of ZIC3 protein was observed in PCs. OCT4 and SOX2 are the major transcription factors that bind to the NANOG promoter and promote its transcription and that of related gene networks (Boyer et al., "Core Transcriptional Regulatory Circuitry in Human Embryonic Stem Cells," *Cell* 122:947-956 (2005); Loh et al., "The Oct4 and Nanog Transcription Network Regulates Pluripotency in Mouse Embryonic Stem Cells," *Nat. Genet.* 38(4):431-440(2006), which are hereby incorporated by reference in their entirety), In the SF but not SC cultures, treatment with VPA led to the upregulation of NANOG, suggesting a possible functional interaction between SOX2 and OCT4 (Table 3).

TABLE 3

Expression of Pluripotency Genes

| Pluripotency Gene | SC Cultures | | SF Cultures | |
|---|---|---|---|---|
| | Control | VPA | Control | VPA |
| SOX2 | 7.4 ± 4.4 | 3.9 ± 1.9$^A$ | 4.9 ± 1.5 | 23.1 ± 6.5$^A$ |
| OCT4 | 7.2 ± 7.6 | 8.2 ± 1.7$^A$ | 2.5 ± 1.2 | 32.9 ± 3.8$^A$ |
| NANOG | 7.6 ± 2.2 | 5.6 ± 1.4$^A$ | 8.5 ± 1.8 | 57.6 ± 6.8$^A$ |

Expression of SOX2, OCT4, and NANOG as evaluated by mAb staining and flow cytometric analysis in CD34+ cells (purity: 95%-99%) re-isolated from control cultures and cultures treated with VPA in SF and SC media for 7 days. Each number represents the percentage of CD34+ cells expressing a particular pluripotency protein. Mean ± SEM.
$^A$P < 0.05. ANOVA, P < 0.0001. n = 4.

Figure 9C:
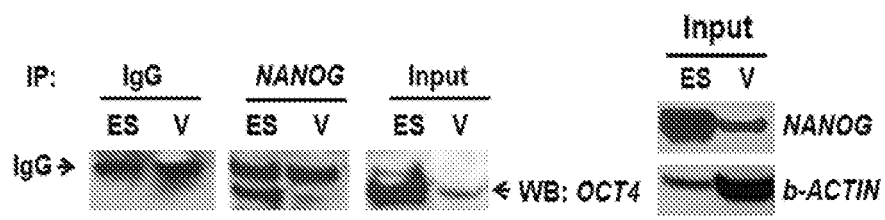
Figure 10A:
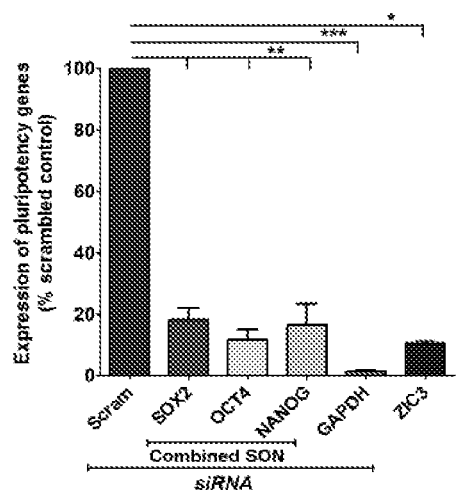
FIGS. 10A-E show the results of siRNA-mediated knockdown of the pluripotency genes.
Figure 10B:
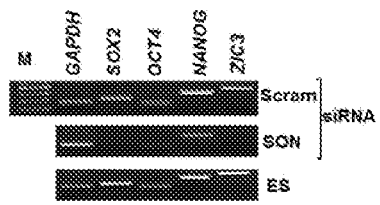
Figure 10C:
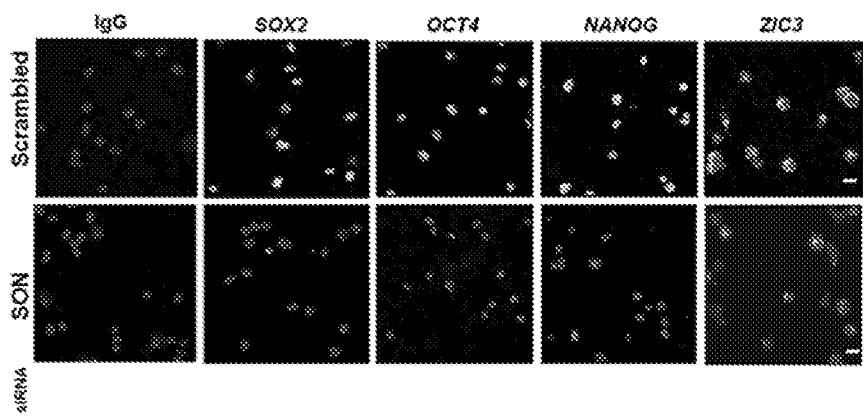
Figure 10D:
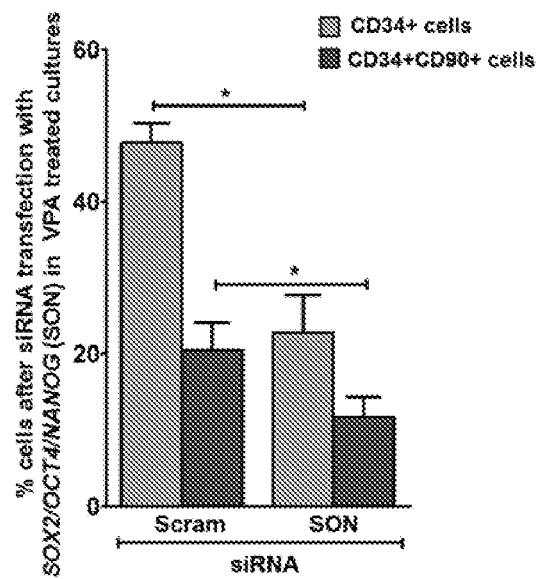
Figure 10E:
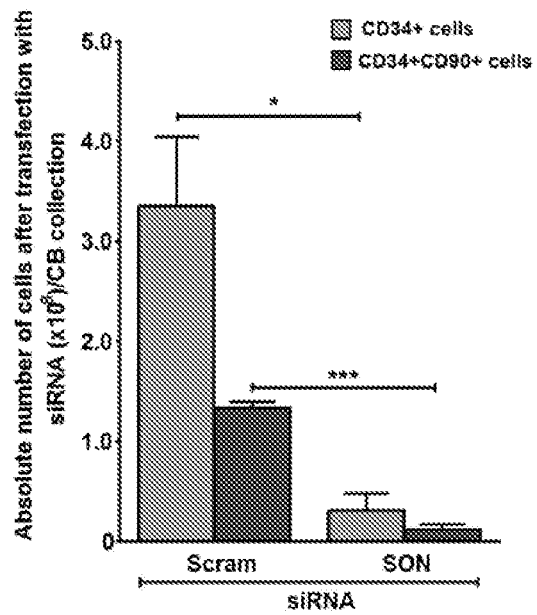

The physical interaction between NANOG and OCT4 was then documented by co-IP of proteins from VPA-treated cells (FIG. 9C). Furthermore, Western blot analysis revealed that endogenous OCT4 and NANOG were expressed less abundantly in WA-treated cells than in ES cells (FIG. 9C), Pluripotency Genes are Essential for Expansion of CD34+ CD90+ Cells To establish a functional link between the upregulation of pluripotency genes in VPA-treated cultures and the expansion of CD34+CD90+ CD34+ cells were transfected either with individual siRNA or with a combined pool of siRNA directed against SOX2, OCT4, and NANOG (SON). Initially, different concentrations of siRNA were tested for the individual genes and their potential toxic effects on cells in control cultures or cultures treated with VPA. The morphological appearance of cells treated with SON siRNA was not altered as compared with those treated with scrambled siRNA. There was no observation of a significant reduction in the total number of cells generated in control cultures and WA-containing cultures after transfection with scrambled, SON, and GAPDH siRNA (Table 8). Pluripotency gene expression was monitored after siRNA transfection in VPA-treated cultures using qPCR and RT-PCR (FIGS. 10A and 10B). siRNA-mediated knock-down led to markedly reduced expression of the transcripts (80%-84%) for SOX2, OCT4, NANOG, and ZIC3 (ANOVA, P<0.0001). Confocal microscopy and mAb staining also revealed a marked reduction in SOX2, OCT4, and NANOG protein expression. Expression of ZIC3 protein, which is downstream of the OCT4, SOX2, and NANOG regulatory network, was reduced to a lesser extent (FIG. 10C). A significant reduction in the percentage of CD34+ (47.8%±4.4% versus 22.8%±8.6%) and CD34+CD90+ (20.5%±6.1% versus 11.7%±4.5%) (ANOVA, P=0.0005) cells was observed after treatment with SON siRNA as compared with individual siRNAs specific for each of the pluripotency genes or with scrambled siRNA (FIG. 10D). Furthermore, after treating VPA-treated CD34+ cells with SON siRNA, an 89.1% and 88.7% reduction in the absolute number of CD34+ and CD34$^+$CD90+ cells per CB collection, respectively (ANOVA, P=0.0008), was observed (FIG. 10E).

These data indicate that VPA treatment leads to an epigenetic reprogramming of cultured CD34+ cells that directs subsequent transcriptional activation of pluripotency genes, which is essential for the generation of CD34+ and CD34+ CD90+ cells in SF cultures.

TABLE 8

Effects of siRNA Transfection on the Control Culture and VPA Treated Culture

| siRNA | (Control culture) Total number of cells/well | (Control culture) CD34+CD90+ cells (%) |
|---|---|---|
| 1. No transfection | 6.6 × 10$^6$ ± 1.5 × 10$^{6*}$ | 17.1 ± 7.8* |
| 2. Scrambled | 6.6 × 10$^6$ ± 1.6 × 10$^{6*}$ | 16.7 ± 4.7* |
| 3. GAPDH | 6.3 × 10$^6$ ± 2.0 × 10$^{6*}$ | 18.3 ± 3.5* |
| 4. SON (SOX2, OCT4, and NANOG) | 5.9 × 10$^6$ ± 2.0 × 10$^{6*}$ | 21.2 ± 2.5* |

| siRNA | (VPA culture) Total number of cells/well | (VPA culture) CD34+CD90+ cells (%) |
|---|---|---|
| 1. No transfection | 4.0 × 10$^6$ ± 0.4 × 10$^{6*}$ | 78.6 ± 2.0* |
| 2. Scrambled | 3.9 × 10$^6$ ± 0.5 × 10$^{6*}$ | 76.0 ± 2.4* |
| 3. GAPDH | 3.3 × 10$^6$ ± 0.8 × 10$^{6*}$ | 75.0 ± 1.7* |
| 4. SON (SOX2, OCT4, and NANOG) | 3.4 × 10$^6$ ± 0.5 × 10$^{6*}$ | 73.2 ± 3.5* |

Upper panel: Control cultures were transfected with siRNA as previously described for VPA cultures. No significant difference in the total cell numbers and percent of CD34+ CD90+ cells was observed following 72 hrs after transfection with Scrambled and SON siRNA. (n = 4) (*p ≤ 0.5, ns)

Lower panel: VPA treated cultures were transfected with Scrambled and GAPDH siRNA as previously described in the Methods section, No significant difference in the cell number or percent of CD34+CD90+ cells was observed following 72 hrs after GAPDH siRNA transfection. (n=3) (*p<0.25, ns)

In Vivo Functional Behavior of VPA-Treated CD34$^+$ Cells in NSG Mice

Figure 11A:
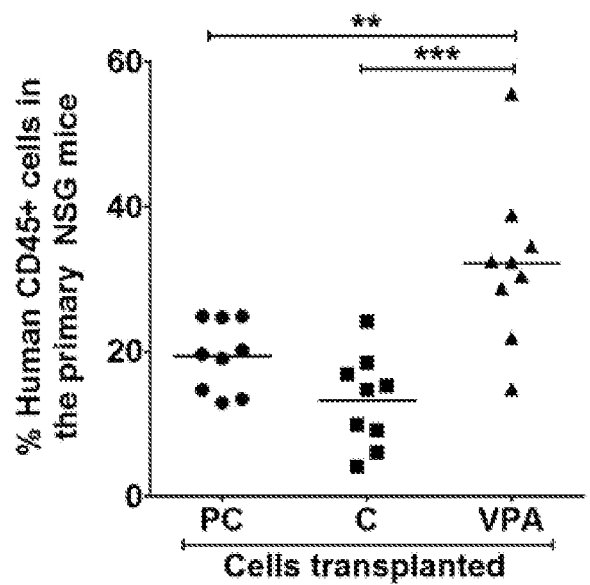
FIGS. 11A-F show the results of analysis of human cell chimerism in Primary NSG mice. NSG mice were transplanted with primary cells (PC), CD34+ cells re-isolated from control cultures and cultures containing VPA. The mean±SD percentage chimerism with (FIG. 11A) human cells (CD45+), (FIG. 11B) CD34+CD45+ cells, (FIG. 11C) CD34+CD184+ cells, (FIG. 11D) CD33+ cells, and (FIG. 11E) megakaryocytes (CD41+), erythroid cells (Glycophorin A (GPA+)), granulocytes (CD14+), T cells (CD3+) and B cells (CD19+) was determined by flow cytometry.
Figure 11B:
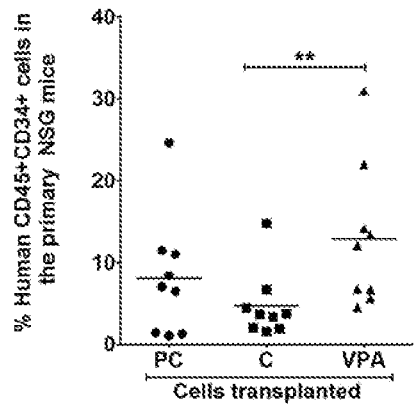

The marrow-repopulating potential of PC and CB CD34+ cells cultured under control conditions and with VPA and cytokines was evaluated by assessing their engraftment within the marrow of NSG recipient mice. In all recipient mice, irrespective of the type of graft transplanted, human CD45+ and CD45+CD34+ cells were detected. Thirteen to 14 weeks after trans-plantation (FIGS. 11A and 11B), 19.4%±4.9% of the marrow cells were donor-derived. CD45+ cells in mice receiving PCs as compared with 13.2%±6.4% in mice receiving cells from control cultures. By contrast, transplantation of VPA-treated CB CD34+ cells resulted in a greater degree of human CD45+ cell chimerism (32.2%±11.3%) and CD45+CD34+ cells (13.0%±8.7%) compared with that achieved with control cells (P=0.0008 and P=0.004, respectively) (FIGS. 11A and 11B), The degree of CD45+ cell chimerism with VPA grafts was also statistically greater than that achieved with PCs (P=0.006).

Figure 11C:
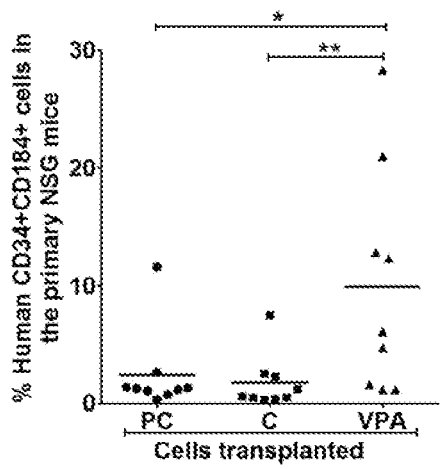
Figure 11D:
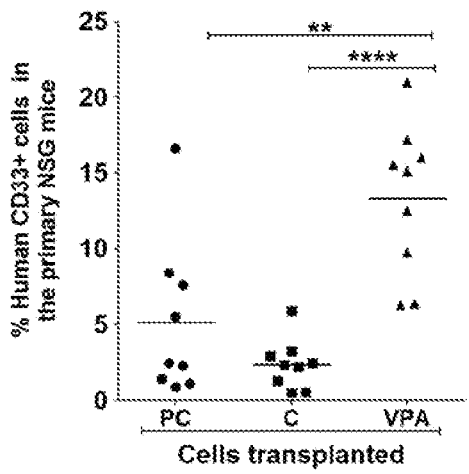
Figure 11E:
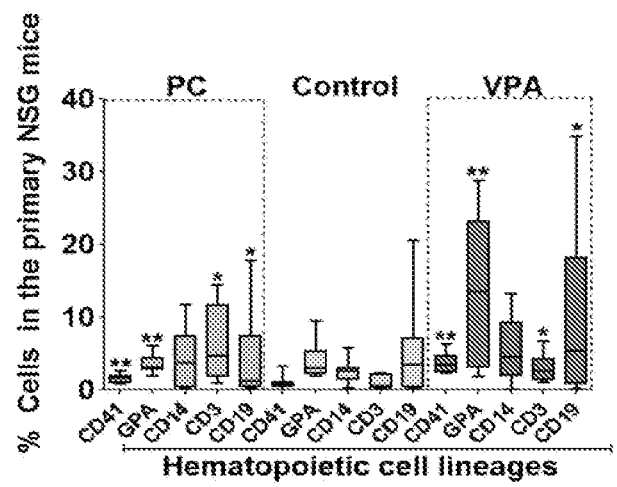

A significantly greater number of donor-derived CD34+ cells within the marrow of mice receiving VPA-treated CD34+ cells coexpressed CD184 (9.9%±9.6%) as compared with the marrow of mice receiving PCs or grafts expanded under control conditions (ANOVA, P=0.01) (FIG. 11C), The pattern of VPA-treated CD34+ cell grafts differentiating into multiple hematopoietic lineages following transplantation was distinctly different from that in PCs or cells expanded under control conditions (ANOVA, P<0.0001) (FIGS. 11D and 11E), with higher proportions of CD41+, CD19+, and glycophorin A-positive (GPA+) cells appearing in mice receiving VPA-treated grafts.

Figure 11F:
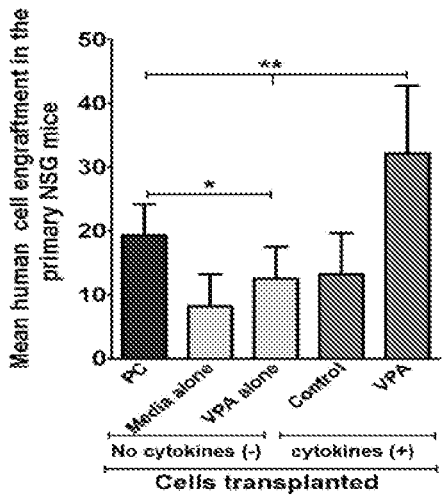

The dependence of VPA-mediated SRC expansion was next evaluated on the continued exposure to cytokines during their generation. As can be seen in FIG. 11F, the transplantation of CD34+ cells cultured in media alone (no cytokines) in the absence of cytokines and with VPA alone (no cytokines) achieved a similar degree of chimerism. (8.2%±5.0% versus 12.5%±5.0%; P=0.1, NS). The grafts generated in the absence of continued cytokine exposure retained the ability to generate cells belonging to multiple hematopoietic lineages (Table 9).

TABLE 9

In vivo Functional Behavior of VPA-Treated CD34+ Cells Cultured Under Serum-Free (SF) Conditions Without Cytokines in NOD/SCID/yc$^{null}$ (NSG) Mice
% Human Cell Engraftment in Primary NSG Mice

|  | CD45 | CD33 | CD34 | CD19 | CD14 | GPA | CD41 |
|---|---|---|---|---|---|---|---|
| PC (n = 5) | 19.4 ± 4.8 | 4.5 ± 6.8 | 7.4 ± 1.9 | 5.7 ± 3.3 | 6.6 ± 1.6 | 3.7 ± 0.7 | 1.2 ± 0.2 |
| Media Alone (n = 5) | 8.2 ± 2.2 | 0.7 ± 0.2* | 0.76 ± 0.2* | 5.2 ± 1.6 | 5.4 ± 1.3* | 9.9 ± 2.2 | 0.62 ± 0.6 |
| VPA Alone (N = 5) | 12.5 ± 2.2 | 3.5 ± 0.6* | 1.6 ± 0.4* | 1.9 ± 1.1 | 2.1 ± 0.2* | 9.8 ± 0.8 | 0.90 ± 0.6 |

Bone marrow analysis of NSG mice receiving 2.0 × 10$^5$ primary CB CD34+ cells (PC) or CD34+ cells re-isolated after 7 days from cultures containing media alone (no cytokines) and cultures containing VPA alone (no cytokines) under serum-free (SF) conditions. The percentage of human cell chimerism (CD45+, CD33+, and CD34+) and multilineage hematopoietic cell engraftment including B cells (CD19+), granulocytes (CD14+), erythroid cells (Glycophorin A (GPA+)) and megakaryocytes (CD41+) after 12-13 weeks of transplantation is shown. (Mean ± SE, *p < 0.05, (ANOVA P < 0.0001).
NSG mice recipients (n = 15).

The degree of donor cell chimerism achieved with the transplantation of cells cultured under control conditions was similar to that achieved with cells that were not exposed to cytokines throughout the 7-day period in media alone (no cytokines) or VPA alone (no cytokines) A dramatic increase in the degree of human cell chimerism was, however, observed following the transplantation of grafts generated in the presence of cytokines plus VPA (32.3±10.2% ANOVA, P<0.0001). These data suggest that SRCs persist if PCs are primed with cytokines for merely 16 hours and are then cultured in media alone or with VPA alone in the absence of cytokines. The presence of cytokines throughout the culture period, however, further enhanced the effectiveness of VPA, resulting in a higher degree of human cell chimerism NSG recipients.

Figure 12A:
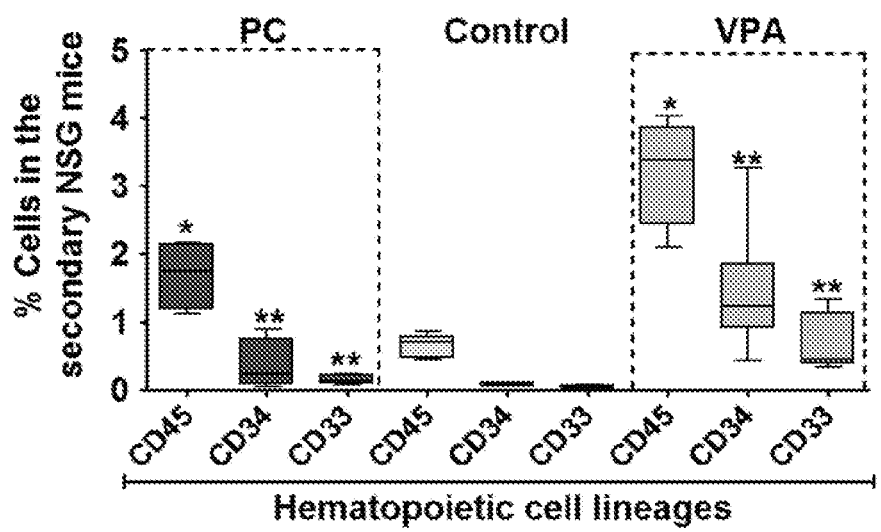
FIGS. 12A-B show the results of analysis of human cell chimerism in secondary NSG mice. 13-14 weeks after transplantation of primary CB CD34+ cells (PC) or grafts expanded for 7 days under the various conditions previously described, the primary recipient mice were sacrificed and $2\times10^6$ BM cells were transplanted into secondary NSG mice. Each bar represents the median percent of human donor cell engraftment occurring in the marrows of the secondary NSG mice as determined by monoclonal antibody staining and flow cytometric analysis and (FIGS. 12A and 12B) multilineage hematopoietic cell engraftment occurring in secondary NSG mice 15-16 weeks after transplantation of different types of grafts from primary recipients. 2-3 mice were present in each group. The patterns of lineage development were statistically significantly different $*P<0.05$, $**p<0.005$, (median±SD, FIG. 12A and FIG. 12B (ANOVA, p<0.0001)), NSG recipients (n=18).
Figure 12B:
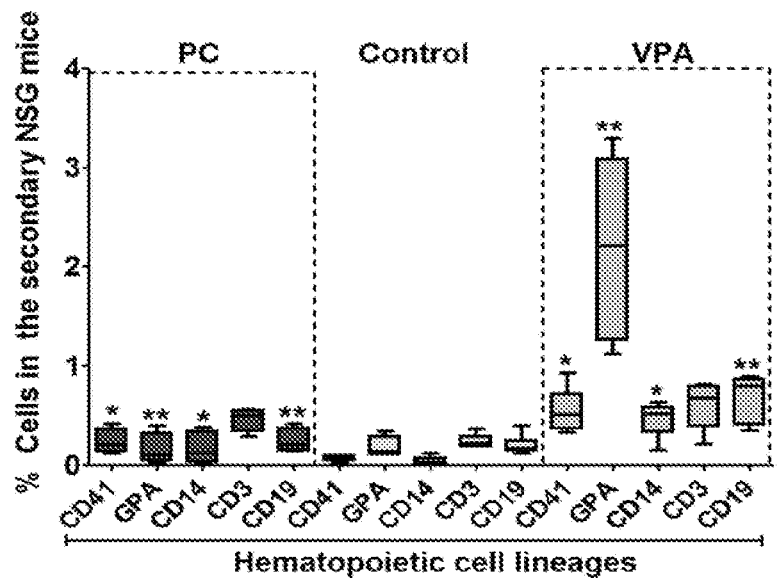
Figure 17:
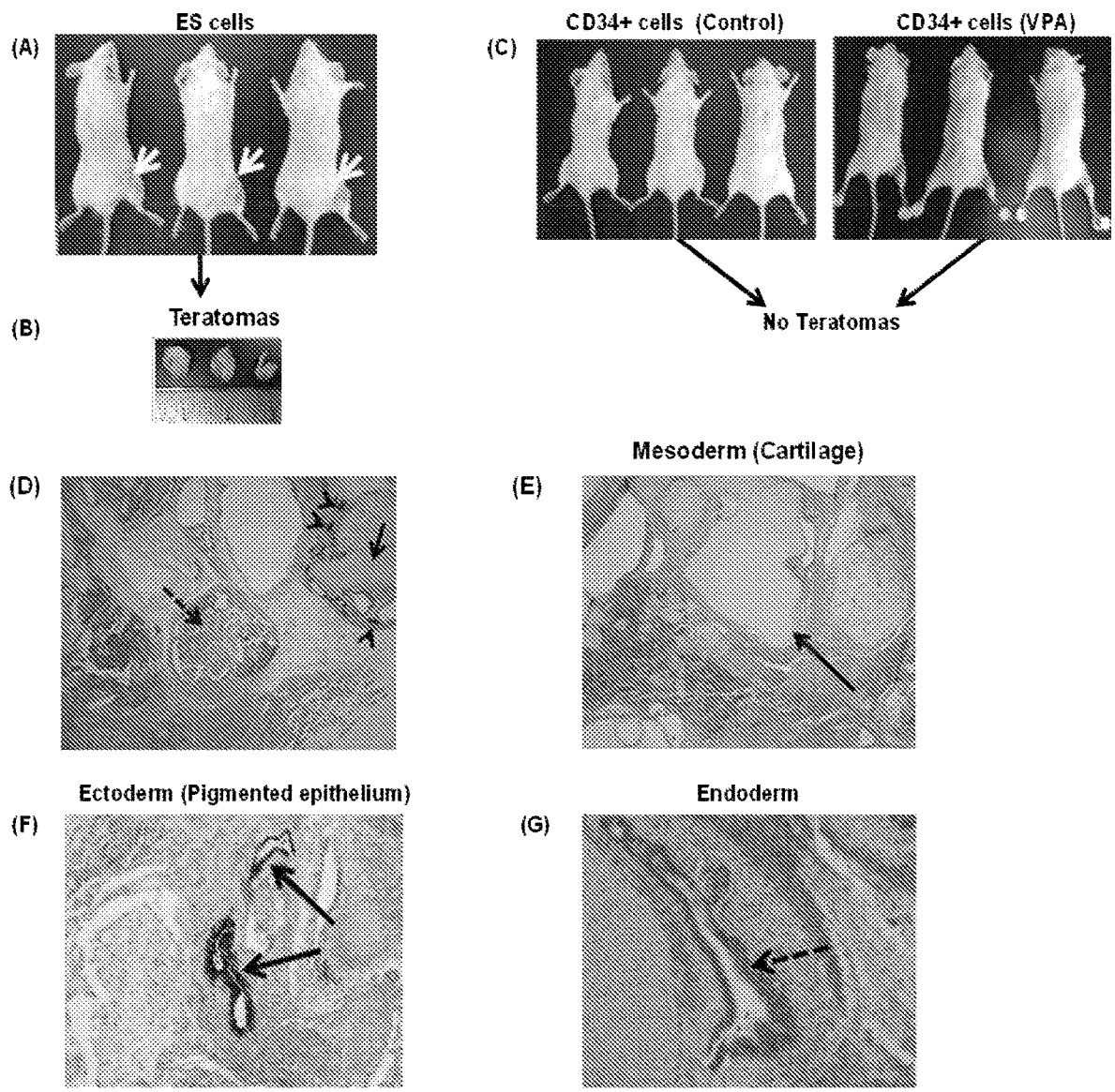
FIGS. 17A-G show the results of a teratoma formation assay. 1×10$^6$ of ES (H9) cells or CD34+ cells that were re-isolated from control cultures or cultures containing VPA were mixed with Matrigel and injected subcutaneously into the right hind limb of NSG mice (n=9). After 8 weeks, the mice were sacrificed and the masses were dissected, fixed, and stained with hematoxylin and eosin.

The self-renewal potential of the expanded grafts was evaluated by transplanting donor-derived cells present in primary recipients into secondary recipients. After 15 to 16 weeks, secondary recipients transplanted with marrow cells from primary recipients that had been transplanted with CB CD34+ cells treated with VPA achieved the greatest degree of human CD45+ cell chimerism (ANOVA, P<0.0001) (FIG. 12A). As shown in FIG. 12B, the donor-derived cells in the secondary recipient mice belonged to multiple hematopoietic lineages, and this pattern was distinct from that observed in secondary recipients receiving marrow cells from primary recipients that received PC grafts or grafts expanded under control conditions (ANOVA, P<0.0001). The degree of donor-derived erythroid engraftment was especially notable in the secondary recipients of marrow cells from mice receiving VPA-treated grafts (FIG. 12B) (Sauvageau et al., "In vitro and In vivo Expansion of Hematopoietic Stem Cells," Oncogene 23:7223-7232 (2004), which is hereby incorporated by reference in its entirety), None of the primary or secondary recipients of marrow cells receiving VPA-treated grafts developed evidence of blood cancer or developed teratomas. To further exclude the possibility of teratoma formation, CD34+ cells re-isolated from control cultures or VPA-containing cultures or ES cells were each subcutaneously injected into the hind limb of NSG mice and were evaluated after 8 weeks. Teratomas, composed of cells derived from three different germ layers, were observed exclusively in animals injected with the ES cells (FIG. 17).

In order to evaluate the persistence of the upregulation of pluripotency genes following VPA treatment, the expression of these genes in donor cells was evaluated in primary and secondary recipient NSG mice. Using qPCR, no transcripts for pluripotency genes were detected, including SOX2, OCT4, NANOG, and ZIC3 in the marrow cells of the primary and secondary recipients, indicating that the VPA-induced upregulation was transient.

Figure 13A:
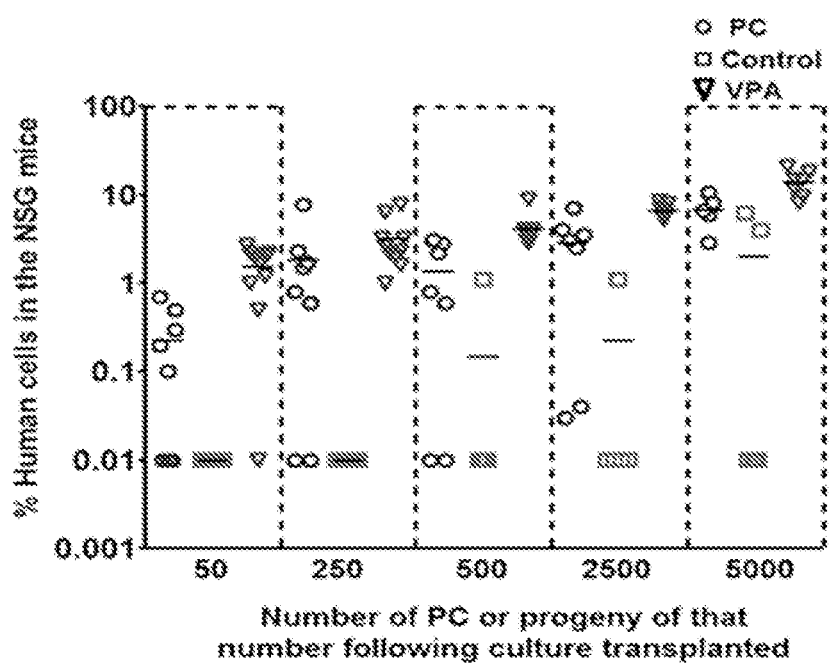
FIGS. 13A-C show results of a comparison of the frequency of SCID repopulating cells (SRC) present in primary CB CD34+ cells (PC) and the progeny of an equivalent number of CD34+ cells cultured under control conditions or treated with VPA.
Figure 13B:
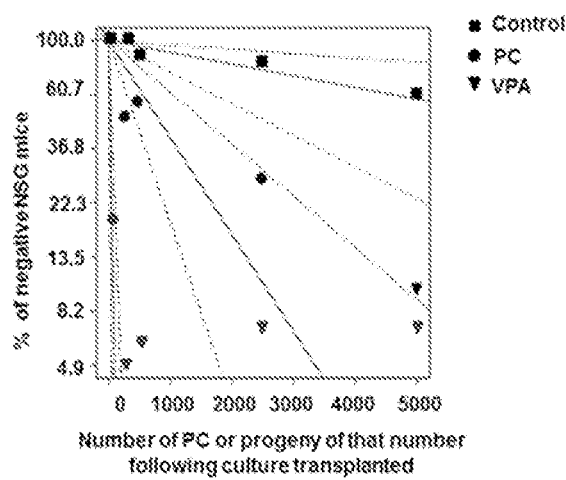

To assess the degree of HSC expansion achieved with VPA treatment, limiting dilution analysis was used to compare the frequency of SRCs in PCs, in cells derived from an equivalent number of PCs cultured under control conditions, or in cultures containing VPA. The transplantation of increasing numbers of PCs (50, 250, 500, 2,500, and 5,000) or the progeny of cells from an equivalent number of PCs after treatment under control conditions and with VPA resulted in increasing degrees of human cell chimerism following their transplantation (FIG. 13A). Poisson distribution analysis revealed an SRC frequency of 1 in 1,115 (95% CI: 1/596 to 1/2,087) in PCs, 1 in 9,223 (95% CI: 1/3,419 to 1/24,879) in control cultures, and 1 in 31 (95% CI: 1/14 to 1/66) in cultures treated with VPA. The overall difference in stem cell frequencies between PC, control, and VPA-containing cultures was highly significant (P=9.42× 10−29), indicating the effective expansion of SRC numbers within VPA cultures (FIG. 13B and Tables 4 and 5) as compared with PC or control cultures.

TABLE 4

Limiting Dilution Analysis of Human Cell Engraftment in NSG Mice

| Culture Conditions | Number of cells transplanted | | No. of mice with human cell chimerism/total number of mice transplanted |
|---|---|---|---|
| | Cells Transplanted | | |
| PCs (uncultured) | 50 | | 0/8 |
| | 250 | | 4/8 |
| | 500 | | 3/7 |
| | 2,500 | | 5/7 |
| | 5,000 | | 5/5 |
| | Number of CD34+ cells to initial culture | | |
| Control | 50 | $1.2 \times 10^4 \pm 4.4 \times 10^2$ | 0/8 |
| | 250 | $5.8 \times 10^4 \pm 2.2 \times 10^3$ | 0/8 |
| | 500 | $1.2 \times 10^5 \pm 4.4 \times 10^3$ | 1/8 |
| | 2,500 | $5.8 \times 10^5 \pm 2.2 \times 10^4$ | 1/5 |
| | 5,000 | $1.2 \times 10^6 \pm 4.4 \times 10^4$ | 2/5 |
| VPA | 50 | $1.0 \times 10^4 \pm 2.3 \times 10^2$ | 8/10 |
| | 250 | $5.2 \times 10^4 \pm 1.2 \times 10^3$ | 10/10 |
| | 500 | $1.0 \times 10^5 \pm 2.3 \times 10^3$ | 8/8 |
| | 2,500 | $5.2 \times 10^5 \pm 1.2 \times 10^4$ | 7/7 |
| | 5,000 | $1.0 \times 10^6 \pm 2.3 \times 10^4$ | 7/7 |

Summary of the frequency of SRCs present in the BM of NSG mice. PCs and the progeny of an equivalent number of PCs cultured under control conditions or with VPA for 7 days were transplanted into NSG mice. After 12 to 13 weeks, the BM were analyzed for human CD45+ cell engraftment.

Figure 13C:
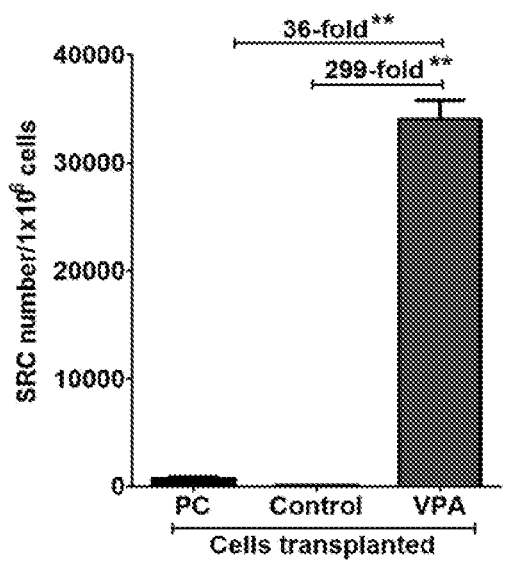

The presence of 897 SRCs and 108 SRCs in $1 \times 10^6$ PCs, and cells cultured under control conditions were calculated, respectively. By contrast, the presence of 32,258 SRCs in $1 \times 10^6$ cells from VPA-containing cultures (Table 5) was calculated. Therefore, incubation of PCs under control culture conditions led to a reduction in SRC numbers, while VPA treatment resulted in a 36-fold (P≤0.002) increase in the number of SRCs compared with that in PCs and a 299-fold (P≤0.002) increase in the number of SRCs compared with that in cells cultured under control conditions (FIG. 13C).

TABLE 5

Frequency of SRC

| Culture Conditions | SRC frequency in starting cells | 95% CI | No. of SRCs generated per $1 \times 10^6$ CD34+ starting cells | SRC frequency in total no. of cells transplanted | 95% CI |
|---|---|---|---|---|---|
| PCs (uncultured) | $1/1,115^A$ | 1/596 to 1/2,087 | 897 | 1/1,115 | 1/596 to 1/2,087 |
| Control | $1/9,223^A$ | 1/3,419 to 24,879 | 108 | 1/2,137,058 | 1/792,186 to 1/5,765,084 |
| VPA | $1/31^A$ | 1/14 to 1/66 | 32,258 | 1/6,375 | 1/2,986 to 1/13,613 |

The frequency of SRC was determined by applying Poisson statistics from the data provided in Table 4 (L-Cale software from STEMCELL Technologies and ELDA software). Overall differences in stem cell frequencies between any of the groups including PCs, control, and VPA ($^A$P = 9.42 × 10$^{-29}$).

DISCUSSION

The multipotent nature of HSCs can be accounted for by the dynamic maintenance of HSC chromatin structure and epigenetic plasticity. The modification of chromatin structure is largely regulated by specific post-translational modifications of histones, which determine whether the resultant chromatin structure is permissive or repressive (Cedar et al., "Epigenetics of Haematopoietic Cell Development," Nat. Rev. Immunol. 11:478-488 (2011); Kouzarides, "Chromatin Modifications and Their Function," Cell 128:693-705 (2007); Oh et al., "Concise Review: Multidimensional Regulation of the Hematopoietic Stem Cell State," Stem Cells 30:82-88 (2012), which are hereby incorporated by reference in their entirety). The progressive loss of stem cell function by CB CD34+ cells following in vitro culture using SC culture conditions and cytokine combinations remains a barrier to the in vitro expansion of the numbers of transplantable HSCs (Giebel et al., "Primitive Human Hematopoietic Cells Give Rise to Differentially Specified Daughter Cells Upon their Initial Cell Division," Blood 107(5): 2146-2152 (2006); Ho et al., "The Beauty of Asymmetry: Asymmetric Divisions and Self-Renewal in the Haematopoietic System," Curr. Opin. Hematol. 14(4):330-336 (2007); Huang et al., "Symmetry of Initial Cell Divisions Among Primitive Hematopoietic Progenitors Is Independent of Ontogenic Age and Regulatory Molecules," Blood 94(8): 2595-2604 (1999); Srour et al., "Modulation of In vitro Proliferation Kinetics and Primitive Hematopoietic Potential of Individual Human CD34+CD38-/lo Cells in G0," Blood 105(8):3109-3116 (2005), which are hereby incorporated by reference in their entirety). This decline of stem cell function is likely due to the removal of fully functional HSCs from a permissive environment that exists within the host and their placement into a hostile ex vivo environment, which leads to epigenetic modifications that alter the gene expression program that determines the critical functions of a stem cell, including self-renewal potential, marrow-repopulating capacity, and multilineage differentiative capacity. This loss of HSC function has been attributed to the rapid cell cycling and cell division that occur in response to the culture conditions used (Declercq et al., "Zic3 Enhances the Generation of Mouse induced Pluripotent Stem Cells," Stem Cells Dev. (2013); Sauvageau et al., "In vitro and In vivo Expansion of Hematopoietic Stem Cells," Oncogene 23:7223-7232 (2004); Walasek et al., "Hematopoietic Stem Cell Expansion: Challenges and Opportunities," Ann. NY Acad. Sci. 1266:138-150 (2012), which are hereby incorporated by reference in their entirety). Prior attempts at ex vivo stem cell expansion have met with limited success, due perhaps in part to their focus on creating a milieu that resembles the hematopoietic microenvironment and thereby favors retention of stem cell functional integrity (Dahlberg et al., "Ex vivo Expansion of Human Hematopoietic Stem and Progenitor Cells," Blood 117:6083-6090 (2011); Delaney et al., "Cord Blood Graft Engineering," Biol. Blood Marrow Transplant 19(1): S74-S78 (2013); Delaney et al., "Strategies to Enhance Umbilical Cord Blood Stem Cell Engraftment in Adult Patients," Expert Rev. Hematol. 3:273-283 (2010), which are hereby incorporated by reference in their entirety). The difficulty of creating such a microenvironment ex vivo is appreciated; the alternative approach of attempting to directly maintain the epigenetic characteristics of HSCs using agents that affect chromatin structure has been taken. This approach was based on the understanding that dynamic changes in chromatin states are mediated by nucleosome remodeling, DNA methylation, and histone acetylation (Cedar et al., "Epigenetics of Haematopoietic Cell Development," *Nat. Rev. Immunol.* 11:478-488 (2011); Kouzarides, "Chromatin Modifications and Their Function," *Cell* 128:693-705 (2007); Oh et al., "Concise Review: Multidimensional Regulation of the Hematopoietic Stem Cell State," *Stem Cells* 30:82-88 (2012); Elizalde et al., "Histone Deacetylase 3 Modulates the Expansion of Human Hematopoietic Stem Cells," *Stem Cells Dev.* 21:2581-2591 (2012), which are hereby incorporated by reference in their entirety). For this purpose, in this study several HDACIs were evaluated that are capable of inhibiting both class I and II HDACs, with the aim of achieving decondensation of the chromatin structure that harbors genes involved in retaining stem cell function following repeated cell division. HDAC1, HDAC3, and HDAC5 proteins were uniformly reduced by the three most active HDACIs, suggesting that a combination of these three HDACs plays a critical role in stem cell fate decisions that favor retention of stem cell function following division in vitro.

It has been previously reported that HDACI treatment leads to increased H3 histone acetylation (Chaurasia et al., "Chromatin-Modifying Agents Promote the Ex vivo Production of Functional Human Erythroid Progenitor Cells," *Blood* 117:4632-4641 (2011), which is hereby incorporated by reference in its entirety), while others have indicated that exposure to such agents results in the loss of repressive modifications either by binding to HDACs and/or by promoting DNA demethylation and sliding and/or displacement of nucleosomes, which may allow transcription factors to bind to related DNA, or by polyubiquitination, which leads to proteasomal degradation of particular HDACs (Cedar et al., "Epigenetics of Haematopoietic Cell Development," *Nat. Rev. Immunol.* 11:478-488 (2011); Kouzarides, "Chromatin Modifications and Their Function," *Cell* 128:693-705 (2007); Oh et al., "Concise Review: Multidimensional Regulation of the Hematopoietic Stem Cell State," *Stem Cells* 30:82-88 (2012), which are hereby incorporated by reference in their entirety). These interactions permit the recruitment of additional coactivators and/or histone-modifying enzymes that are required to form transcriptional machinery, leading to transcriptional activation (Cedar et al., "Epigenetics of Haematopoietic Cell Development," *Nat. Rev. Immunol.* 11:478-488 (2011); Kouzarides, "Chromatin Modifications and Their Function," *Cell* 128:693-705 (2007); Oh et al., "Concise Review: Multidimensional Regulation of the Hematopoietic Stem Cell State," *Stem Cells* 30:82-88 (2012), which are hereby incorporated by reference in their entirety). It is reported here that VPA was the most effective of all the HDACIs evaluated in generating cells capable of producing the greatest degree of human cell chimerism following their transplantation into primary and secondary NSG mice. VPA treatment led to a 36-fold increase in SRC frequency as compared with that of PCs, while retaining the high proliferative potential and multilineage differentiation capacity characteristic of HSCs. The use of SF rather than SC culture conditions was shown to be critical for efforts to generate functional HSCs. VPA treatment under SF culture conditions resulted in the generation of 20,202-fold greater numbers of CD34+CD90+ cells than did VPA treatment under SC conditions. These findings indicate that serum contains factors that inhibit or repress the regulatory genes involved in the retention and/or expansion of functional HSCs and that the presence of serum favors the upregulation of genes involved in commitment and differentiation. These findings are remarkably similar to those reported by Hirai and coworkers, who showed that the efficiency of creating iPS cells can be drastically improved by changes in the composition of the culture media and the density at which transduced cells are seeded on feeder layers (Hirai et al., "Efficient iPS Cell Production with the MyoD Transactivation Domain in Serum-Free Culture," *PLoS One* 7(3):e34149 (2012), which is hereby incorporated by reference in its entirety). It has also been shown that VPA treatment under SF culture conditions led to the persistent division of a higher fraction of dividing CD34+CD90+ cells after 7 days of incubation, thereby accounting for the expansion of CD34+ CD90+ cell numbers. These findings indicate that VPA treatment results in the retention of the ability of CD34+CD90+ cells to continue dividing even over a 7-day culture period. This characteristic was, however, lost after more prolonged periods of incubation, which is likely indicative of the transient retention of a stem cell-defining gene expression program ex vivo under the conditions used. The primitive nature of the CB CD34+ cells generated using SF conditions and VPA treatment was further documented in this study by the greater degree of CD184 and integrin α6 (CD49f) expression, the lack of CD45RA expression, and the increased degree of ALDH activity. The increased expression of CXCR4 is of particular importance, since the interaction of CXCR4 with its ligand SDF1 plays a critical role in the horning of stem cell grafts to the marrow of transplanted recipients (Motabi et al., "Advances in Stem Cell Mobilization," *Blood Rev.* 26(6):267-278 (2012), which is hereby incorporated by reference in its entirety).

The functionality of upregulated CD184 in VPA-treated CD34+ cells was documented in this study by the ability of these cells to migrate in vitro in response to SDF1 and to home to the marrow of NSG mice to a greater degree than CD34+ cells from control cultures. The enhanced marrow-repopulating potential of VPA-treated CB CD34+ cells can, therefore, be attributed to its effects not only on HSC generation, but also on promoting HSC horning to the marrow of recipient mice. It was found that the VPA-treated CD34+ cells were also characterized by upregulation of the pluripotency-associated genes SOX2, OCT4, NANOG, and ZIC3, but not hTERT. These properties of VPA-treated CD34+ cells are characteristic of IPS cells and ES cells and have not been previously associated with normal HSCs. The knockdown of these pluripotency genes (SOX2, OCT4, and NANOG) was demonstrated to impair the ex vivo generation of CD34+CD90+ cells by VPA. In addition, the downregulation of ZIC3 following SON treatment was observed, which is likely a reflection of its contribution to the maintenance of pluripotency by operating downstream of OCT4, SOX2, and NANOG (Lim et al., "Zic3 is Required for Maintenance of Pluripotency in Embryonic Stem Cells," *Mol. Biol. Cell* 18:1348-1358 (2007); Declercq et al., "Zic3 Enhances the Generation of Mouse Induced Pluripotent Stem Cells," *Stem Cells Dev.* (2013), which are hereby incorporated by reference in their entirety). The previous documentation that OCT4 is present in human tumors has been explored by others and has been attributed to OCT4 pseudogenes which lack OCT4 activity (Redshaw et al., "Human haematopoietic Stem Cells Express Oct4 Pseudogenes and Lack the Ability to Initiate Oct4 Promoter-Driven Gene Expression," *J. Negat. Results Biomed* 9(1):2-8 (2010): Zangrossi et al., "Oct-4 Expression in Adult Human Differentiated Cells Challenges its Role as a Pure Stem Cell Marker," *Stem Cells* 25:1675-1680 (2007), which are hereby incorporated by reference in their entirety). Transcripts for these pseudogenes were unable to be detected in VPA-treated cells. The physical interaction of NANOG with OCT4 was further documented by co-IP of these proteins from VPA-expanded cells, which was similar to that observed with ES cells. Interestingly, Yu and coworkers recently reported that OCT4 and SOX2 promote the expression of CD49f in human mesenchymal stem cells, which raises the possibility that many of the phenotypic markers that characterize VPA-treated CD34+ cells are related to the upregulation of these pluripotency genes (Yu et al, "D49f Enhances Multipotency and Maintains Stemness Through the Direct Regulation of OCT4 and SOX2," *Stem Cells* 30(5):876-887 (2012), which is hereby incorporated by reference in its entirety). The VPA-treated CB CD34+ cells were not immortalized and possessed distinctly different biological properties than did iPS and ES cells. Unlike iPS or ES cells, which can be maintained indefinitely in culture, VPA-treated CD34+ cell numbers declined after 8 days of culture. In addition, VPA-treated CD34+ cells did not form teratomas in NSG mice, a characteristic property of ES and iPS cells. The transient expression of these pluripotency genes by VPA-treated CD34+ cells was further documented by the absence of their transcripts in human cells that persisted in primary and secondary recipient NSG mice for a total of 30 weeks. These data indicate that the transient expression of such pluripotency genes induced in VPA-treated CD34+ cells likely influences the function of dividing CB HSCs without leading to their immortalization.

The ability of VPA to alter the phenotype of CB CD34+ cells was dramatically affected by the addition of a combination of cytokines that are known to influence the behavior of primitive cells along the hierarchy of hematopoietic cell differentiation. Unless PCs were at least primed with cytokines for a 16-hour period, HSC numbers declined. The expansion of CD34+ and CD34+CD90+ cell numbers was possible only if these cells were at least cytokine primed and then incubated for an additional 7 days in the presence of media alone (no cytokines) or VPA alone (no cytokines). Only those cells that were exposed to VPA without cytokines during the subsequent 7-day period, however, expressed an HSC phenotype similar to that observed in cultures containing VPA and cytokines (CD34+CD90+CD117+CD49f+ CD184+CD45RA−). Importantly, the degree of expansion of CD34+ cells was further increased substantially when cytokines were added to the VPA for the entire 7-day incubation period. Remarkably, the CD34+ cells generated both in the presence and absence of cytokines retained the ability to establish multilineage hematopoiesis upon their transplantation into NSG mice, indicating that the brief cytokine exposure during the priming phase led to limited proliferation, with preservation of sufficient HSC function for hematological engraftment to occur. These data indicate that the ex vivo environment in which HSCs are placed in part determines their fate and that the retention of the HSC program responsible for its phenotype is a consequence of epigenetic reprogramming due to VPA in SF media, while the increase in cell numbers is a result of cellular proliferation promoted by cytokine exposure.

The studies reported here have important implications fir the clinical pursuit of CB transplantation. The implementation of the approach outlined in this report has the potential to make available stem cell grafts that contain sufficient numbers of SRCs to allow adults to proceed with allogeneic CB stem cell transplantation with more favorable outcomes.

Example 2

Effect of HDACIs on the Absolute Number of BFU-E+CFU-Mix

Figure 20A:
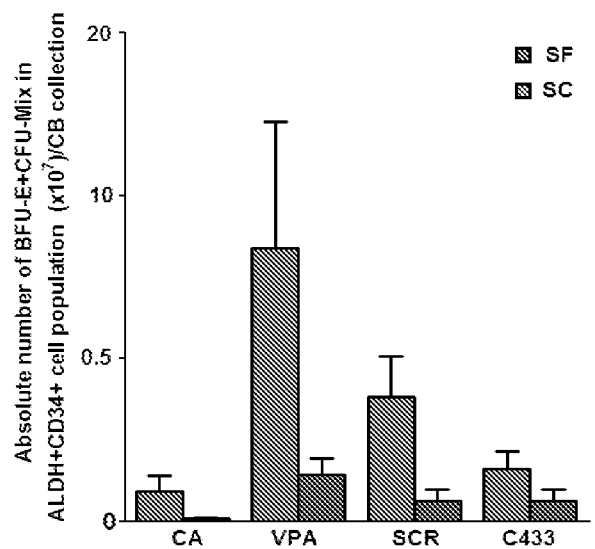
FIGS. 20A-B are graphs showing the effect of HDACIs on the absolute number of BFU-E+CFU-Mix generated from ALDH+CD34+ and ALDH-CD34+ cells: CD34+ cells treated with CA, VPA, SCR, or C433 were stained with Aldefluor and a CD34 monoclonal antibody and sorted on day 7 as described in the Examples below. A far greater number of BFU-E+CFU-Mix were generated from ALDH+ CD34+ cells generated in the presence of each of the HDACI in SF cultures as compared with SC cultures (ANOVA, p=0.001). By contrast, a greater number of BFU-E+CFU-Mix were generated from ALDH-CD34+ cells in SC cultures as compared to SF cultures. Mean±SE, ANOVA, p=0.01 (n=3).
Figure 20B:
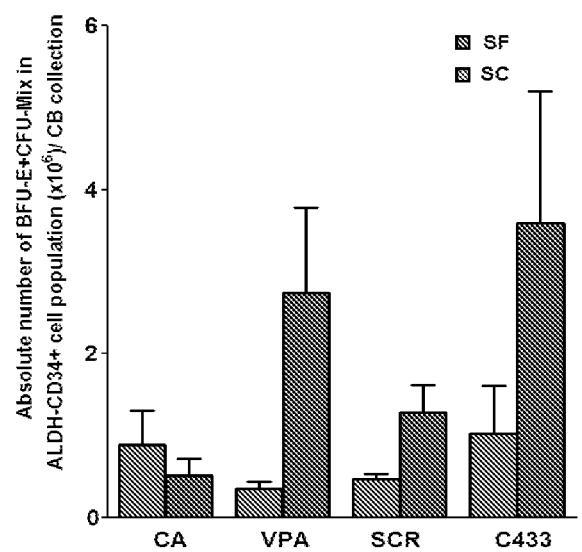

Purified ALDH+CD34+ cells generated using SF cultures supplemented with VPA generated greater absolute numbers of BFU-E and CFU-Mix ($8.4 \times 10^7 \pm 6.7 \times 10^7$/CB collection) as compared to SC cultures ($1.4 \times 10^7 \pm 0.88 \times 10^7$; ANOVA, p=0.001) (FIG. 20A). By contrast, ALDH-CD34+ cells from SC cultures supplemented with VPA generated greater numbers of BFU-E and CFU-Mix ($2.7 \times 10^6 \pm 1.0 \times 10^6$) as compared to SF cultures ($3.5 \times 10^5 \pm 0.78 \times 10^5$) (ANOVA, p=0.01) (FIG. 20B). These data indicate that serum differentially influences the in vitro fate of ALDH+ and ALDH− cell populations.

Example 3

Effect of Cryopreservation on Stem Cell Phenotype

Since it is anticipated that the expanded HSC product will be cryopreserved prior to its delivery to a transplant center, the effects of cryopreservation on the recovery of viable cells expressing the HSC phenotype was explored. CB-CD34+ cells were treated with VPA for 7 days and the cell numbers were enumerated and phenotypic analyses were performed both prior to and post thaw. Cryopreservation was performed using Synth-a-Freeze from Invitrogen (Life Technologies, Grand Island, N.Y.).

Figure 18:
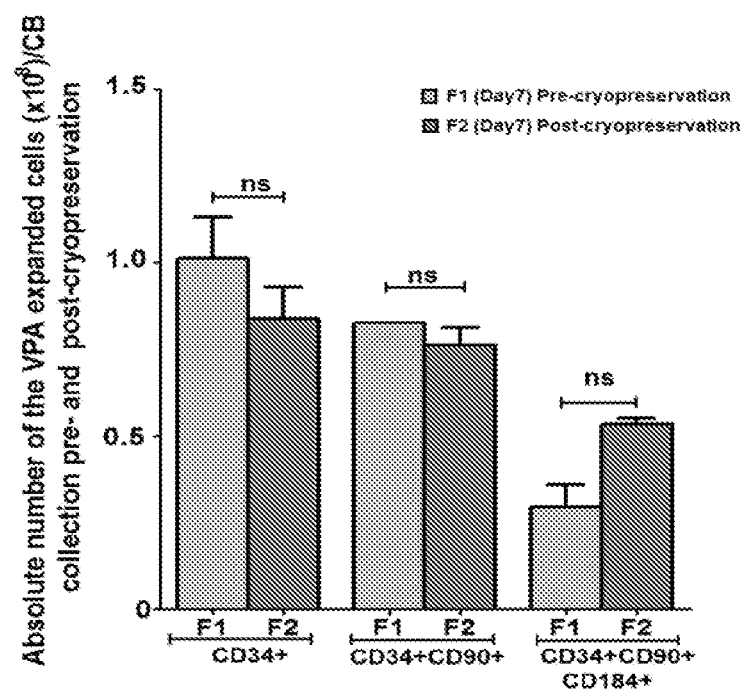
FIG. 18 shows results of the absolute number of CD34+, CD34+CD90+, and CD34+CD90+CD184+ cells: CB-CD34+ cells were treated with VPA for 7 days and phenotypic analysis was performed pre- and post-cryopreservation (5 weeks). ns=not significant. (n=2).

Synth-a-Freeze is a defined, liquid cryopreservation medium containing 10% dimethylsulfoxide (DMSO). Synth-a-Freeze does not contain antibiotics, antimycotics, hormones, growth factors, serum, or proteins. This medium is HEPES and bicarbonate buffered. The percentages of CD34+, CD34+CD90+ and CD34+CD90+CD184+ cells were not altered significantly pre and post cryopreservation (90%-95% cells remained viable). The absolute number of cells expressing these HSC phenotype did not differ pre and post cryopreservation (FIG. 18). These data demonstrate the feasibility of performing the cryopreservation of the expanded HSC product without the need for animal protein.

Example 4

The VPA Expanded HSC Product Contains All Classes Of HSCs as Defined by Phenotype It has been shown that VPA expanded HSCs contain increased numbers of long term repopulating cells. Since these cells express pluripotency genes which are characteristic of totipotent cells, there is a valid concern that such grafts might be associated with delayed engraftment. The Dick laboratory has defined a hierarchy of HSCs that repopulate NSG mice rapidly and after intermediate time periods and long term and has identified their phenotypic hierarchy signature (Notta et al., "Isolation of Single Human Hematopoietic Stem Cells Capable of Long-term Multilineage Engraftment," *Science* 333(6039):218-221 (2011), which is hereby incorporated by reference in its entirety). Rapid SCID repopulating cells (R-SRC) are detected in NSG mice 2-4 weeks after their transplantation and are CD34+CD90−CD49f−, intermediate SRC (IT-SRC) repopulate after 12-14 weeks and are CD34+CD90+CD49f− and long-term SRC (LT-SRC) repopulate >24 weeks and are CD34+CD90+CD49f+. The distribution of these various HSC classes were evaluated in three VPA expanded HSC products. As can be seen in FIGS. 19A-C, each of these classes of HSCs were present in increased numbers in VPA treated cells as compared to primary CB-CD34+ cells suggesting that these expanded grafts will likely lead to more rapid as well as sustained engraftment patterns as well as a lower incidence of graft failure as compared to unmanipulated CB grafts. Interestingly, CB-CD34+ cells that are treated under SF condition in the presence of cytokines alone contain the greatest numbers of R-SRC (FIG. 19C). This intriguing finding might be of importance if after the completion of the phase 1 trial the infusion of the VPA treated graft is not associated with a shorter time to hematopoietic recovery. Based on these findings, a small portion of the primary CD34+ cells could be expanded in the presence of cytokines alone and combined with the VPA treated cell product in order to facilitate more rapid engraftment by increasing to a greater extent the numbers of R-SRC.

All of the features described herein (including any accompanying claims, abstract and drawings), and/or all of the steps of any method or process so disclosed, may be combined with any of the above aspects in any combination, except combinations where at least some of such features and/or steps are mutually exclusive.

What is claimed:

1. A method of producing an enriched population of isolated and expanded human hematopoietic cord blood stem cells, said method comprising:

contacting an isolated population of non-recombinant human hematopoietic cord blood stem cells with cytokines SCF, Flt3 ligand, TPO, and IL-3 in the absence of valproic acid to prime the hematopoietic stem cells;

treating the isolated and primed population of non-recombinant human hematopoietic cord blood stem cells in a serum-free culture system with a single epigenetic regulator, wherein the epigenetic regulator is a histone deacetylase inhibitor and wherein the histone deacetylase inhibitor is valproic acid; and culturing the treated population to produce an enriched population of isolated and expanded non-recombinant human hematopoietic cord blood stem cells, wherein the expanded non-recombinant human hematopoietic cord blood stem cells are CD34+, CD90+, CD184+, CD117+, CD49f+, ALDH+, and CD45RA− and wherein said treating and said culturing are effective to transiently express pluripotency genes SOX2, OCT4, NANOG, and ZIC3.

2. The method according to claim 1, wherein the isolated population of non-recombinant human hematopoietic cord blood stem cells is expanded by about 20,202 fold upon said treating.

3. The method according to claim 1, wherein said culturing is carried out for 7 days.

4. The method according to claim 1, wherein the expanded non-recombinant human hematopoietic cord blood stem cells do not show upregulation in the expression level of embryonic stem cell pluripotency gene hTERT.

5. The method according to claim 1, wherein the serum-free culture system further comprises SCF, Flt3 ligand, TPO, IL3.

6. The method according to claim 1, wherein the expanded non-recombinant human hematopoietic cord blood stem cells have reduced expression of HDAC1, HDAC3, and HDAC5 compared to the isolated hematopoietic stem cells before said treating.

7. The method according to claim 1, wherein at least about 18.0%±1.2% of the expanded non-recombinant human hematopoietic cord blood stem cells are in G2/M phase.

8. The method according to claim 1, wherein at least about 23.2%±13.8% of the expanded non-recombinant human hematopoietic cord blood stem cells are in G0/G1 phase.

* * * * *

```
                       SEQUENCE LISTING

<160> NUMBER OF SEQ ID NOS: 22

<210> SEQ ID NO 1
<211> LENGTH: 18
<212> TYPE: DNA
<213> ORGANISM: Artificial
<220> FEATURE:
<223> OTHER INFORMATION: Pseudo OCT4 Primer Sequence

<400> SEQUENCE: 1
gaaggtattc agccaaac                                                    18

<210> SEQ ID NO 2
<211> LENGTH: 19
<212> TYPE: DNA
<213> ORGANISM: Artificial
<220> FEATURE:
<223> OTHER INFORMATION: Pseudo OCT4 Primer Sequence

<400> SEQUENCE: 2
cttaatccaa aaaccctgg                                                   19

<210> SEQ ID NO 3
<211> LENGTH: 20
<212> TYPE: DNA
<213> ORGANISM: Artificial
<220> FEATURE:
<223> OTHER INFORMATION: Pseudo OCT4 Primer Sequence

<400> SEQUENCE: 3
cgaccatctg ccgctttgag                                                  20

<210> SEQ ID NO 4
<211> LENGTH: 20
<212> TYPE: DNA
<213> ORGANISM: Artificial
<220> FEATURE:
<223> OTHER INFORMATION: Pseudo OCT4 Primer Sequence

<400> SEQUENCE: 4 cccctgtcc cccattccta                                                   20

<210> SEQ ID NO 5
<211> LENGTH: 24
<212> TYPE: DNA
<213> ORGANISM: Artificial
<220> FEATURE:
<223> OTHER INFORMATION: Pseudo OCT4 Primer Sequence

<400> SEQUENCE: 5
aacctggagt ttgtgccagg gttt                                             24
```

-continued

```
<210> SEQ ID NO 6
<211> LENGTH: 24
<212> TYPE: DNA
<213> ORGANISM: Artificial
<220> FEATURE:
<223> OTHER INFORMATION: Pseudo OCT4 Primer Sequence

<400> SEQUENCE: 6
tgaacttcac cttccctcca acca                                          24

<210> SEQ ID NO 7
<211> LENGTH: 29
<212> TYPE: DNA
<213> ORGANISM: Artificial
<220> FEATURE:
<223> OTHER INFORMATION: SOX2 Primer Sequence

<400> SEQUENCE: 7
agaagaggag agagaaagaa agggagaga                                     29

<210> SEQ ID NO 8
<211> LENGTH: 29
<212> TYPE: DNA
<213> ORGANISM: Artificial
<220> FEATURE:
<223> OTHER INFORMATION: SOX2 Primer Sequence

<400> SEQUENCE: 8
gagagaggca aactggaatc aggatcaaa                                     29

<210> SEQ ID NO 9
<211> LENGTH: 22
<212> TYPE: DNA
<213> ORGANISM: Artificial
<220> FEATURE:
<223> OTHER INFORMATION: NANOG Primer Sequence

<400> SEQUENCE: 9
cctgaagacg tgtgaagatg ag                                            22

<210> SEQ ID NO 10
<211> LENGTH: 22
<212> TYPE: DNA
<213> ORGANISM: Artificial
<220> FEATURE:
<223> OTHER INFORMATION: NANOG Primer Sequence

<400> SEQUENCE: 10
gctgattagg ctccaaccat ac                                            22

<210> SEQ ID NO 11
<211> LENGTH: 23
<212> TYPE: DNA
<213> ORGANISM: Artificial
<220> FEATURE:
<223> OTHER INFORMATION: TERT Primer Sequence

<400> SEQUENCE: 11
tgaaagccaa gaacgcaggg atg                                           23

<210> SEQ ID NO 12
<211> LENGTH: 25
<212> TYPE: DNA
<213> ORGANISM: Artificial
<220> FEATURE:
<223> OTHER INFORMATION: TERT Primer Sequence
```

```
<400> SEQUENCE: 12
tgtcgagtca gcttgagcag gaatg                                          25

<210> SEQ ID NO 13
<211> LENGTH: 23
<212> TYPE: DNA
<213> ORGANISM: Artificial
<220> FEATURE:
<223> OTHER INFORMATION: CD34 Primer Sequence

<400> SEQUENCE: 13
acaaacatca cagaaacgac agt                                            23

<210> SEQ ID NO 14
<211> LENGTH: 21
<212> TYPE: DNA
<213> ORGANISM: Artificial
<220> FEATURE:
<223> OTHER INFORMATION: CD34 Primer Sequence

<400> SEQUENCE: 14
tgacaggcta ggcttcaagg t                                              21

<210> SEQ ID NO 15
<211> LENGTH: 20
<212> TYPE: DNA
<213> ORGANISM: Artificial
<220> FEATURE:
<223> OTHER INFORMATION: SET Primer Sequence

<400> SEQUENCE: 15
gcaagaagcg attgaacaca                                                20

<210> SEQ ID NO 16
<211> LENGTH: 20
<212> TYPE: DNA
<213> ORGANISM: Artificial
<220> FEATURE:
<223> OTHER INFORMATION: SET Primer Sequence

<400> SEQUENCE: 16
gcagtgcctc ttcatcttcc                                                20

<210> SEQ ID NO 17
<211> LENGTH: 20
<212> TYPE: DNA
<213> ORGANISM: Artificial
<220> FEATURE:
<223> OTHER INFORMATION: MYST3 Primer Sequence

<400> SEQUENCE: 17
actccaccac ctacgaatgc                                                20

<210> SEQ ID NO 18
<211> LENGTH: 20
<212> TYPE: DNA
<213> ORGANISM: Artificial
<220> FEATURE:
<223> OTHER INFORMATION: MYST3 Primer Sequence

<400> SEQUENCE: 18
ctccttcctc agcctcctct                                                20

<210> SEQ ID NO 19
<211> LENGTH: 20
```

```
<212> TYPE: DNA
<213> ORGANISM: Artificial
<220> FEATURE:
<223> OTHER INFORMATION: SMARCAD1 Primer Sequence

<400> SEQUENCE: 19
tggaagacct ttcggaattg                                              20

<210> SEQ ID NO 20
<211> LENGTH: 20
<212> TYPE: DNA
<213> ORGANISM: Artificial
<220> FEATURE:
<223> OTHER INFORMATION: SMARCAD1 Primer Sequence

<400> SEQUENCE: 20
cacctgcatc accaaacatc                                              20

<210> SEQ ID NO 21
<211> LENGTH: 20
<212> TYPE: DNA
<213> ORGANISM: Artificial
<220> FEATURE:
<223> OTHER INFORMATION: ZIC3 Primer Sequence

<400> SEQUENCE: 21
gcaagtcttt caaggcgaag                                              20

<210> SEQ ID NO 22
<211> LENGTH: 20
<212> TYPE: DNA
<213> ORGANISM: Artificial
<220> FEATURE:
<223> OTHER INFORMATION: ZIC3 Primer Sequence

<400> SEQUENCE: 22
catgcatgtg cttcttacgg                                              20
```